US011931015B2

(12) United States Patent
Muse

(10) Patent No.: US 11,931,015 B2
(45) Date of Patent: Mar. 19, 2024

(54) BONE BIOPSY DEVICES, SYSTEMS, AND METHODS

(71) Applicant: PIPER ACCESS, LLC, Salt Lake City, UT (US)

(72) Inventor: Jay Allen Muse, Salt Lake City, UT (US)

(73) Assignee: Piper Access, LLC, Salt Lake City, UT (US)

(*) Notice: Subject to any disclaimer, the term of this patent is extended or adjusted under 35 U.S.C. 154(b) by 822 days.

(21) Appl. No.: 16/293,627

(22) Filed: Mar. 5, 2019

(65) Prior Publication Data

US 2019/0328370 A1    Oct. 31, 2019

Related U.S. Application Data

(60) Provisional application No. 62/795,683, filed on Jan. 23, 2019, provisional application No. 62/662,678, filed on Apr. 25, 2018, provisional application No. 62/638,433, filed on Mar. 5, 2018.

(51) Int. Cl.
*A61B 10/02* (2006.01)
*A61B 17/16* (2006.01)

(52) U.S. Cl.
CPC ........ *A61B 10/025* (2013.01); *A61B 10/0266* (2013.01); *A61B 2010/0208* (2013.01); *A61B 2010/0258* (2013.01); *A61B 10/0283* (2013.01); *A61B 17/1635* (2013.01); *A61B 17/1637* (2013.01)

(58) Field of Classification Search
CPC .............. A61B 10/025; A61B 10/0266; A61B 10/0283; A61B 17/1637; A61B 2010/0208; A61B 2010/0258; A61B 17/3472
See application file for complete search history.

(56) References Cited

U.S. PATENT DOCUMENTS

| | | |
|---|---|---|
| 4,838,282 A | 6/1989 | Strasser et al. |
| 4,936,313 A | 6/1990 | Burkhardt et al. |
| 5,257,632 A | 11/1993 | Turkel et al. |
| 5,357,974 A | 10/1994 | Baldridge |

(Continued)

FOREIGN PATENT DOCUMENTS

| | | |
|---|---|---|
| CN | 102247174 A | 11/2011 |
| CN | 107714137 | 2/2018 |

(Continued)

OTHER PUBLICATIONS

Piper Access, LLC, Response to Extended European Search Report in European Patent Application No. 19763839.8, dated May 19, 2022, 152 pages.

(Continued)

*Primary Examiner* — Sean P Dougherty
(74) *Attorney, Agent, or Firm* — Med Venture Management, LLC; Daniel C. Higgs

(57) ABSTRACT

A bone biopsy system can include a cutting cannula that is coupled to a powered drill. The powered drill can be actuated to rotate the cutting cannula and cut through a cortical layer of a bone. The powered drill can be decoupled from the cutting cannula while the cutting cannula extends through the cortical layer of the bone. A handle may then be used to manually advance the cutting cannula to a greater depth within the bone to core a sample.

30 Claims, 59 Drawing Sheets

(56) References Cited

U.S. PATENT DOCUMENTS

| | | | |
|---|---|---|---|
| 5,522,398 A | 6/1996 | Goldenberg et al. | |
| 5,595,186 A | 1/1997 | Rubinstein et al. | |
| 6,022,324 A | 2/2000 | Skinner | |
| 6,110,128 A | 8/2000 | Andelin et al. | |
| 6,755,793 B2 | 6/2004 | Lamoureux et al. | |
| 7,670,328 B2 | 3/2010 | Miller | |
| 7,699,850 B2 | 4/2010 | Miller | |
| 7,850,620 B2 | 12/2010 | Miller et al. | |
| 7,951,089 B2 | 5/2011 | Miller | |
| 8,308,693 B2 | 11/2012 | Miller et al. | |
| 8,419,683 B2 | 4/2013 | Miller et al. | |
| 8,656,929 B2 | 2/2014 | Miller et al. | |
| 8,668,698 B2 | 3/2014 | Miller et al. | |
| 8,690,791 B2 | 4/2014 | Miller | |
| 8,944,069 B2 | 2/2015 | Miller et al. | |
| 9,078,637 B2 | 7/2015 | Miller | |
| 9,314,270 B2 | 4/2016 | Miller | |
| 9,439,667 B2 | 9/2016 | Miller | |
| 9,451,968 B2 | 9/2016 | Miller et al. | |
| 9,504,477 B2 | 11/2016 | Miller et al. | |
| 9,510,910 B2 | 12/2016 | Miller et al. | |
| 9,545,243 B2 | 1/2017 | Miller et al. | |
| 9,717,564 B2 | 8/2017 | Miller et al. | |
| 2002/0042581 A1* | 4/2002 | Cervi | A61B 10/025 600/567 |
| 2003/0225344 A1 | 12/2003 | Miller | |
| 2007/0016100 A1 | 1/2007 | Miller | |
| 2007/0276352 A1 | 11/2007 | Crocker et al. | |
| 2009/0204024 A1 | 8/2009 | Miller | |
| 2010/0137740 A1 | 6/2010 | Miller | |
| 2013/0096561 A1 | 4/2013 | Miller et al. | |
| 2013/0131548 A1* | 5/2013 | McGhie | A61B 10/0266 600/567 |
| 2013/0204160 A1 | 8/2013 | McKenna et al. | |
| 2015/0223786 A1 | 8/2015 | Morgan et al. | |
| 2016/0374722 A1 | 12/2016 | Miller | |
| 2017/0007271 A1 | 1/2017 | Miller et al. | |
| 2017/0340401 A1 | 11/2017 | Miller et al. | |
| 2018/0125465 A1* | 5/2018 | Muse | A61M 5/158 |

FOREIGN PATENT DOCUMENTS

| | | |
|---|---|---|
| JP | 2002-538922 A | 11/2002 |
| WO | 2019173411 | 9/2019 |

OTHER PUBLICATIONS

International Searching Authority, International Search Report in International Application No. PCT/US2019/020847, dated May 14, 2019, 2 pages.

International Searching Authority, Written Opinion of the International Searching Authority in International Application No. PCT/US2019/020847, dated May 14, 2019, 8 pages.

European Patent Office, Extended European Search Report in European Patent Application No. 19763839.8, dated Oct. 22, 2021, 9 pages.

Japan Patent Office, Notice of Reasons for Rejection, dated Jan. 11, 2023 (4 pages).

National Institute of Industrial Property, Search Report in Brazilian Patent Application No. BR112020018122-6, dated Apr. 6, 2023, 8 pages.

Japan Patent Office, Notice of Patent Grant in Japanese Patent Application No. 2020-546360, dated Jun. 5, 2023, 6 pages.

European Patent Office, Communication pursuant to Article 94(3) EPC in European Patent Application No. 19763839.8, dated Jul. 4, 2023, 4 pages.

Korean Intellectual Property Office, Notice to Submit Response in Korean Patent Application No. KR 10-2020-7028538, dated Dec. 22, 2023, 5 pages.

\* cited by examiner

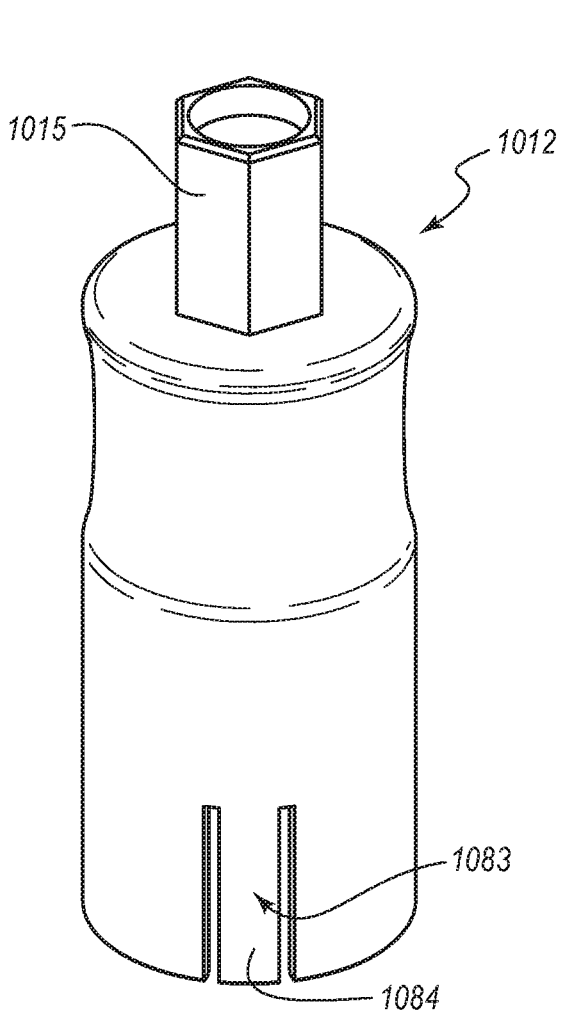
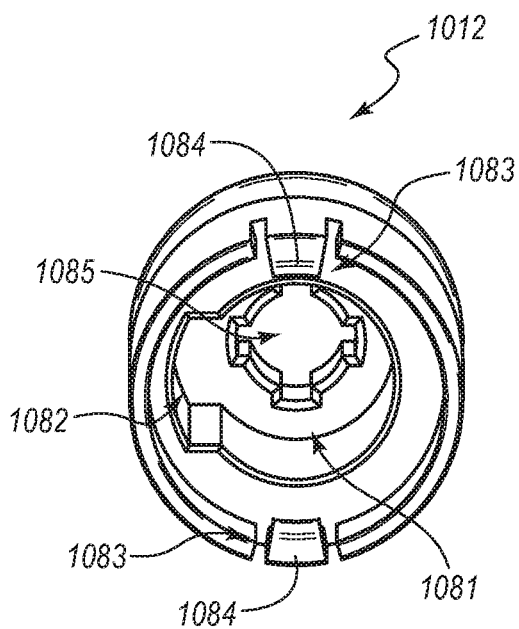
FIG. 20A
FIG. 20B
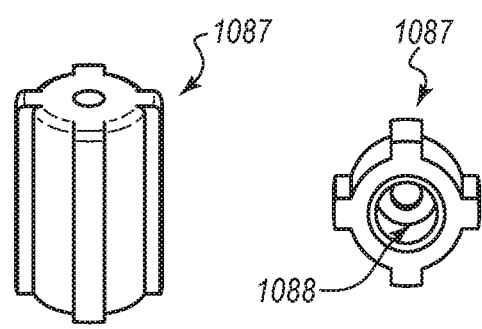
FIG. 21A    FIG. 21B
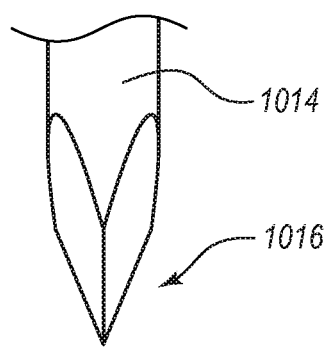
FIG. 22
FIG. 23

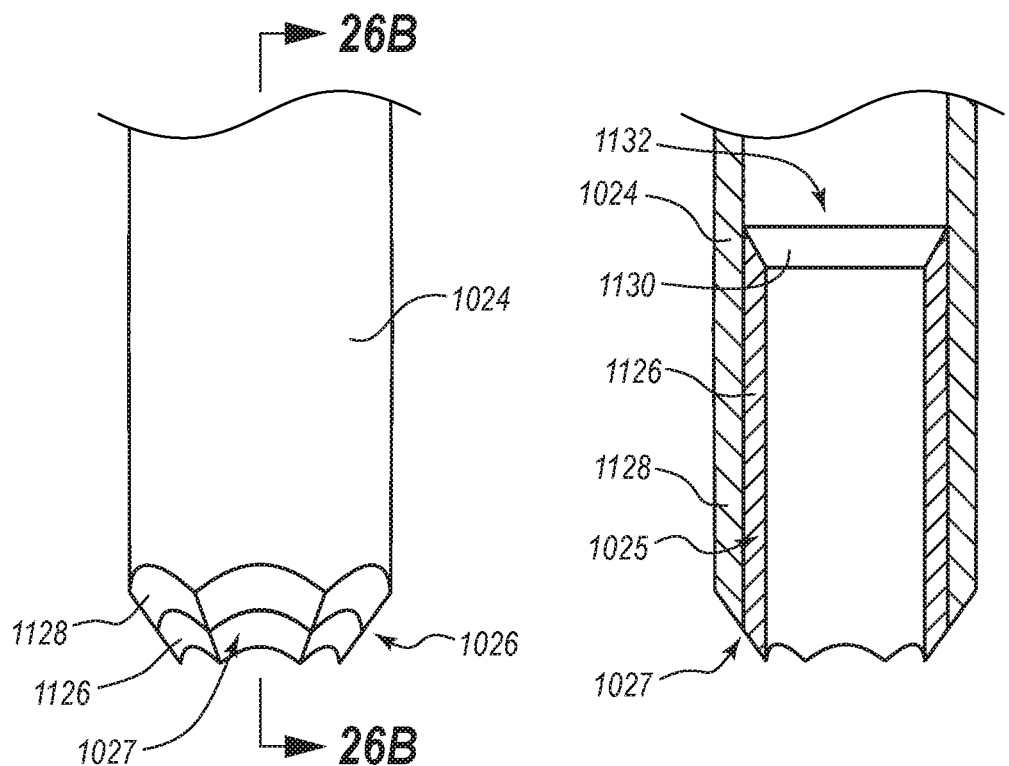
FIG. 26A
FIG. 26B
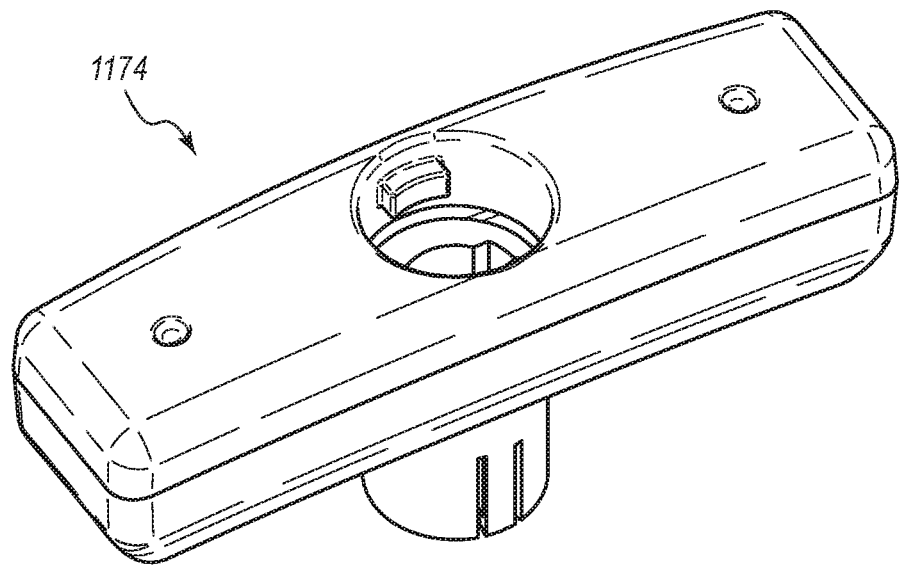
FIG. 27A

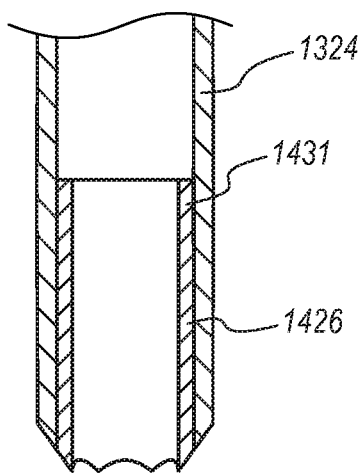
FIG. 38
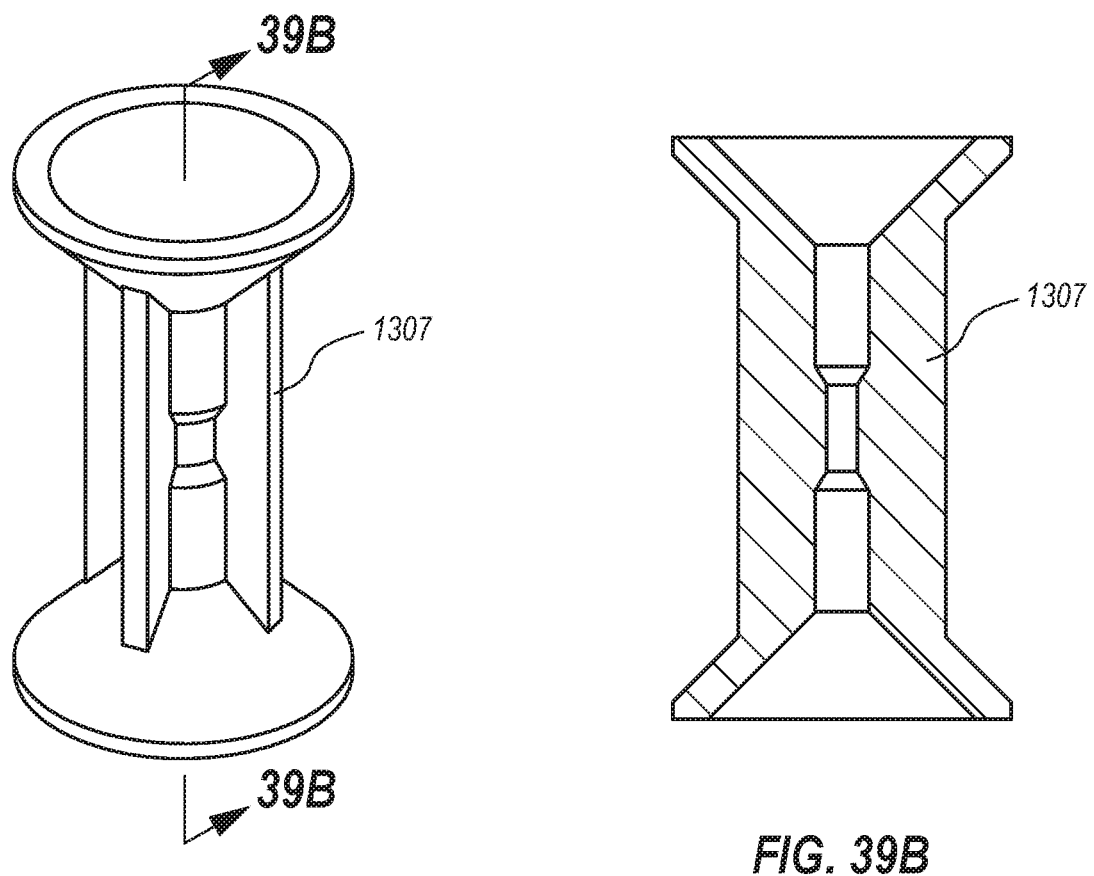
FIG. 39A
FIG. 39B

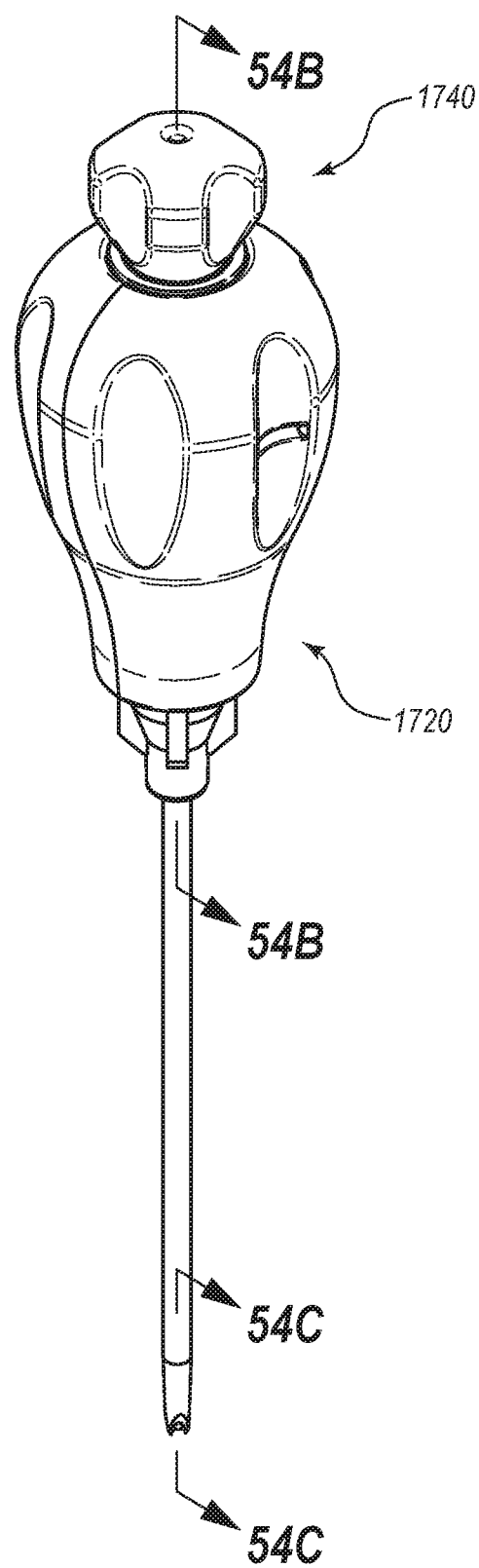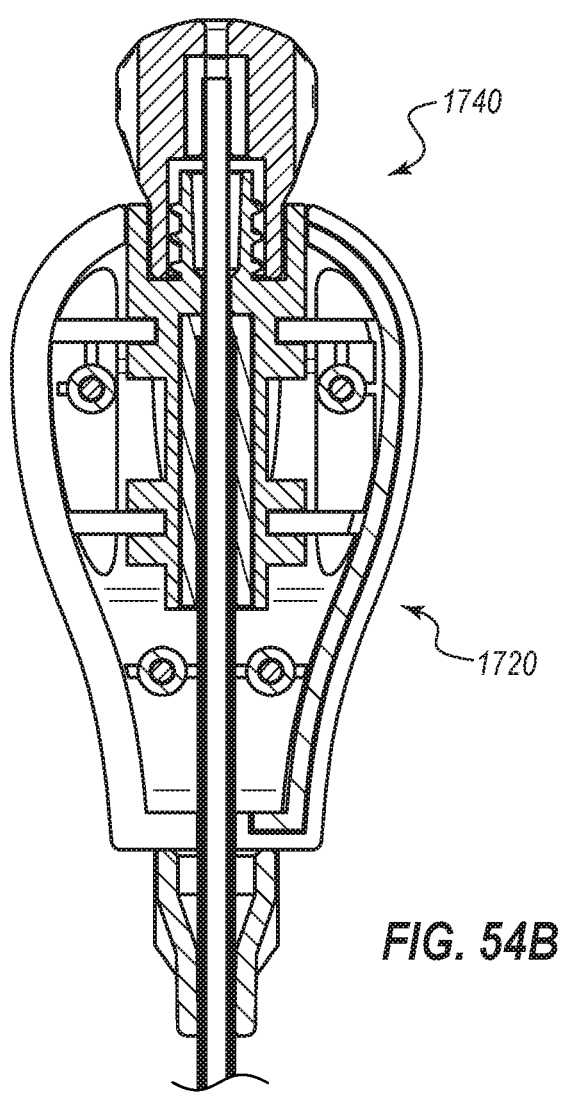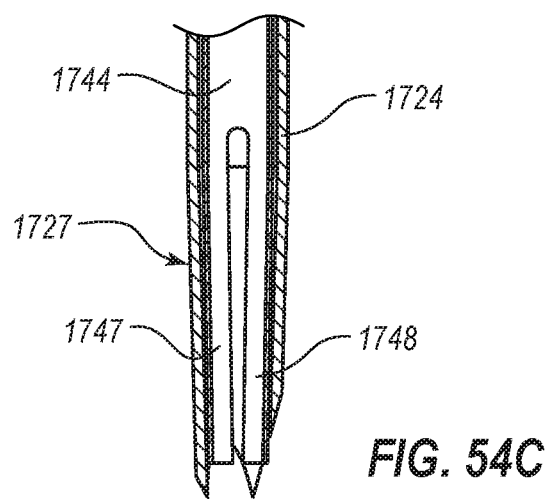
FIG. 54A
FIG. 54B
FIG. 54C

BONE BIOPSY DEVICES, SYSTEMS, AND METHODS

CROSS-REFERENCE TO RELATED APPLICATIONS

This application claims the benefit under 35 U.S.C. § 119(e) of U.S. Provisional Patent Application No. 62/638,433, titled BONE BIOPSY DEVICES, SYSTEMS, AND METHODS, filed on Mar. 5, 2018, U.S. Provisional Patent Application No. 62/662,678, titled BONE BIOPSY DEVICES, SYSTEMS, AND METHODS, filed on Apr. 25, 2018, and U.S. Provisional Patent Application No. 62/795,683, titled BONE BIOPSY DEVICES, SYSTEMS, AND METHODS, filed on Jan. 23, 2019, the entire contents of each of which are hereby incorporated by reference herein.

TECHNICAL FIELD

Certain embodiments described herein relate generally to devices and systems for insertion in a bone, and further embodiments relate more particularly to bone biopsy devices, systems, and methods.

BACKGROUND

Known devices, systems, and methods for bone biopsies suffer from a variety of drawbacks. Embodiments disclosed herein remedy, ameliorate, or avoid one or more of such drawbacks.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 20A is an upper perspective view of an embodiment of a trocar hub compatible with an embodiment of a trocar assembly of the bone biopsy system of FIG. 19;

FIG. 20B is a lower perspective view of the trocar hub of FIG. 20A;

FIG. 21A is an upper perspective view of an embodiment of a spline element compatible with the trocar hub;

FIG. 21B is a lower perspective view of the spline element;

FIG. 22 is a perspective view of an embodiment of a magnet compatible with the trocar hub;

FIG. 23 is an elevation view of a distal end of an embodiment of a trocar compatible with the trocar assembly;

FIG. 26A is an elevation view of a distal end of a cutting cannula of the cutting assembly;

FIG. 26B is a cross-sectional view of the distal end of the cutting cannula taken along the view line 26B-26B in FIG. 26A;

FIG. 27A is an upper perspective view of an embodiment of a handle compatible with the hub of FIG. 24A;

FIG. 38 is a cross-sectional view of a distal end of the cutting cannula of the system of FIG. 37, similar to the view depicted in FIG. 26B;

FIG. 39A is perspective view of the guide shown in FIG. 37;

FIG. 39B is a cross-sectional view of the guide taken along the view line 39B-39B in FIG. 39A;

FIG. 54A is a perspective view of the extraction assembly coupled with the cutting assembly;

FIG. 54B is a cross-sectional view of the extraction assembly coupled with the cutting assembly taken along the view line 54B-54B in FIG. 54A;

FIG. 54C is a cross-sectional view of a distal end of the extraction assembly coupled with the cutting assembly taken along the view line 54C-54C in FIG. 54A;

DETAILED DESCRIPTION

Figure 1:
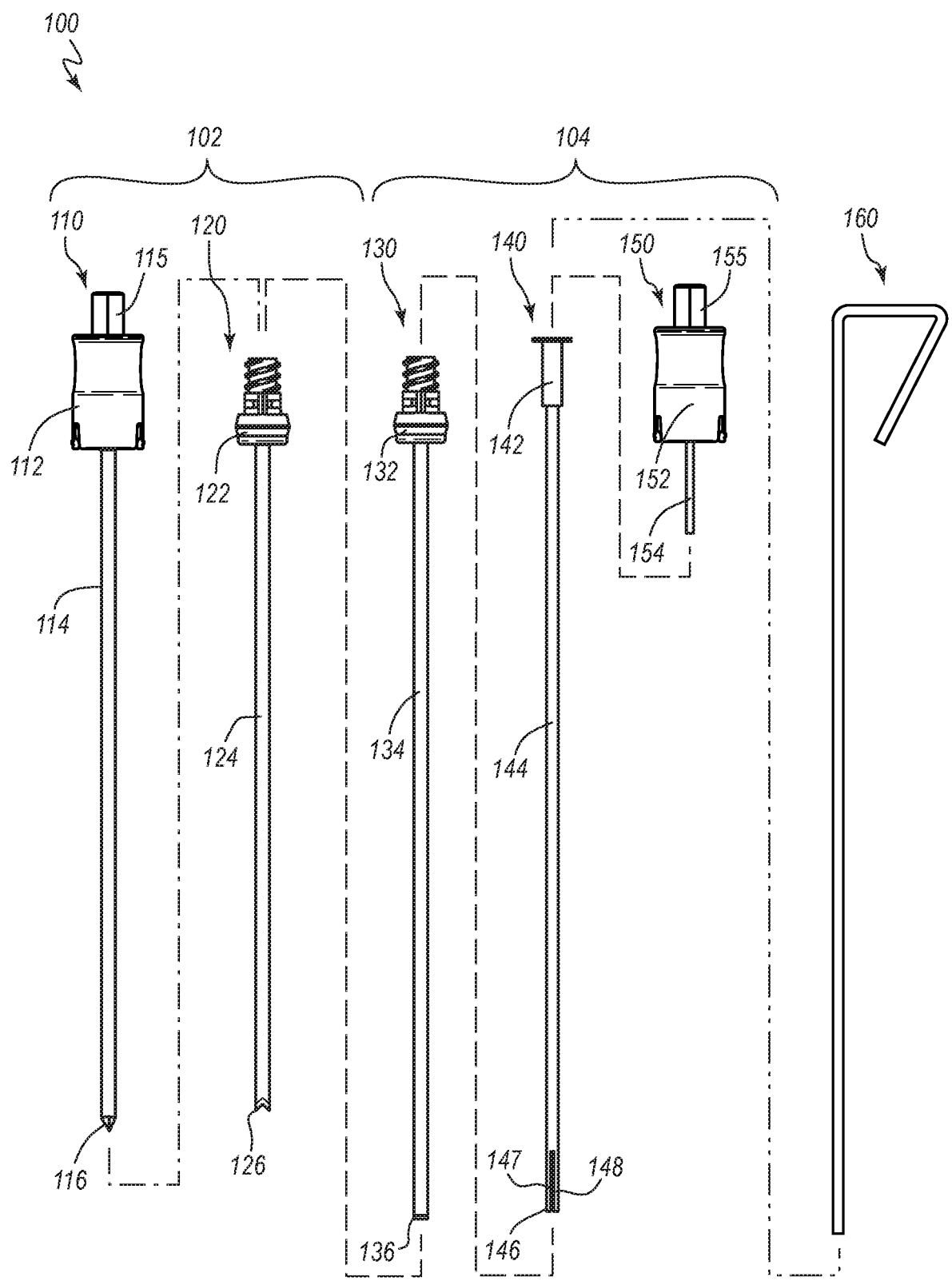
FIG. 1 is an elevation view of an embodiment of a bone biopsy system.

The present disclosure relates generally to devices, systems, and methods for bone biopsies. Known systems for bone biopsies generally suffer from one of more drawbacks. For example, some systems do not preserve well the integrity of a sample. Whereas it is desirable to maintain a sample in a stratified, non-crushed state, many known systems damage the sample or otherwise render it suboptimal for analysis. For example, some systems do not provide viable samples for use in certain analyses, as the samples may suffer from crushing (and resultant crush artifact). Stated otherwise, known systems provide only low diagnostic yields.

Moreover, certain known systems either utilize only manual drills or only powered drills for bone biopsy procedures. Manual-only systems can be advantageous, in some instances, due to slower drilling speeds and/or greater control achievable by practitioners, which may lead to better marrow samples, as compared with powered systems. However, such manual-only systems can suffer from the difficulty and/or extended length of time that it can take for a practitioner to drill through hard cortical bone in order to access the bone marrow. Such difficult or time-intensive procedures, beyond being difficult and costly (e.g., due to extended time in an operating room), can also have potential hazards, such as breaking or bending a needle in a patient. Moreover, the pain associated with such procedures can be proportional to their duration, such that longer procedures are more painful for a patient. In some instances, patients may require costly sedation or anesthetization for such procedures due to the greater pain associated therewith. In other or further instances, patients may forego potentially beneficial follow-up procedures due to the difficulty or pain associated with prior procedures.

Certain powered systems can more readily penetrate through the cortical bone layer than manual systems, thus avoiding some of the drawbacks of manual systems. Although certain of such systems yield core samples of approximately the same quality of those that may be achieved from manual systems, others yield inferior core samples, such as, for example, due to crushing or other disruption of the intrinsic structure of the sample. Accordingly, practitioners generally use manual systems, but may use powered systems in certain cases of lesion extraction in which it can be necessary to penetrate a hard, cortical layer to access the marrow of a bone.

Certain embodiments disclosed herein can remedy, ameliorate, or avoid one or more limitations or drawbacks of known biopsy systems. For example, certain embodiments disclosed herein can obtain marrow samples in a substantially undisturbed state, can maintain an integrity of the samples, or stated otherwise, can provide high diagnostic yields. Stated otherwise, certain embodiments disclosed herein can be used to extract and preserve the original structural integrity of a bone marrow sample, thereby reducing the occurrence of damage to the marrow sample, such as crush artifacts, and thereby increasing the diagnostic yield.

Moreover, certain embodiments disclosed herein employ a hybrid approach in which a powered driver is used for penetrating the cortical layer of a bone in a quick and/or simple manner and in which manual manipulation achieves further advancement into the bone to obtain a core sample of the marrow. Certain of such systems simultaneously achieve at least some of the benefits associated with both powered drilling through the cortex (e.g., speed, reduced pain) and manual advancement of a core sampling device through the marrow (e.g., increased diagnostic yield).

In some embodiments a cutting cannula is used during the powered drilling, which cannula remains in place within the cortex. In various embodiments, a trocar may be used in conjunction with the cutting cannula to achieve the cutting, and in other embodiments, an obturator is used with the cutting cannula. After the cutting cannula has been advanced through the cortex and the trocar or obturator removed, an extraction cannula is inserted into the cutting cannula and a manual driver is used with the extraction cannula to obtain a core sample. In some embodiments, the extraction cannula is used in conjunction with a separate coring cannula. A manual driver can be coupled to the coring cannula, which is inserted through the cutting cannula while the cutting cannula remains in place in the cortex. The manual driver is then manipulated to advance the coring cannula past a distal tip of the cutting cannula to obtain a sample. The extraction cannula can either be coupled with the coring cannula during the coring event, or may be inserted through the coring cannula after the coring has taken place. The extraction cannula captures the cored sample and is removed from the patient, and the sample is then removed from the extraction cannula.

In other embodiments, rather than using a separate coring cannula, the cutting cannula can be manually manipulated and advanced further into the bone to obtain the cored sample. For example, in some instances, the manual driver is coupled to the cutting cannula and is manipulated by the user to cut a core sample from the marrow via the cutting cannula.

In some embodiments, a cutting cannula is coupled with a powered driver (e.g., a handheld drill) to drill through cortical bone and advance a distal end of the cutting cannula past the cortex. In certain of such instances, the cutting cannula is coupled with a trocar, which assists with cutting the cortex. Once the distal end of the cutting cannula has moved past the cortex, the powered driver and the trocar (where applicable) are removed while leaving the cutting cannula in place.

The cutting cannula is then manually advanced further into the bone to obtain a core sample. In some instances, a separate handle is attached to the cutting cannula, subsequent to using the drill, to achieve manual manipulation of the cutting cannula. In other instances, a handle that is fixedly secured to the cutting cannula is in place prior to the drilling, remains in place during the drilling, and is subsequently used to achieve manual manipulation of the cutting cannula.

In some embodiments, an extraction cannula is inserted into the cutting cannula to capture the core sample. In certain of such embodiments, the extraction cannula is coupled with the cutting cannula prior to manual advancement of the cutting cannula, such that the cutting cannula and the extraction cannula are advanced in unison and the core sample enters into the extraction cannula while the cutting cannula is advanced through the bone. In other embodiments, the cutting cannula cores a sample that is received into a lumen of the cutting cannula, and the extraction cannula is subsequently advanced into the lumen of the cutting cannula and over the cored sample to couple with the sample. The extraction cannula can be retracted from the patient and the cored sample can then be removed therefrom.

In still other embodiments, the cutting cannula is configured to retain the cored sample therein, such that the cutting cannula itself can be used to extract the cored sample from the bone. In certain of such embodiments, no separate extraction cannula is used. After retraction of the cutting cannula from the patient, the cored sample is removed from the cutting cannula.

Accordingly, various embodiments include both powered and manual components. Certain embodiments can be quick and/or easy to use and/or can provide practitioners with controlled creation and extraction of a core sample. One or more of the foregoing and/or other advantages will be apparent from the present disclosure. Other and further embodiments and the advantages thereof are also disclosed and made apparent.

FIG. 1 depicts an embodiment of a bone biopsy system 100. The system 100 includes a cortical drilling assembly 102 and a coring and extraction assembly 104. The assemblies 102, 104 may also be referred to as a cortical drilling system and as a coring and extraction system, respectively. Indeed, as discussed further below, the bone biopsy system 100 can include numerous sub-systems, which can involve different combinations and uses of the various components of the system 100. Each such combination may be termed as a separate system, and each such system may be claimed separately.

The cortical drilling assembly 102 can include a trocar assembly 110 and a cutting assembly 120. The trocar assembly 110 includes a hub 112, a trocar 114 fixedly secured to the hub 112, and a cutting tip 116 at a distal end of the trocar 114. The cutting assembly 120 includes a hub 122, a cutting cannula 124 fixedly secured to the hub 122, and a cutting tip 126 at a distal end of the cutting cannula 124.

Figure 2:
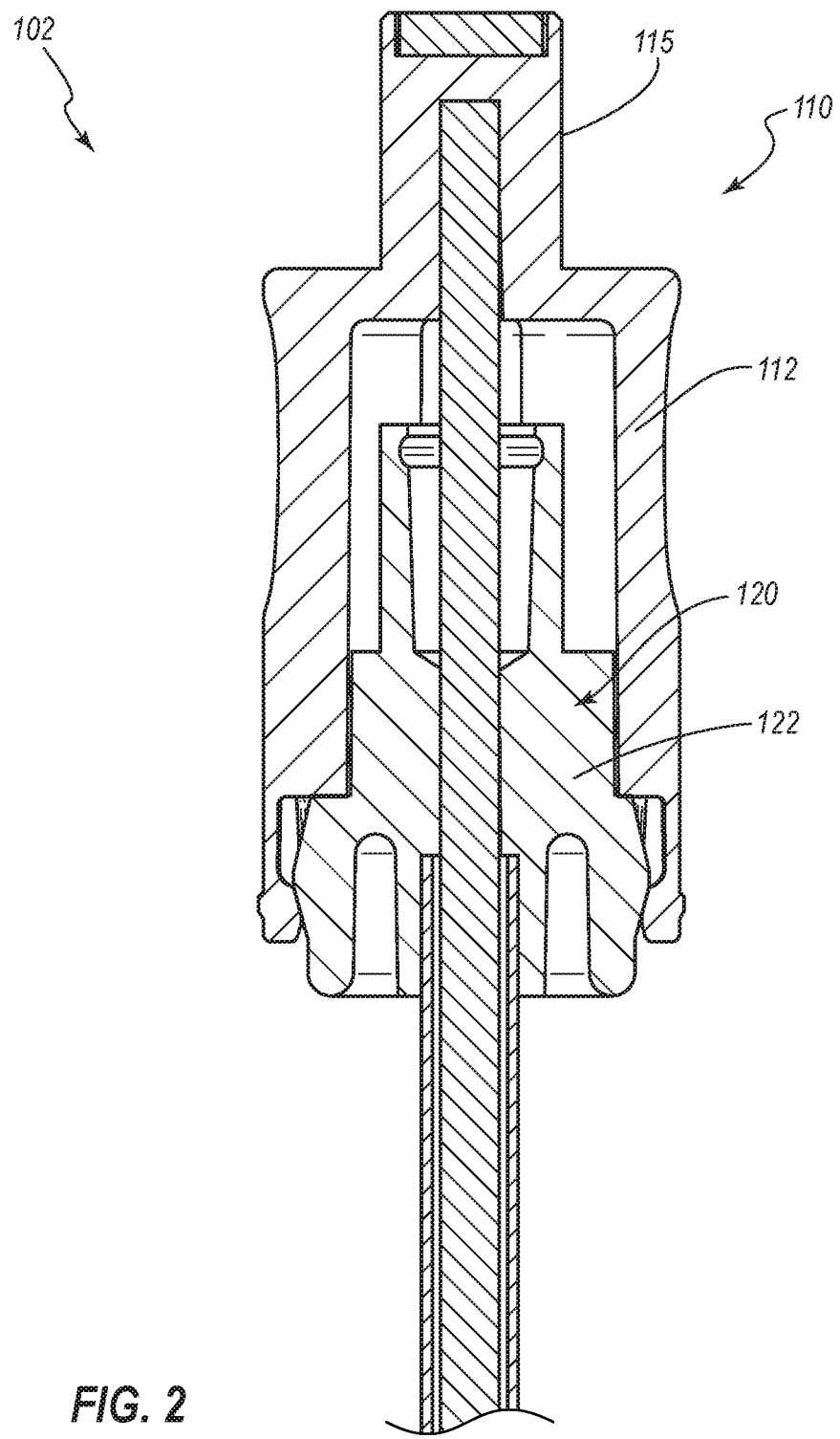
FIG. 2 is a cross-sectional view of a proximal portion of a cortical drilling assembly, which is a portion of the system of FIG. 1.

As depicted in a first style of broken lines in FIG. 1, and as depicted in FIG. 2, the trocar assembly 110 can be inserted into and coupled with the cutting assembly 120. In particular, as further discussed, below, the trocar assembly 110 can be coupled with the cutting assembly 120 in a rotationally fixed manner such that the trocar assembly 110 and the cutting assembly 120 can rotate in unison, such as when driven by a powered driver (e.g., a handheld powered drill) or by a manual driver (e.g., a manually manipulable handle).

With continued reference to FIG. 1, the coring and extraction assembly 104 can include a coring assembly 130, an extraction assembly 140, and a stiffener assembly 150. The coring assembly 130 includes a hub 132, a coring cannula 134 fixedly secured to the hub 132, and a cutting tip 136 at a distal end of the coring cannula 134. The extraction assembly includes a hub 142, an extraction cannula 144 fixedly secured to the hub 142, and an extraction tip 146 at a distal end of the extraction cannula 144. The stiffener assembly 150 includes a hub 152 fixedly attached to a stiffener 154, which may also be referred to as a stylet or rod.

Figure 5A:
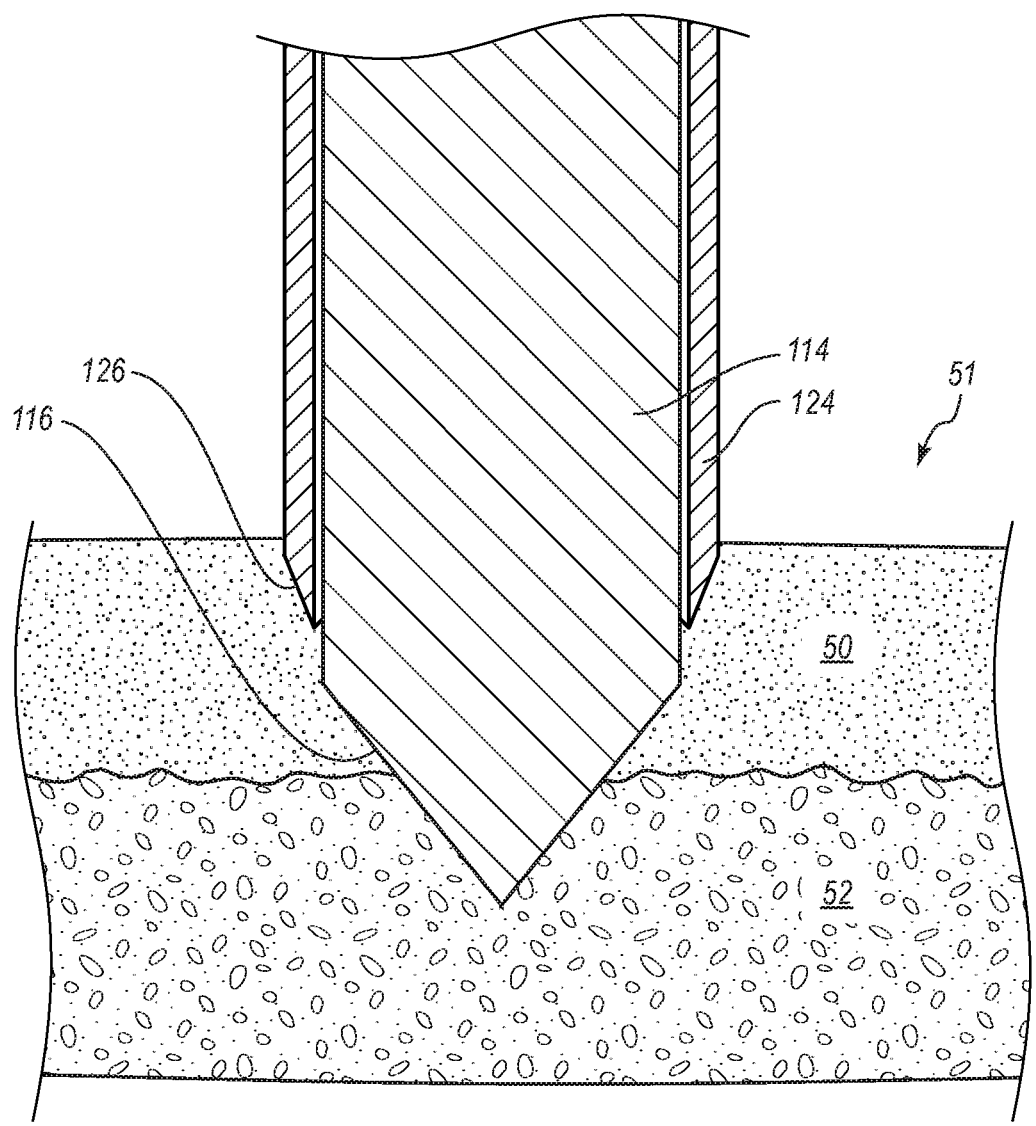
FIG. 5A is a cross-sectional view of a distal end of a portion of the system of FIG. 1 during a stage of an illustrative method of using the system, wherein a distal end of the cortical drilling assembly is being drilled through a cortical layer of a bone of a patient.
Figure 5B:
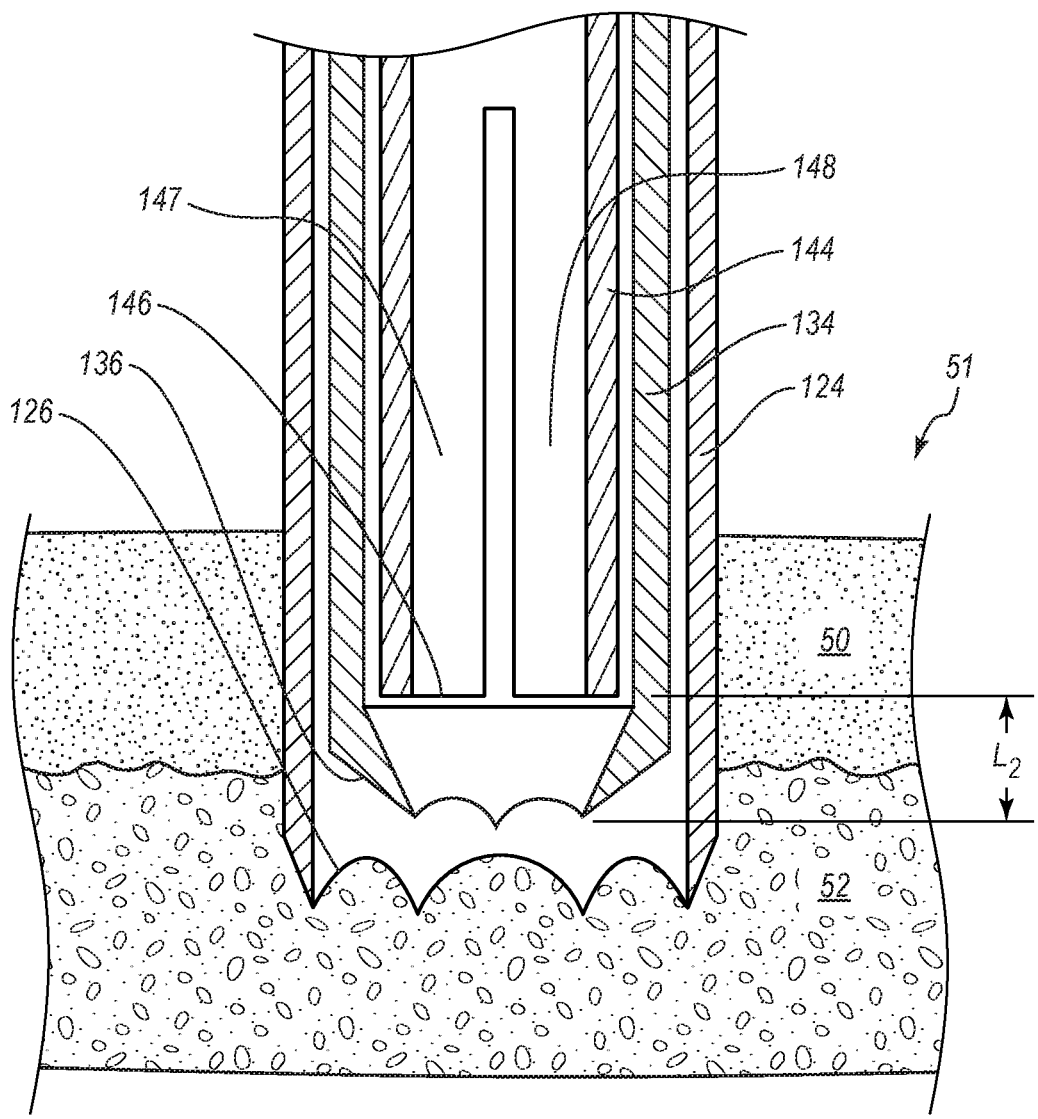
FIG. 5B is a cross-sectional view of a distal end of a portion of the system of FIG. 1 during a subsequent stage of the illustrative method, wherein a cutting cannula has been drilled through the cortical layer of the bone and has been left implanted in the bone, wherein a trocar has been removed from the cutting cannula, and wherein a distal end of the coring and extraction assembly is being inserted distally through the cutting cannula.
Figure 5C:
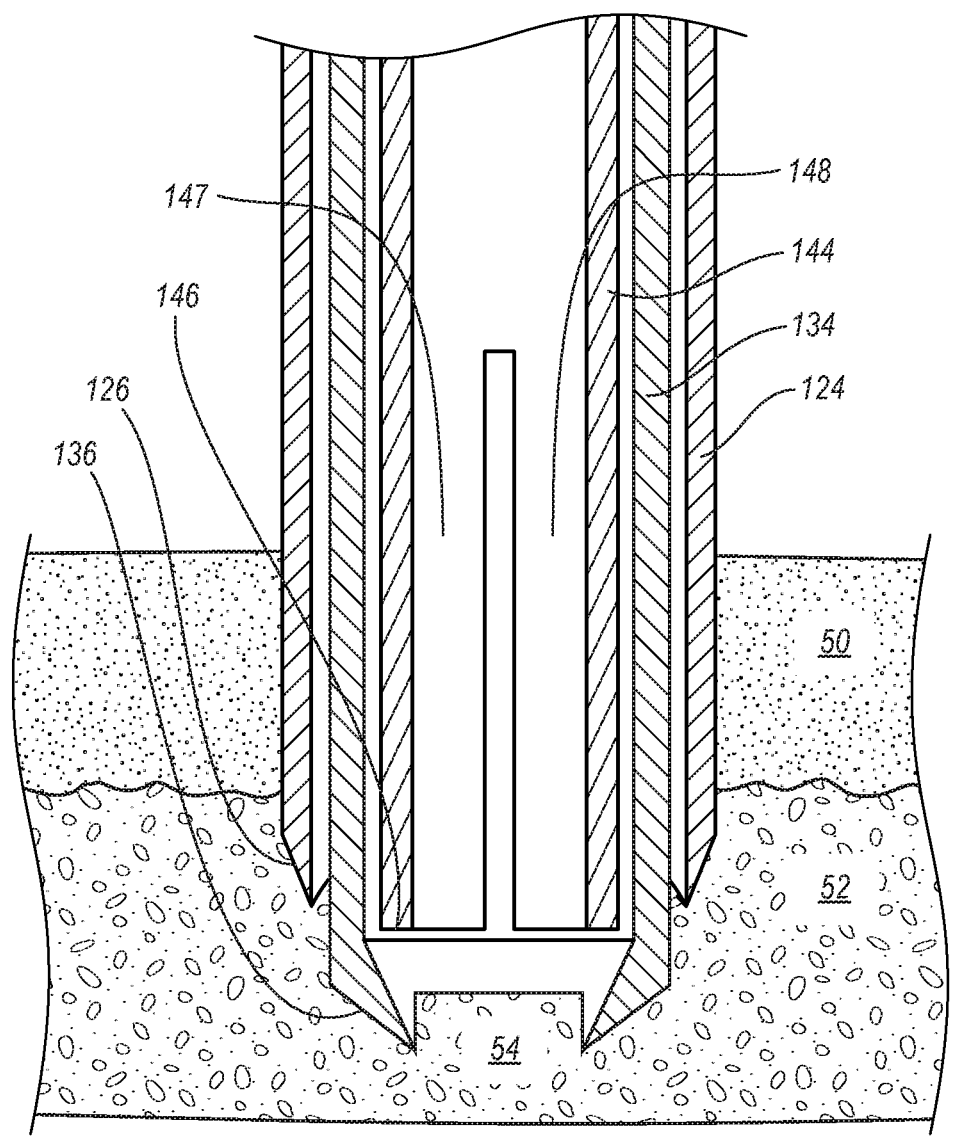
FIG. 5C is a cross-sectional view of the distal end of the portion of the system of FIG. 1 during a subsequent stage of the illustrative method, wherein a distal tip of a coring cannula has begun cutting through marrow of the bone to form a core sample, or core, of the marrow.
Figure 5D:
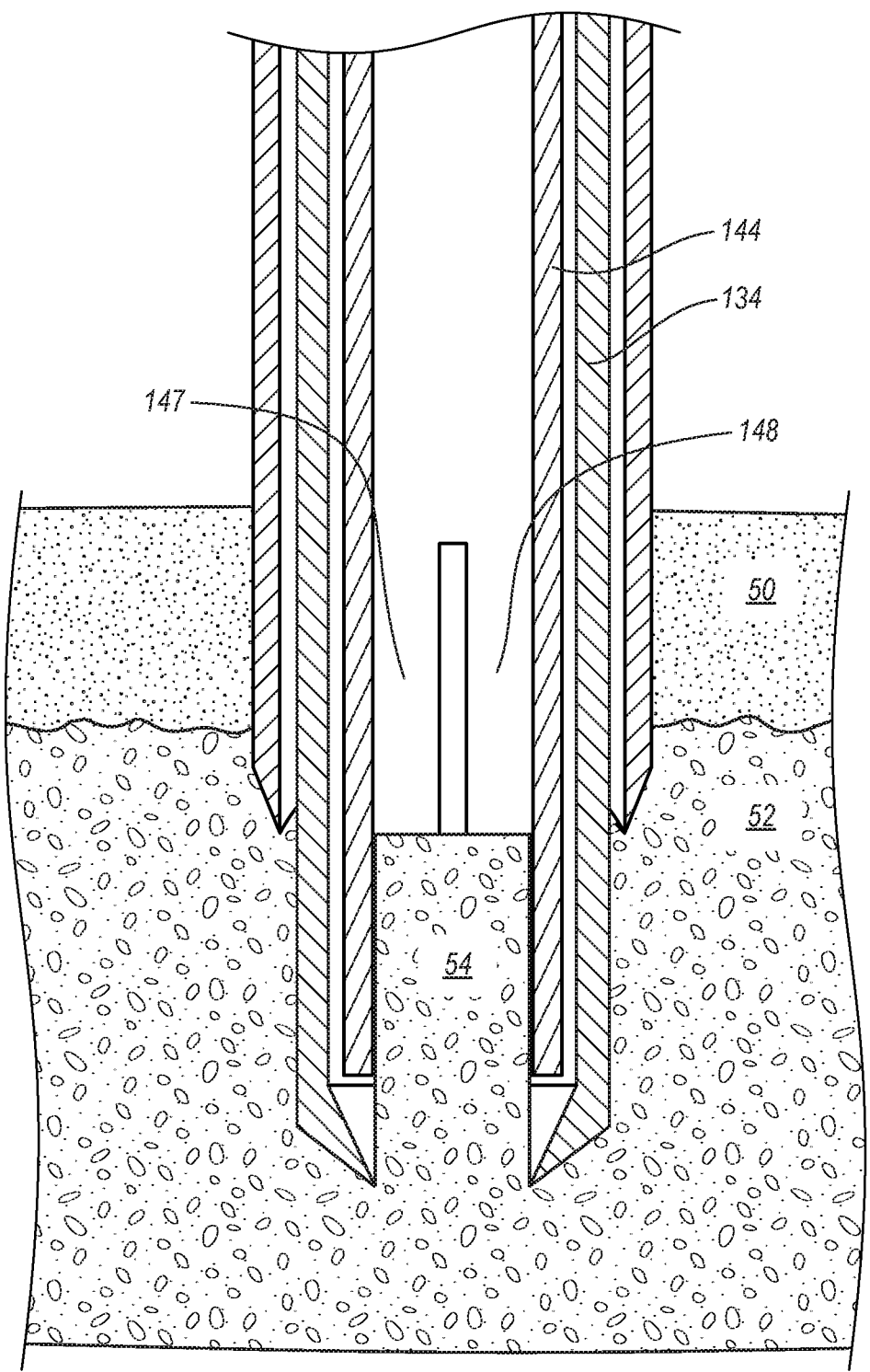
FIG. 5D is a cross-sectional view of the distal end of the portion of the system of FIG. 1 during a subsequent stage of the illustrative method, wherein the distal tip of the coring cannula has continued cutting through the marrow of the bone to increase the size of the core, and the core has entered into a distal tip of a sample extraction cannula.
Figure 5E:
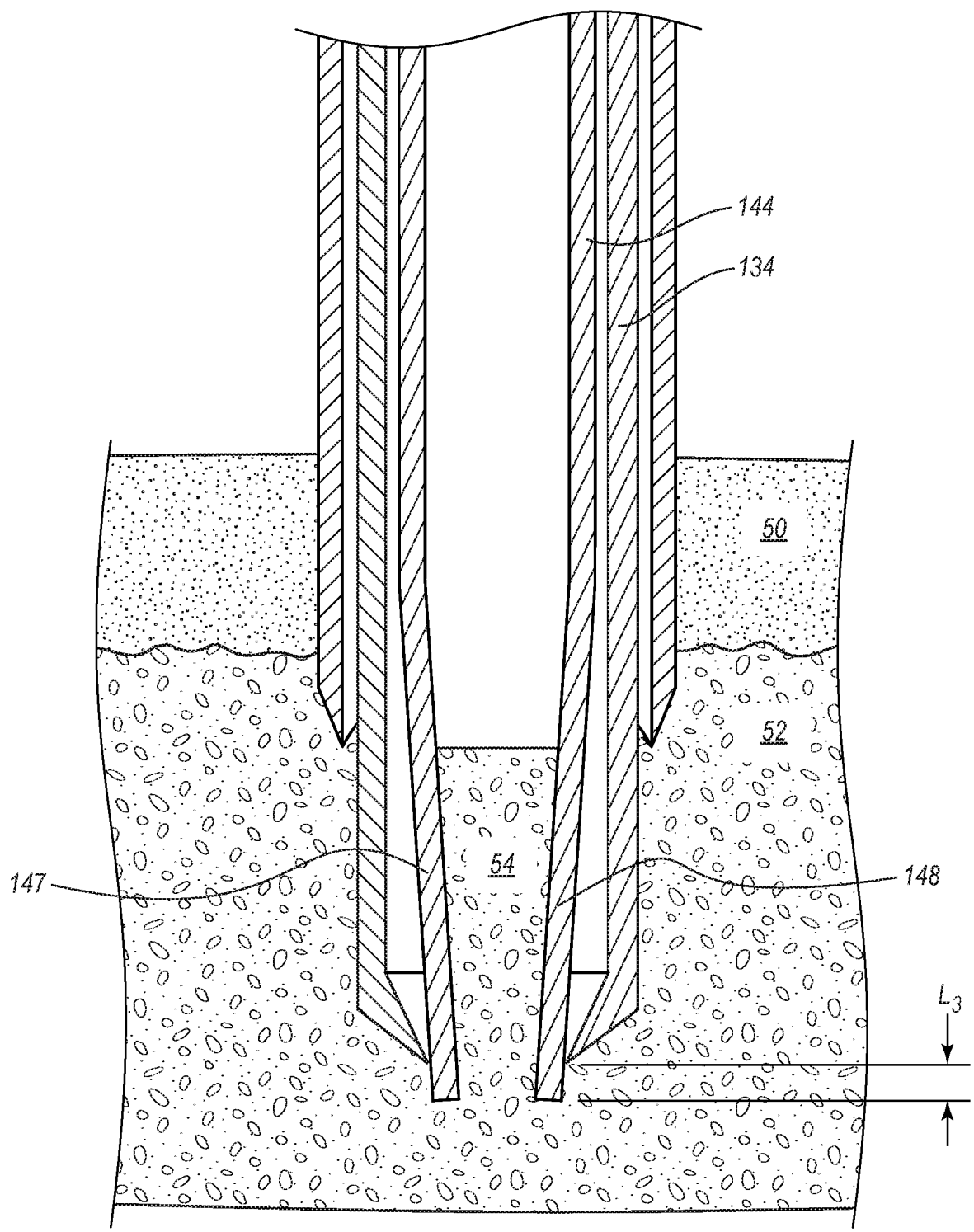
FIG. 5E is a cross-sectional view of the distal end of the portion of the system of FIG. 1 during a subsequent stage of the illustrative method, wherein the distal tip of the coring cannula has finished cutting through the marrow of the bone, and wherein the distal tip of the sample extraction cannula is advanced through the distal tip of the coring cannula and the sample extraction cannula is rotated to break the core from the adjacent bone marrow.

The distal extraction tip 146 can include one or more arms 147, 148, which may be capable of moving inwardly, or deflecting, to a slightly contracted state (compare, e.g., FIGS. 5D and 5E). In other or further instances, the one or more arms 147, 148 may be capable of moving outwardly to a slightly expanded state. In some instances, the one or more arms may be resiliently flexible. In the illustrated embodiment, the extraction tip 146 includes two arms 147, 148, which may also be referred to as gripping arms, prongs, tines fingers, clamps, flaps, beams, grips, graspers, engagement elements, etc. The illustrated arms 147, 148 are formed by cutting two longitudinal slots into the distal end of the extraction cannula 144.

With reference to FIG. 5B, the cutting tip 126 can include any suitable cutting configuration. Similarly, the coring tip 136 can include any suitable cutting configuration. For example, one or more of the tips 126, 136 can include any suitable number or configuration of teeth, serrations, embedded cutting elements, and/or other cutting members. In some embodiments, at least an inner surface of the distal tip 136 of the coring cannula 134 can narrow slightly at a position beyond the distal tip 146 of the extraction cannula 144. Stated otherwise, a distal end of the coring cannula 134 can include an internal constriction. In some embodiments, the constriction of the coring tip 136 can define an inner diameter (e.g., a minimum inner diameter) that is identical, or substantially identical, to an inner diameter of the extraction cannula 144—in particular, that is identical or substantially identical to an inner diameter of the extraction tip 146 of the extraction cannula 144. The coring cannula 134 may also be referred to as a cutting cannula.

Figure 3:
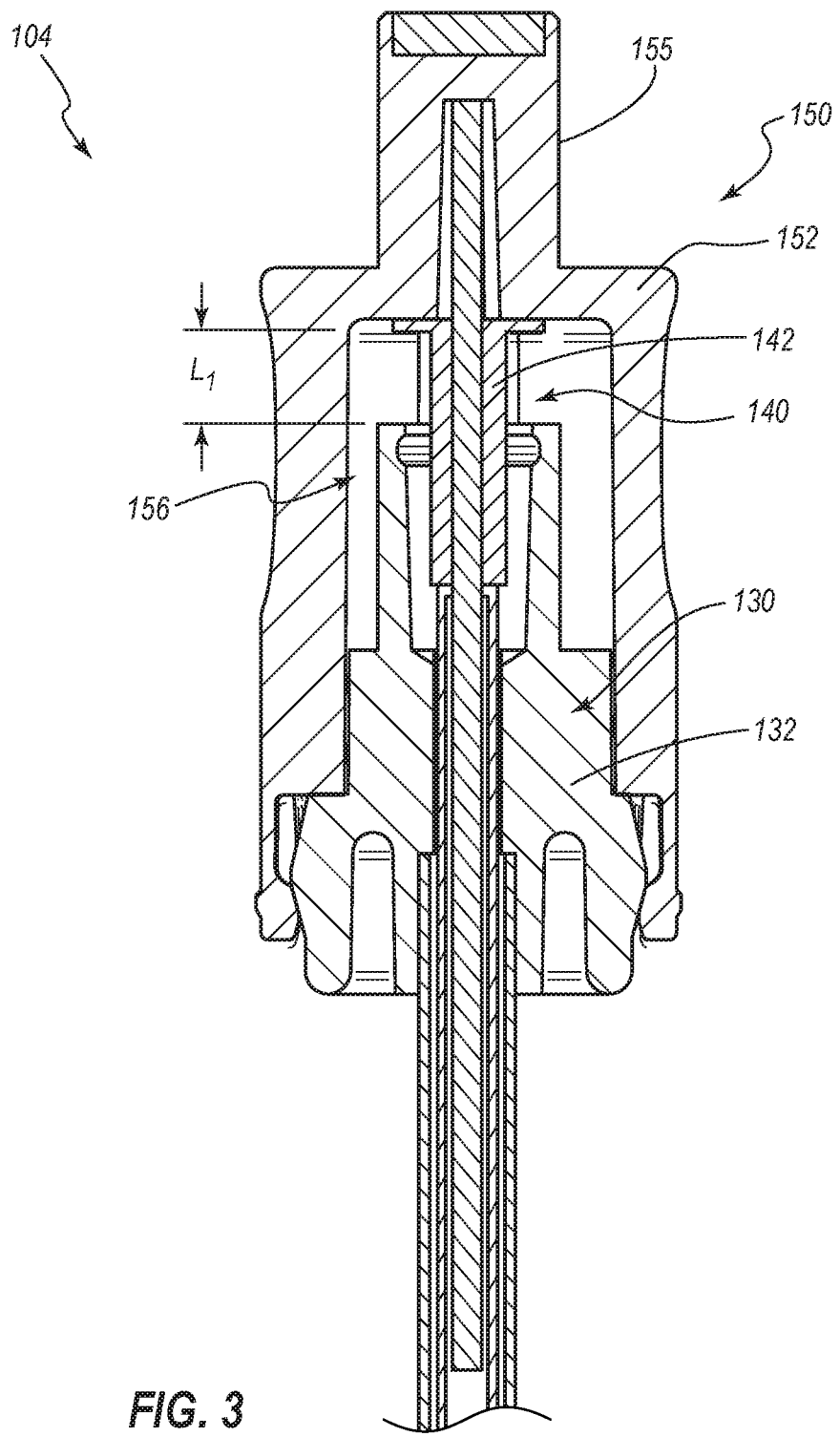
FIG. 3 is a cross-sectional view of a proximal portion of a coring and extraction assembly, which is another portion of the system of FIG. 1.

As depicted in a second style of broken lines in FIG. 1, and as depicted in FIG. 3, the stiffener assembly 150 can be inserted into both the extraction assembly 140 and the coring assembly 130, and the stiffener assembly 150 can be coupled to the coring assembly 130. Further, the extraction assembly 140 can be inserted into the coring assembly 130. Moreover, the assembled coring and extraction assembly 140 can be inserted into the cutting assembly 120 after the trocar assembly 110 has been removed therefrom, as further discussed below.

With continued reference to FIG. 1, the system 100 can further include a push rod 160. As depicted in a third style of broken lines, the push rod 160 can be inserted into the extraction assembly 140 after the extraction assembly 140 has been removed from the coring assembly 130 and after the stiffener assembly 150 has been removed from the extraction assembly 140.

With reference to FIG. 2, the hub 112 of the trocar assembly 110 can receive the hub 122 of the cutting assembly 120 therein. The hubs 112, 122 can define any suitable connection interface via which the hubs 112, 122 can be coupled together in a locked angular orientation. For example, an outer surface defined by a portion of the hub 122 can be keyed to fit within a complementarily shaped inner surface defined by a portion of the hub 112 (see also FIGS. 10A and 10C and their associated description). The keyed surfaces can lock the hubs 112, 122 in a fixed angular orientation such that rotation of the hub 112 achieves simultaneous rotation of the hub 122. The hub 112 can define a driver connector or connection interface at a proximal end thereof for coupling with a driver, such as, for example, a hex-shaped post 115 (see also FIG. 1). The driver may be of a manual variety, such as a handle that may be rotated or otherwise manipulated by hand, or may be of a powered variety, such as a power drill.

With reference to FIG. 3, the hub 152 of the stiffener assembly 150 can receive therein the hubs 142, 132 of the extraction assembly 140 and the coring assembly 130, respectively. The hubs 152, 132 can define any suitable connection interface via which the hubs 152, 132 can be coupled together in a locked angular orientation. For example, an outer surface defined by a portion of the hub 132 can be keyed to fit within a complementarily shaped inner surface defined by a portion of the hub 152. The keyed surfaces can lock the hubs 152, 132 in a fixed angular orientation such that rotation of the hub 152 achieves simultaneous rotation of the hub 132. The hub 152 can define a connection interface at a proximal end thereof for coupling with a driver, such as, for example, a hex-shaped post 155 (see also FIG. 1). The driver may be of a manual variety, such as a handle that may be rotated or otherwise manipulated by hand, or may be of a powered variety, such as a power drill.

The hub 152 can further define a cavity 156 within which the hub 142 can move freely. In particular, the hub 142 can be configured to rotate freely relative to the hub 152. More generally, the extraction assembly 140 can be configured to rotate freely relative to both the stiffener assembly 150 and the coring assembly 130. As discussed further below, this ability to freely rotate can permit the extraction assembly 140 to remain rotationally stationary while the stiffener assembly 150 and the coring assembly 130 are rotating in unison during manual or powered drilling into bone marrow. In some embodiments, an upper surface of the hub 142 may contact the hub 152 at an upper end of the cavity 156 during the rotation. In some embodiments, the hub 152 and/or the hub 142 may include a friction-reducing material and/or have a friction-reducing coating or other layer disposed thereon. For example, in some embodiments, Delrin® may be used.

As shown in FIG. 3, the cavity 156 can be sufficiently large to permit a contact surface (e.g., an outwardly extending flange) of the hub 142 to extend above a contact surface (e.g., a top end) of the hub 132 by a distance $L_1$. With reference to FIG. 5B, the distal tip 146 of the extraction cannula 144 can be recessed relative to the distal tip 136 of the coring cannula 134 by a distance $L_2$ when the coring and extraction assembly 104 is in a pre-use state, or prior to drilling into marrow. With reference to FIG. 5E, at a later stage of use, the hub 142 may be pressed downward toward the hub 132 to cause the distal tip 146 of the extraction cannula 144 to extend distally past the distal tip 136 of the coring cannula 134 by a distance $L_3$. Accordingly, the distance $L_1$ can desirably be at least as great as the distance $L_2+L_3$.

Figure 4:
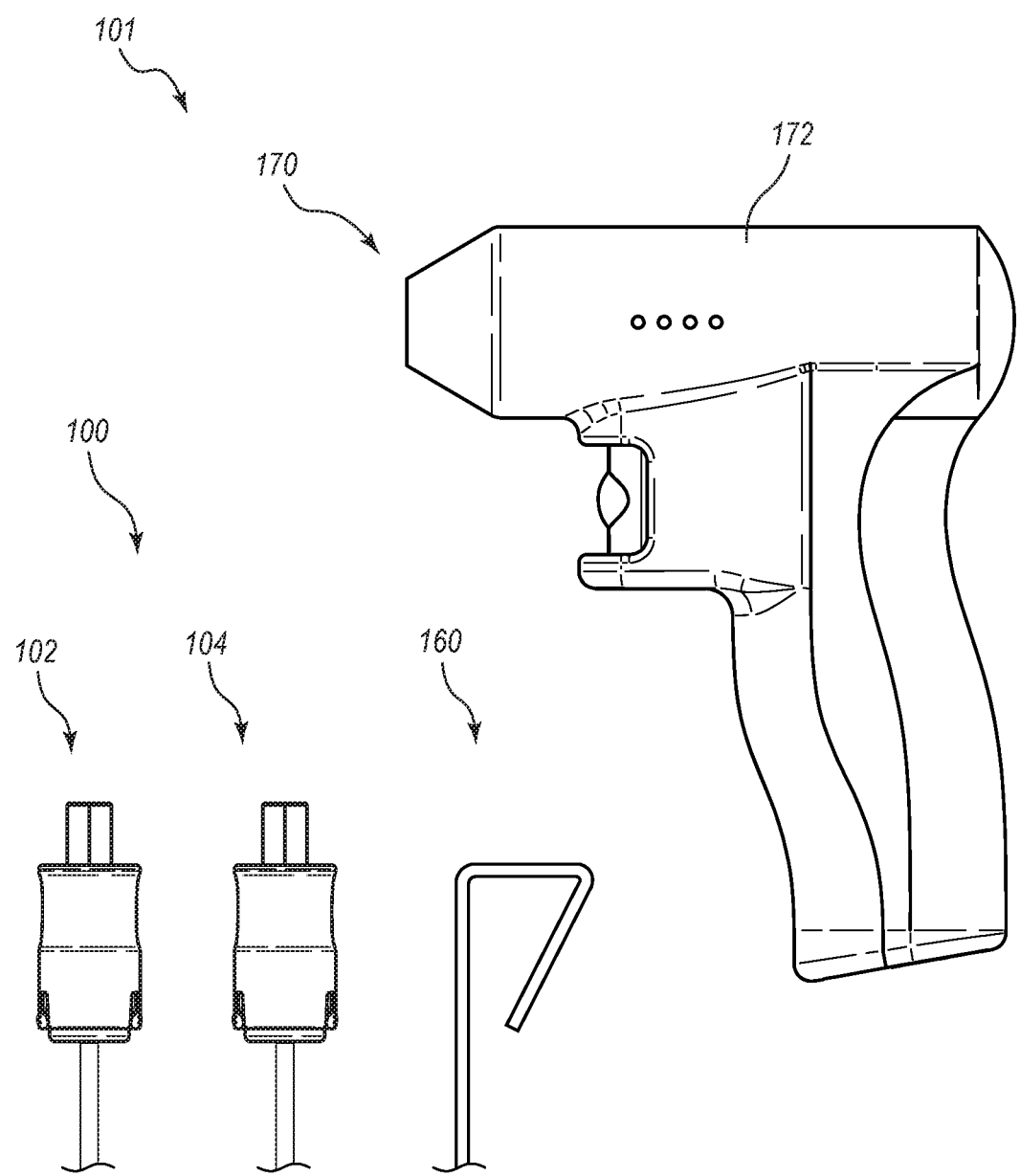
FIG. 4 is an elevation view of a further embodiment of a bone biopsy system that includes the system of FIG. 1 and additionally includes a driver configured to couple with portions of the system.

With reference to FIG. 4, in some embodiments, a bone biopsy system 101 can include not only the system 100 just described, but also a driver 170. The driver 170 can be selectively and individually coupled with each of the cortical drilling assembly 102 and the coring and extraction assembly 104. In particular, the driver 170 can be configured to selectively couple with the connection interfaces at the proximal ends of the hubs 112, 152, as previously described. Any suitable driver 170 is contemplated. For example, in some embodiments the driver 170 can comprise a handle that can be manually operated by a user (e.g., manipulated)

for manual insertion of the assemblies 102, 104 into bone. In the illustrated embodiment, the driver 170 comprises a handheld power drill 172, which can achieve powered insertion of the assemblies 102, 104 into bone.

Illustrative examples of methods of using the system 100 will now be described. Where a particular drawing is not specified, the figures may be referenced generally.

With reference to FIG. 5A, in some methods, the cortical drilling assembly 102 (which may also be referred to as a cortical cutting assembly or as a marrow access assembly) is coupled to the drill 172 and is drilled into a bone 51 of a patient. The trocar 114 and the cutting cannula 124 can each cut through the cortical layer 50 of the bone to reach the marrow 52 of the bone. In the stage of the method depicted in FIG. 5A, a portion of the distal tip 116 of the trocar 114 has passed through the cortical layer 50 into the marrow 52, whereas the remainder of the distal tip 116 of the trocar 114 and the distal tip 126 of the cutting cannula 124 continue to cut through the cortical layer 50.

The cortical drilling assembly 102 can continue to cut deeper into the bone 51 until the distal tip 126 of the cutting cannula 124 passes through the cortical layer 50 (see FIG. 5B) of the bone. Thus, the distal cutting tip 126 of the cutting cannula 124 can be positioned within the marrow 52 (see FIG. 5B) of the bone. The drill is decoupled and removed from the cortical drilling assembly 102—specifically, is decoupled from the trocar hub 112. The trocar assembly 110 is decoupled and removed from the cortical cutting assembly 120 as the cortical cutting assembly 120 is left in place in the bone 51.

After the trocar assembly 110 has been removed from the cortical cutting assembly 120, the coring and extraction assembly 104 is used to obtain a sample of the marrow 52 via—e.g., by passing through—the cortical cutting assembly 120. In particular, the distal end of the coring and extraction assembly 104 is inserted through each of the hub 120 and the cutting cannula 124 of the cutting assembly 120 while the cutting assembly 120 remains positioned within the bone 51. The drill 172 is coupled with the coring and extraction assembly 104 before, during, or after insertion of the coring and extraction assembly 104 through the cortical cutting assembly 120.

FIG. 5B depicts a point in time just before the drill 172 is actuated to rotate the coring and extraction assembly 104. Actuation of the drill rotates the coring and extraction assembly 104. The cutting cannula 124 remains stationary and engaged within the bone 51 during this rotation. That is, the cutting cannula 124 can define an inner diameter that is sufficiently larger than an outer diameter of the coring cannula 134 to avoid frictional engagement of sufficient strength to achieve rotation of the cutting cannula 124. While spinning, the coring and extraction assembly 104 is advanced distally to core the marrow 52.

With reference to FIG. 5C, as the coring and extraction assembly 104 continues to rotate and be advanced distally, the coring tip 136 eventually comes into contact with the marrow 52 and begins coring a sample 54 therefrom. The sample 54 may also be referred to as a core, specimen, etc. An outer diameter of the sample 54 is the same as the inner diameter of the coring tip 136.

With reference to FIG. 5D, as the coring and extraction assembly 104 continues to rotate and be advanced distally, the coring tip 136 continues to core the sample 54 from the marrow 52. That is, the sample 54 grows in size and is advanced proximally into the coring and extraction assembly 104. Stated otherwise, distal advancement of the coring and extraction assembly 104 positions the growing sample 54 deeper within the coring and extraction assembly 104. Eventually, the sample 54 is advanced proximally by a sufficient amount to enter into the extraction cannula 144. Again, the outer diameter of the sample 54 is the same or substantially the same as the inner diameter of the coring tip 136, which is the same or substantially the same as the inner diameter of the extraction cannula 144. Contact between the sample 54 and the inner wall of the extraction cannula 144 can cause the extraction cannula 144 to stop spinning. Thus, the extraction cannula 144 can be rotationally fixed relative to the sample 54 while the remainder of the coring and extraction assembly 104 continues to rotate for further coring. Stated otherwise, because the extraction cannula 144 has rotational freedom relative to the remainder of the coring and extraction assembly 104, the extraction cannula 144 can engage the sample 54 and not rotate relative thereto. Thus, the structural integrity of the sample 54 can be maintained.

As the coring and extraction assembly 104 is distally advanced further, the sample 54 can advance (e.g., slide) deeper (e.g., more proximally) into the extraction cannula 144 and can be held thereby. The proximal advancement in this manner can proceed smoothly, due to the approximate size match of the sample diameter 54 and the inner diameter of the extraction cannula 144. Eventually, a desired size of the sample 54 is achieved and drilling discontinues.

With reference to FIGS. 3 and 4, the drill 172 is decoupled from the coring and extraction assembly 104. The stiffener assembly 150 is then removed. This leaves the hub 142 of the extraction assembly 140 exposed. The hub 142 is then depressed (i.e., advanced distally) into close proximity to or contact with the proximal end of the hub 132.

With reference to FIG. 5E, as the extraction cannula 144 is thus advanced distally relative to the coring cannula 134, the distal tip of the extraction cannula (which includes the deformable arms 147, 148) is advanced through the narrowed or constricted opening defined by the distal tip of the coring cannula 134. The narrowed or constricted arrangement corresponds with the property of the inner diameter being approximately the same as the inner diameter of the extraction cannula 144, as previously discussed.

The arms 147, 148 can deflect or compress inwardly slightly as they are advanced past the distal tip of the coring cannula 134. This effect may, for some embodiments, be exaggerated in the depiction shown in FIG. 5E. Accordingly, the arms 147, 148 can press inwardly on the sample 54 and can thereby increase a grip on the sample 54. The hub 142 can be rotated relative to the hub 132, which effects rotation of the extraction cannula 144 relative to the coring cannula 134 and the body of marrow 52 that surrounds the coring cannula 134. The arms 147, 148 can remain in their inwardly deflected state during such rotation, and thus can maintain their grip on the sample 54. Stated otherwise, as the extraction cannula 144 is rotated relative to the coring cannula 134, the inwardly projecting distal tip 136 of the coring cannula 134 can maintain the arms 147, 148 in their inwardly deflected state such that the arms 147,148 remain in gripping contact with the sample 54. Such rotation of the extraction cannula 144 can break or otherwise sever or separate the sample 54 from the body of the marrow 52.

Figure 5F:
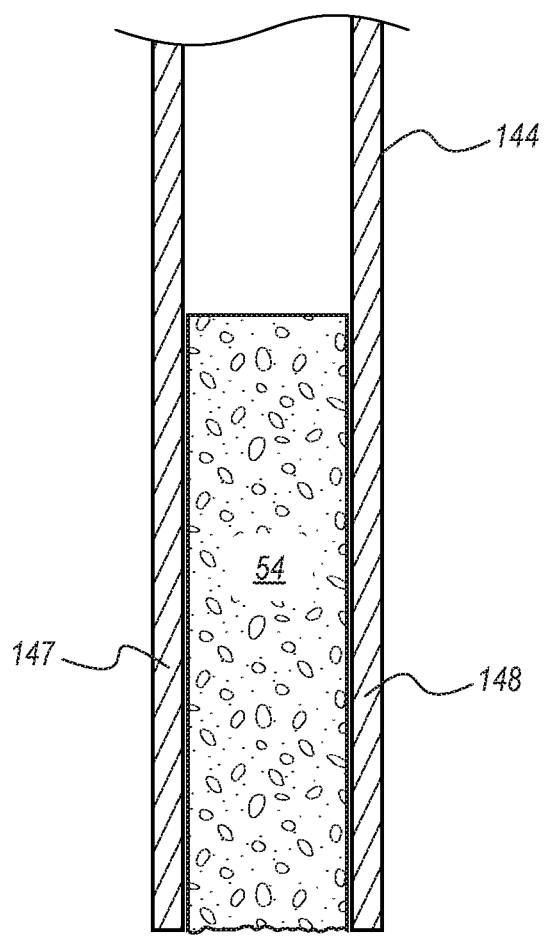
FIG. 5F is a cross-sectional view depicting another stage of the method in which the core has been obtained and is being held by the sample extraction cannula, and in which the sample extraction cannula has been removed from the cutting cannula and from the coring cannula.
Figure 5G:
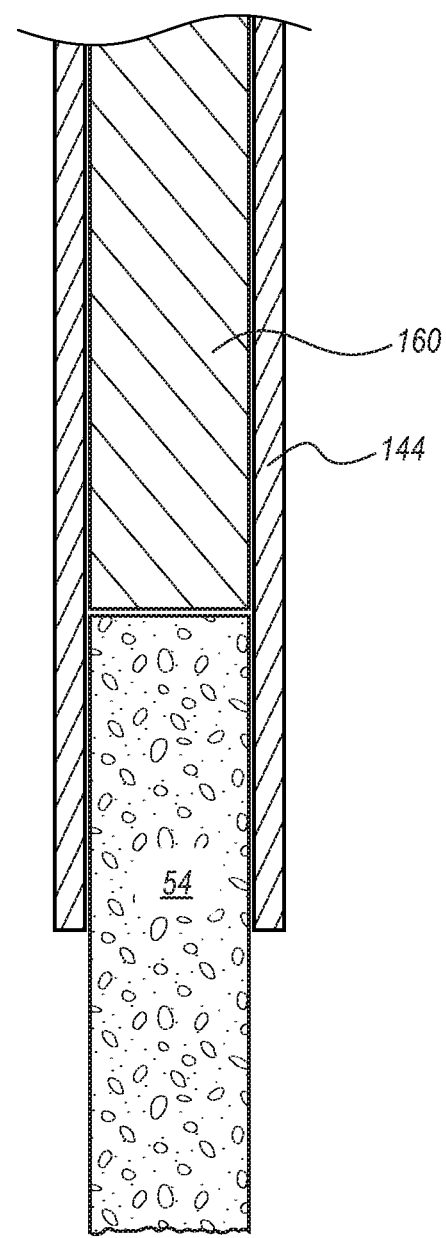
FIG. 5G is a cross-sectional view depicting the core being pushed from the sample extraction cannula.

With reference to FIG. 5F, the cutting assembly 120, the coring assembly 130, and the extraction assembly 140 can be removed from the patient (whether in unison or serially). The extraction assembly 140 can be removed from the coring assembly 130. The push rod 160 can then be inserted through a channel through the hub 142, through the extraction cannula 144, and into contact with a proximal end of the sample 54. The push rod 160 is advanced distally to push the sample 54 through the distal end of the extraction cannula 144.

As previously discussed, the arms 147, 148 may be flexible or readily deformable, such that the arms 147, 148 exert only a loose grip on the sample 54 at this stage. As the sample 54 is pushed past the arms 147, 148, the arms 147, 148 may, in some embodiments, expand or otherwise deform to permit ready passage thereby of the sample 54. In other instances, the arms 147, 148 remain in a natural or unflexed state as the sample 54 is pushed past the arms 147, 148. The sample 54 may thus be provided from the system with a high diagnostic yield.

Figure 6:
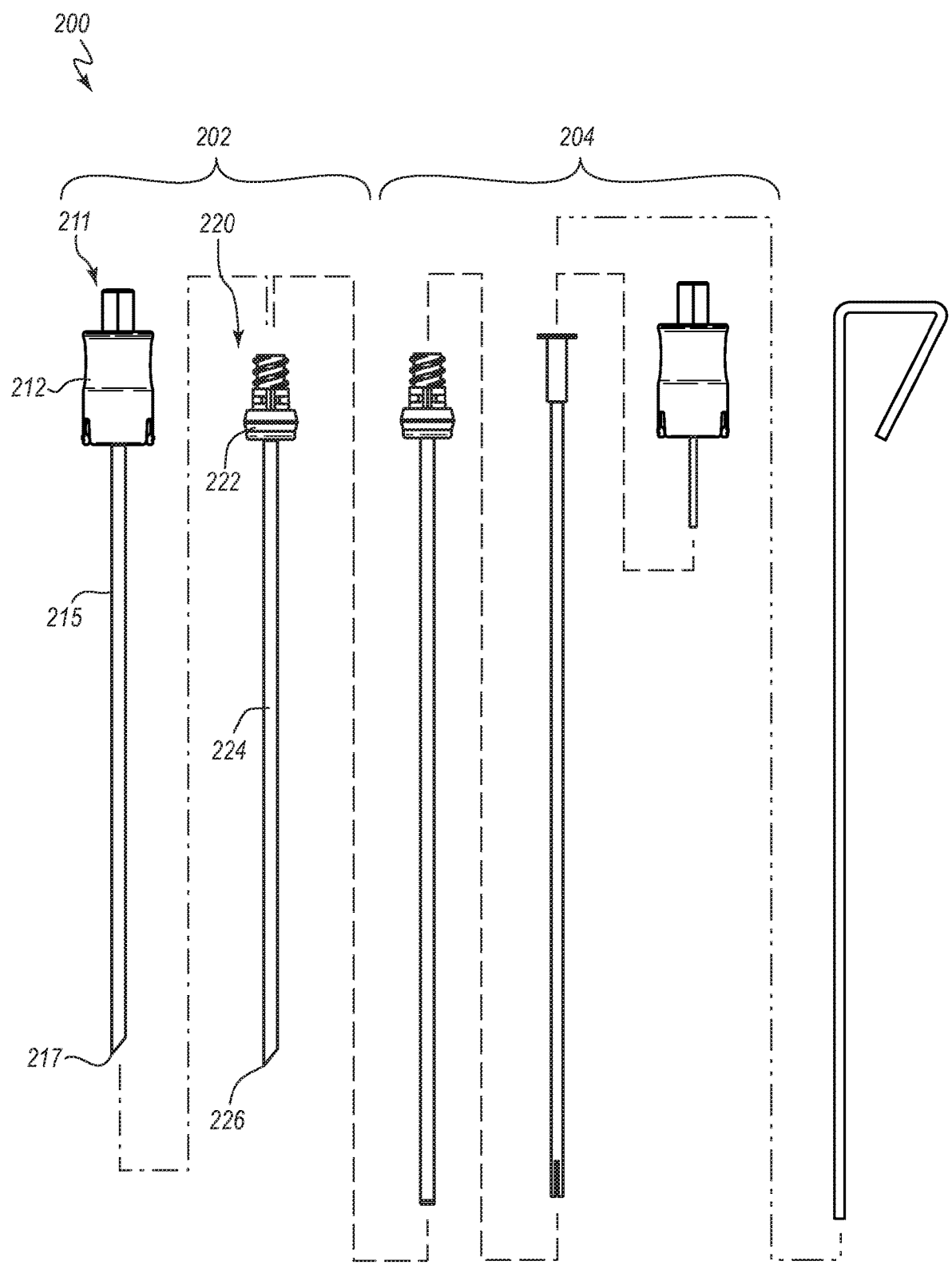
FIG. 6 is an elevation view of another embodiment of a bone biopsy system that includes a cortical drilling assembly that includes an embodiment of a cutting needle and an embodiment of an obturator.

FIG. 6 depicts another embodiment of a bone biopsy system 200 that can resemble the system 100 discussed above in many respects. The system 200 can resemble the system 100 described above in certain respects. Accordingly, like features are generally, although not necessarily exclusively, designated with like reference numerals, with the leading digits incremented to "2." Relevant disclosure set forth above regarding similar features (e.g., features identified by similarly reference numerals) thus may not be repeated hereafter. Moreover, specific features of the system 200 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the system 200. Any suitable combination of the features and variations of the same described with respect to the system 100 can be employed with the system 200, and vice versa. This pattern of disclosure applies equally to further embodiments depicted in subsequent figures and described hereafter, wherein the leading digits may be further incremented.

The system 200 includes a cortical drilling assembly 202 that differs from the cortical drilling assembly 102. In particular, the cortical drilling assembly 202 includes an obturator assembly 211 and a cutting assembly 220. The cutting assembly 220 includes a cutting cannula 224 that includes a distal cutting tip 226. The cutting cannula 224 may also be referred to as a cutting needle. For example, the cutting tip 226 can have a needle-like arrangement. In the illustrated embodiment, the cutting tip 226 is formed as a simple bias grind. Other arrangements are contemplated.

The obturator assembly 211 can include an obturator 215 and a distal obturator tip 217. In some embodiments, the obturator 215 is configured to fill the lumen of the cutting cannula 224 to prevent material from entering the cutting cannula 224—for example, the obturator 215 may prevent clogging or other undesired presence of cutting debris. In some embodiments, the distal tip 217 does not include any cutting surfaces. The tip 217 may be configured to sit flush with or slightly recessed relative to the bevel of the cutting tip 226.

The system 200 can further include a coring and extraction assembly 204. In some embodiments, the coring and extraction assembly 204 can be substantially identical to the coring and extraction assembly 104 described above, and may be used with the cortical drilling assembly 202 in manners such as those previously described with respect to the cortical drilling assembly 102.

Further illustrative examples and descriptions of various embodiments, such as those depicted in the previously described figures, are provided hereafter. The reference numerals identified hereafter correspond to the like-numbered features identified in FIGS. 1-6.

A cortex drilling system 102 can be comprised of a sharp cortex cutting cannula 124 affixed to a hub 122, and an inner obturator 114 affixed to a drive hub 112. A bone marrow coring system 104 can be comprised of a marrow cutting cannula 136 fixedly attached to a hub 132, an extraction cannula 144 with a passive, non-coupled hub 142, and a drive hub 150 fixedly attached with a stiffening rod 154 that partially extends down the length of the extraction cannula 144. The cortex drilling system 102 can have the inner obturator 114 removed, and the marrow coring system 104 can be introduced into the cortex cutting cannula 124.

A bone marrow system 100 for accessing and extracting bone marrow can be provided. A cortex drilling needle system 102 is comprised of a cortex cutting cannula 124 coupled to an obturator 114, which can be engaged with a drill coupling, by virtue of mating features of the drill coupling and of a cortex drive hub 112. The obturator 114 can be removed from the cortex cutting cannula 124 and replaced with the marrow coring system 104, and can further be disconnected from the drill coupling. The marrow coring system 104 is significantly longer than the cortex cutting cannula 124. The marrow coring system 104, can be engaged with the drill coupling by virtue of the mating features of the drill and the marrow drive coupling 152.

A bone biopsy system 100, 200 can include a powered drill or manual drill, a cortex drilling needle or cannula system 102, 202, and a bone marrow coring and extraction system 104, 204. The cortex drilling system 102, 202 provides access from outside the bone, through the bone cortex, to the margin of the bone marrow, and is comprised of a sharp cutting feature at the distal end of a cannula 124, 224 attached to the cortex cannula hub 122, 222, and an inner member with a drive hub 112, 212 coupled to the cortex cannula hub 122, 222, such that the drive hub and the cortex cannula hub rotate together. After access through the cortex has been achieved, the inner member 124, 224 is removed from the cortex drilling cannula and replaced with the bone marrow coring system 104, 204. The bone marrow coring system 104, 204 is comprised of a marrow cutting cannula 134, 234 fixedly attached to a hub 132, 232, an extraction cannula 144, 244 with a passive hub 142, 242, and a drive socket 152, 252 fixedly attached with a stiffening rod 154, 254 that partially extends down the length of the extraction cannula 134, 234. The marrow cutting cannula has cutting teeth disposed at the distal end.

The marrow cutting cannula can be constructed with a reduced diameter such that the marrow core diameter is the same or less than the diameter of the extraction cannula. The bone marrow coring system takes a core sample of the marrow by being drilled into the marrow either manually or by power drill. The extraction cannula is not rotationally fixed and is therefore not required to rotate with the thin cutting cannula or the drive socket with stiffening rod. The extraction cannula is constructed with one or several slots that are cut axially from the most distal surface towards the proximal surface, creating two or more flexible beams or gripping arms. After the marrow coring system has drilled a core, the extraction cannula is pushed forward into the narrow part of the distal tip of the marrow cutting cannula, collapsing the gripping arms. The system is then twisted to break off the bone marrow at the distal end, and the extraction cannula is removed from the marrow coring cannula, and the core sample is pushed out of the extraction cannula.

Figure 7:
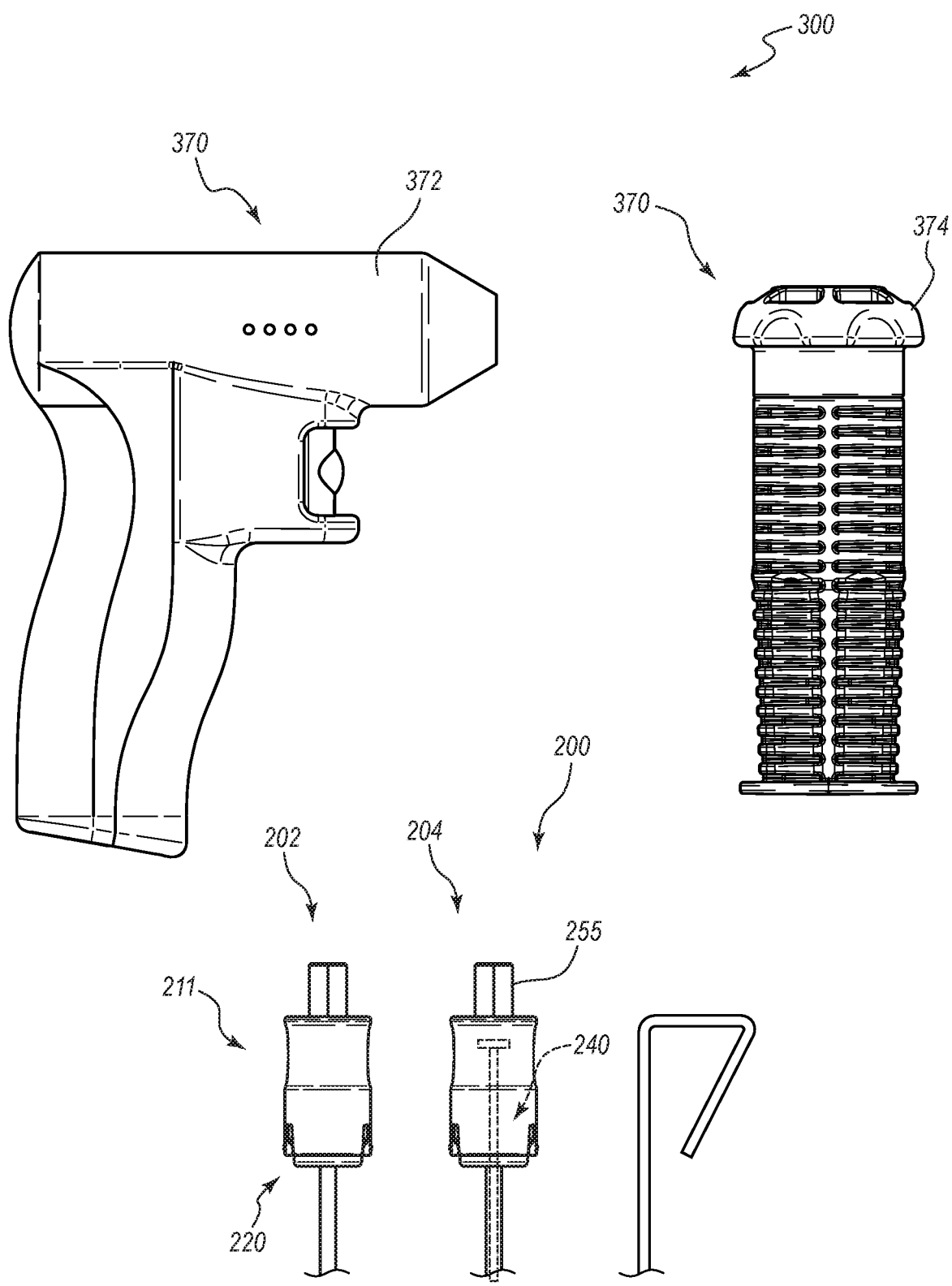
FIG. 7 is an elevation view of another embodiment of a bone biopsy system that includes the system of FIG. 6 and additionally includes a powered driver configured to couple with a cortical drilling portion thereof and a manual driver configured to couple with a coring and extraction portion thereof.

FIG. 7 depicts another embodiment of a bone biopsy system 300 that can resemble other systems disclosed herein. The system 300 includes an embodiment of the bone biopsy system 200 described above and a pair of drivers 370. In particular, the system 300 includes a powered driver 372, such as an electrically powered drill, and further includes a manual driver 374. In the illustrated embodiment, the manual driver 374 comprises a handle that is manipulable by a hand of a user, as discussed further below. In other embodiments, the bone biopsy system 100 can be used in place of the bone biopsy system 200.

When the system 300 is used for a bone biopsy, the powered driver 372 is coupled with the cortical drilling assembly 202 and is used to rotate the cortical drilling assembly 202 into the bone of a patient, as previously described. Once the cutting assembly 220 is secured in the bone so as to provide access to the marrow, the obturator assembly 211 is removed, such as in the manner described above with respect to the trocar assembly 110.

The manual driver 374 can be coupled with the coring and extraction assembly 250. In particular, the manual driver 374 can be coupled with the coring and extraction assembly 204 in a rotationally fixed manner, such that rotation of the manual driver 374 in either or both directions (e.g., clockwise and/or counterclockwise) effects like rotation of the coring and extraction assembly 250.

The coring and extraction assembly 204 is inserted through the cutting assembly 220 in manners such as previously discussed with respect to the cutting assembly 120. The user then rotates the manual driver 374 in any suitable manner to create a core sample from the marrow, which core sample is retained within a distal end of an extraction assembly 240. In particular, the user may rotate the manual driver 374 in a single direction (only clockwise or only counterclockwise), while pressing distally on the manual driver 374 to core the marrow. Alternatively or additionally, the user may rotate the manual driver 374 back and forth in opposite directions (clockwise and counterclockwise) while pressing distally on the manual driver 374 to core the marrow.

The system 300 thus employs both the powered driver 372 to drill through the cortical layer of bone and achieve access to the marrow and the manual driver 374 to core the marrow. In other embodiments, the manual driver 374 may be used with the cortical drilling assembly 202 to drill through the cortical layer of the bone, whereas the powered driver 372 may be used with the coring and extraction assembly 204 to form and extract a core sample from the marrow. In still other embodiments, the system 300 employs only the manual driver 374. That is, the manual driver 374 can be individually coupled with the cortical drilling assembly 202 to cut through the cortical layer of the bone, and is subsequently coupled with the coring and extraction assembly 204 to form and extract a core sample from the marrow.

Figure 8:
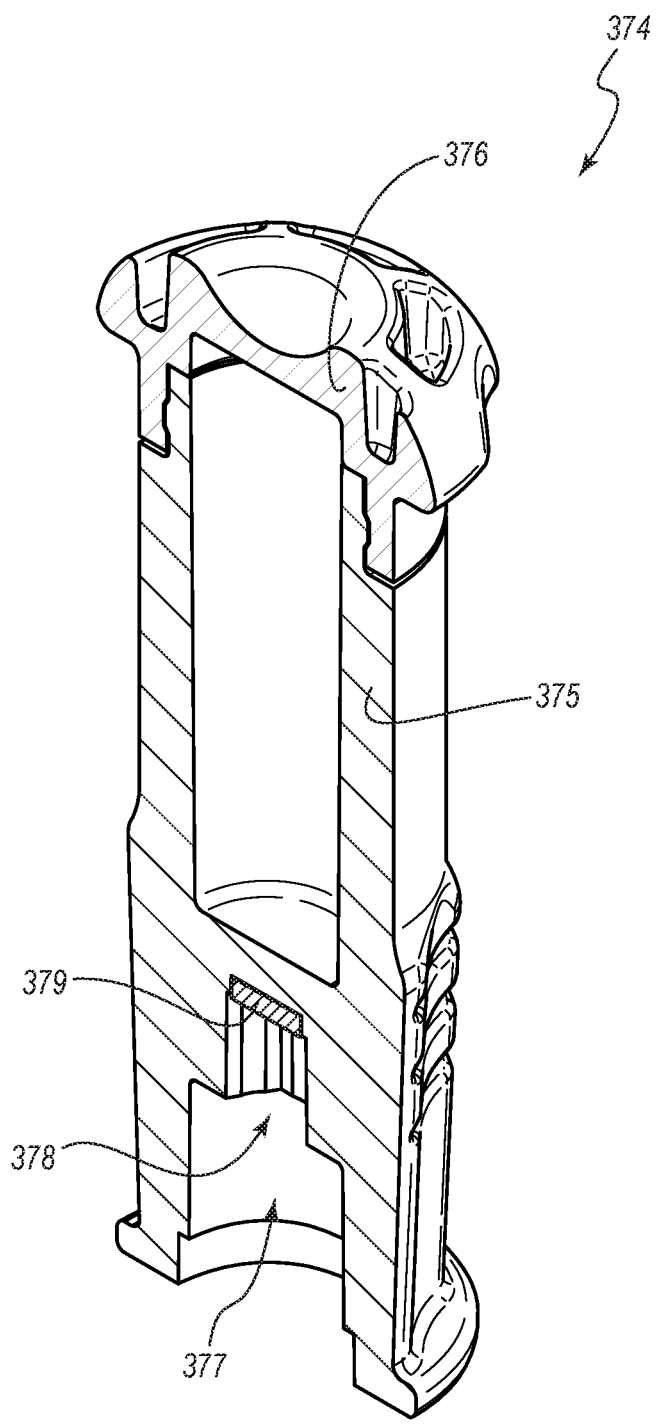
FIG. 8 is a cross-sectional view of the manual driver of FIG. 7.

With reference to FIG. 8, the illustrated manual driver 374 includes a body 375 and a cap 376. The body 375 may also be referred to as a handle, grip, etc. The cap 376 may also be referred to as a head, crown, abutment member, etc. The body 375 and/or the cap 376 may be ergonomically shaped for ready gripping and manipulation by the hand of a user. In the illustrated embodiment, the body 375 and the cap 376 are secured together so as to permit little or no relative longitudinal movement, but are rotational relative to each other about a common axis of rotation. In some instances, a user may press distally on the cap 376 (e.g., with the palm of the hand), and the cap 376 may remain stationary relative to the hand (e.g., relative to the palm), while the user rotates the body 375 with the fingers of the same hand. In other instances, the amount of friction present between the cap 376 and the body 375 as the user presses distally on the hub 374 can inhibit or prevent rotational movement between the cap 376 and the body 375. For example, in some instances, a user may press distally on the cap 376 and may grip and rotate the body 375 while pushing the same distally to achieve drilling and/or coring via the handle 374, and the cap 376 and the body 375 may rotate in unison or nearly in unison due to frictional engagement therebetween.

In other embodiments, the body 375 and the cap 376 may be fixed relative to each other, and thus may not rotate relative to each other. For example, in some embodiments, the body 375 and the cap 376 may be integrally formed of a unitary piece of material. A user may rotate the entirety of the manual driver 374, or stated otherwise, all components or portions of the manual driver 374 may be rotationally fixed relative to each other so as to rotate in unison. In some instances, a user may press distally on the cap 376 and/or may grip and rotate the body 375 while pushing the same distally to achieve drilling and/or coring via the handle 374.

The body 375 can define a recess 377 within which a proximal end of the cortical drilling assembly 204 can be received. The body 375 can further define a connection interface 378 of any suitable variety for coupling with the cortical drilling assembly 204. In the illustrated embodiment, the connection interface 378 is a hex-shaped socket that is sized to snugly receive a hex-shaped stem 255 of the drilling assembly 204. The complementary socket 378 and stem 255 can engage one another to achieve a rotational lock, such that rotation of the body 375 yields concurrent or identical rotation of the drilling assembly 204.

In some embodiments, the manual driver 374 includes a magnetic member 379 at an upper end of the socket 378, which can interact with another magnetic member (not shown) at an upper end of the stem 255 of the drilling assembly 204. Such an arrangement can facilitate and or assist in maintaining a secure connection between the manual driver 374 and the drilling assembly 204.

Any other suitable arrangement or configuration of the manual driver 374 is contemplated. For example, in some embodiments, the body 375 of the manual driver 374 is shorter than depicted in the drawings.

Figure 9:
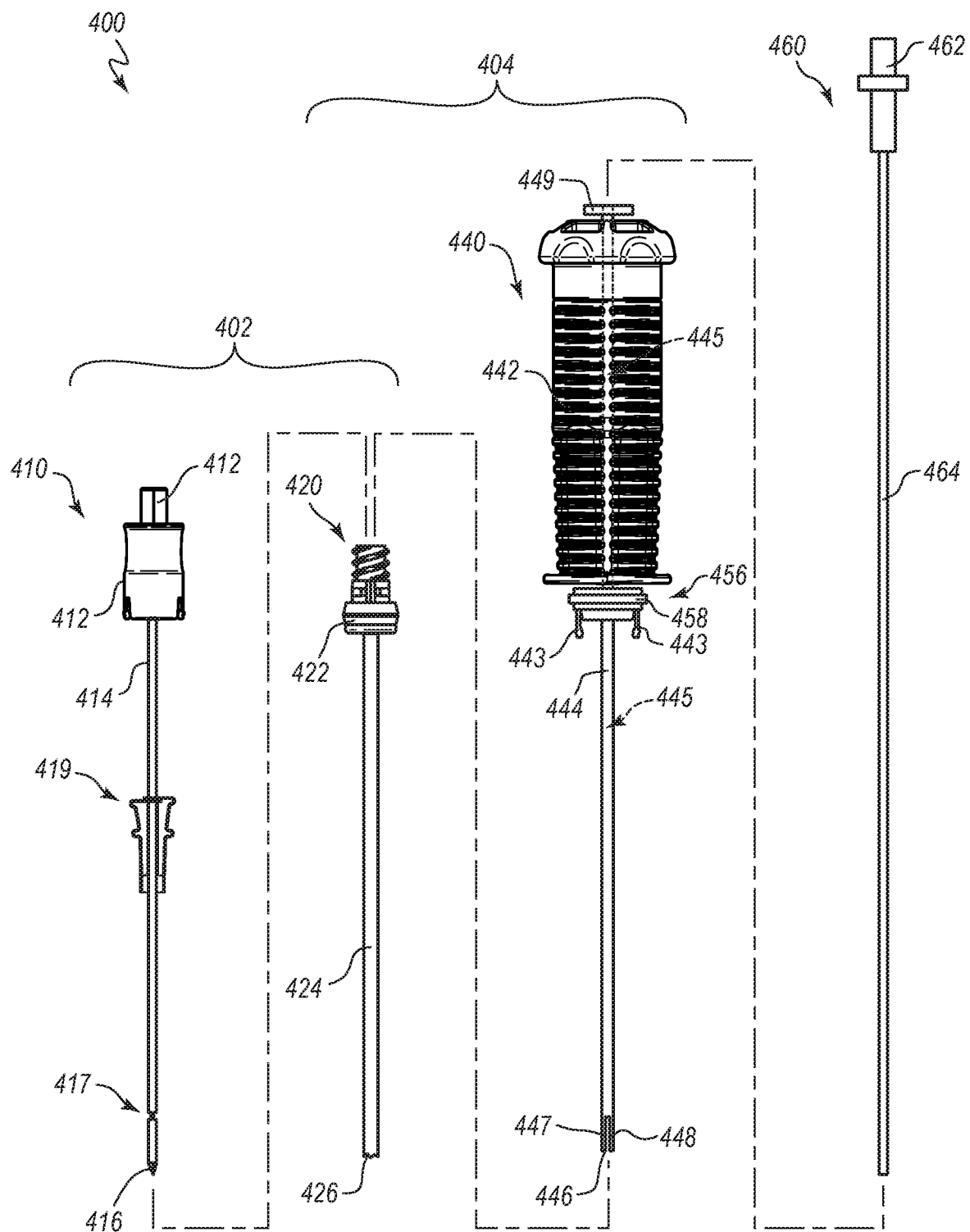
FIG. 9 is an elevation view of another embodiment of a bone biopsy system.

FIG. 9 depicts another embodiment of a bone biopsy system 400. The bone biopsy system 400 can resemble the bone biopsy systems 100, 200, 300 discussed above in many respects. However, rather than including a separate cutting and coring assemblies (such as, for example, the cutting assembly 120 and the coring assembly 130), the system 400 includes a single cutting assembly 420 that is used both for drilling through cortical bone and for coring marrow of the bone. Moreover the system 400 includes an extraction assembly 440 that includes a hub 442, which may also be referred to as a manual handle, that is preassembled to an extraction cannula 444, which may also be referred to as an extraction tube 444. The hub or handle 442 can be used for manual rotation of the cutting assembly 420 when coupled therewith, as discussed further below.

The system 400 includes a cortical drilling system 402 and a coring and extraction system 404. The cortical drilling system 402 includes a trocar assembly 410 and the cutting assembly 420, which can resemble the trocar assembly 110 and the cutting assembly 120 discussed above, respectively. In other embodiments, the cortical drilling system 402 can instead include an obturator assembly and a cutting assembly, such as the obturator assembly 211 and the cutting assembly 220 discussed above. For example, in some embodiments, the cutting cannula 424 can comprise a cutting needle, such as the needle 224 previously discussed with respect to the cutting assembly 220. As can be appreciated, in either case, the cortical drilling system 402 includes a cutting cannula 424 having a cutting tip 426 configured to cut through cortical bone. The cutting cannula 424 may also be referred to as a cutting tube or, for reasons discussed further below, as a coring cannula or tube.

In the illustrated embodiment, the trocar assembly 410 includes a trocar assembly hub 412, a trocar 414 fixedly secured to the hub 412, and a cutting tip 416 at a distal end of the trocar 414. In some embodiments, the trocar assembly 410 further includes a recess 417 near the cutting tip 416. The recess 417 may be of any suitable variety, such as, for example, an annular groove. The trocar assembly 410 can further include a safety shield 419, which can be configured to interact with the recess 417 to automatically lock onto a distal end of the trocar 414 to shield the cutting tip 416 when the trocar assembly 410 is removed from the cutting assembly 420, as described further below.

In the illustrated embodiment, the cutting assembly 420 includes a cutting assembly hub 422, the cutting cannula 424 fixedly secured to the hub 422, and the cutting tip 426 at the distal end of the cutting cannula 424. The cutting tip 426 is described in further detail below.

Figure 11:
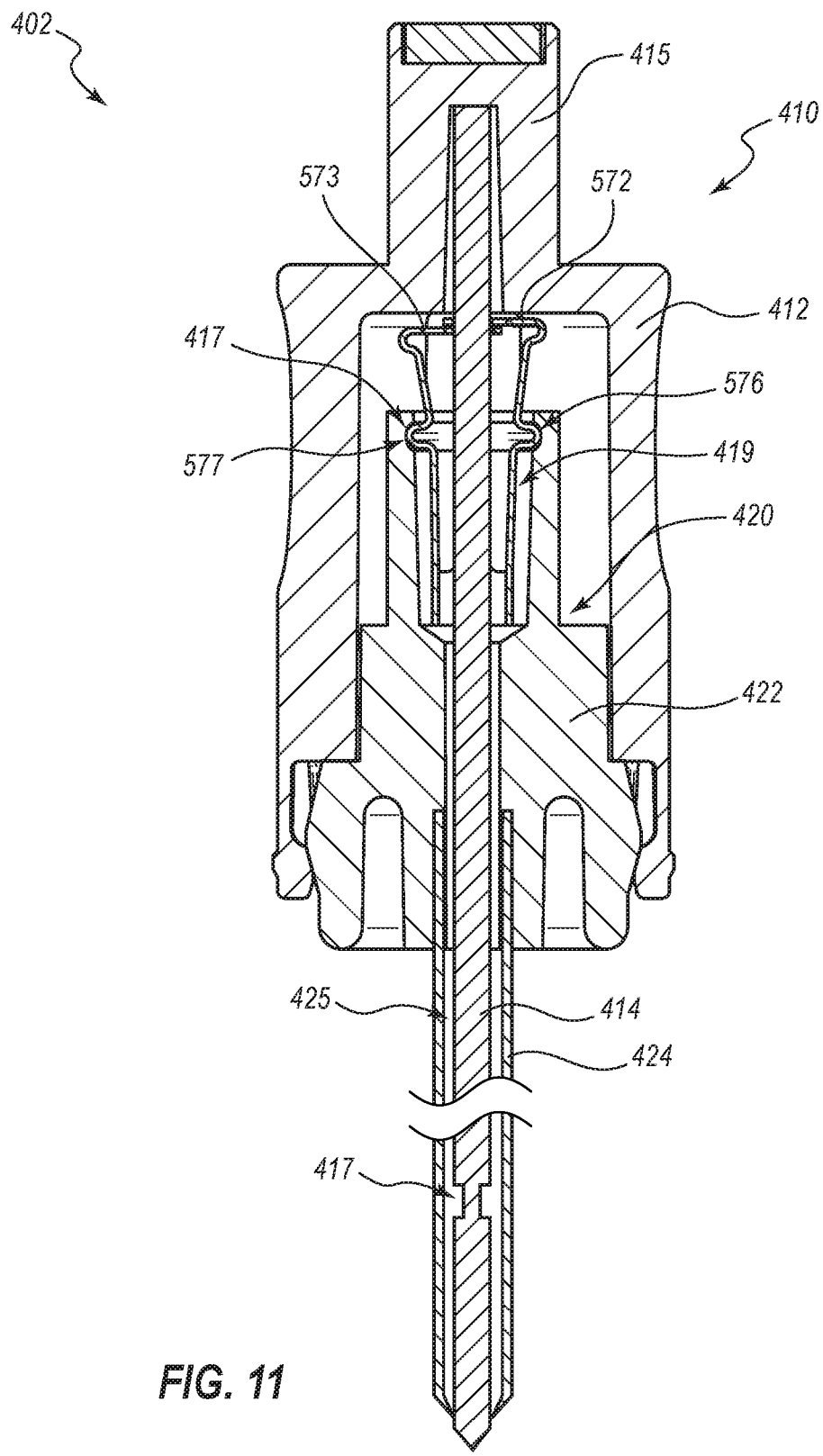
FIG. 11 is a cross-sectional view of a cortical drilling assembly, which is a portion of the system of FIG. 9.

As depicted in a first style of broken lines in FIG. 9, and as further depicted in FIG. 11, the trocar assembly 410 can be inserted into and coupled with the cutting assembly 420. In particular, the trocar assembly 410 can be coupled with the cutting assembly 420 in a rotationally fixed manner such that the trocar assembly 410 and the cutting assembly 420 can rotate in unison, such as when driven by a power drill or by a manual handle.

With continued reference to FIG. 9, the coring and extraction assembly 404 can include the cutting assembly 420, which may also be referred to as a coring assembly 420. That is, as further discussed below, the cutting assembly 420 is not only configured to cut cortical bone, but also thereafter to core out a marrow sample. The coring and extraction assembly 404 further includes an extraction assembly 440 that includes the extraction assembly hub 442 and an extraction cannula 444 that is coupled with the hub 442 so as to translate and rotate relative thereto, as further discussed below. The extraction cannula 444 includes an extraction tip 446 at a distal end thereof. The extraction tip 446 can include a plurality of arms 447, 448 such as the arms 147, 148 previously described.

The extraction cannula 444 can extend through a full length of the hub 442. Stated otherwise, a proximal end of the extraction cannula 444 extends proximally from a proximal end of the hub 442. The proximal end of the extraction cannula 444 can be coupled with an actuator 449 of any suitable variety. In the illustrated embodiment, the actuator 449 comprises a disk-shaped lateral extension that a user can depress to advance the extraction cannula 444 distally relative to the hub 442, as discussed further below. In particular, the user can press distally on the actuator 449 to urge the extraction cannula 444, which can urge the distal ends of the arms 447, 448 through the narrowed distal tip 426 of the cutting cannula 424. As discussed elsewhere herein, this movement of the arms 447, 448 through narrowed distal tip 426 can deflect the arms 447, 448 inwardly to press against a core sample to grip the sample.

Figure 13:
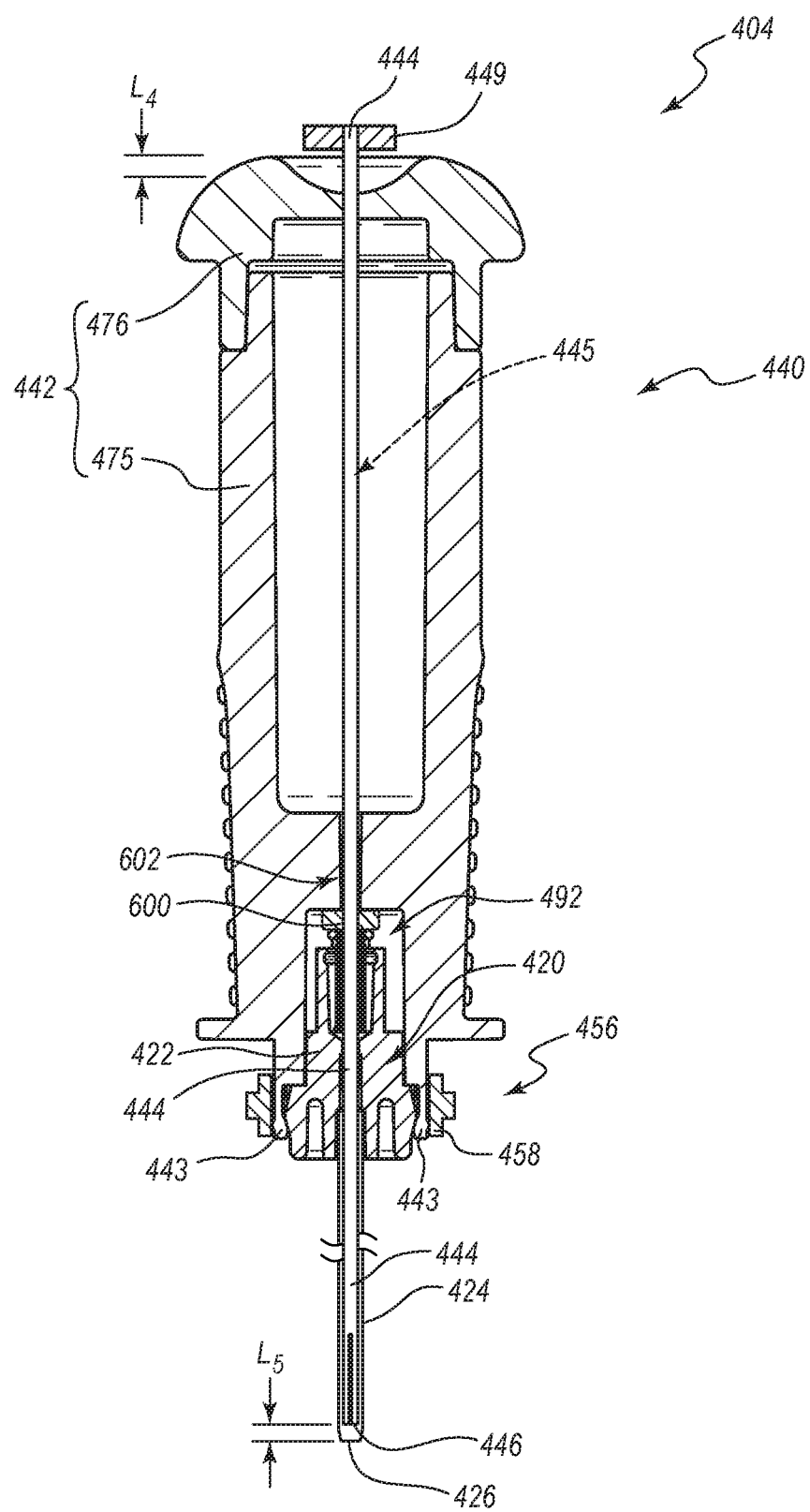
FIG. 13 is a cross-sectional view of a coring and extraction assembly, which is another portion of the system of FIG. 9.

In some embodiments, the extraction cannula 444 extends through the actuator 449. For example, as can be seen in FIG. 13, an upper tip of the extraction cannula 444 can be flush with an upper surface of the actuator 449. Any other suitable arrangement is contemplated. For example, in other embodiments, the upper tip of the extraction cannula 444 can be positioned at an interior of the actuator 449, and the actuator 449 can define a channel or passageway that extends from a proximal surface thereof and leads to a lumen 445 defined by the extraction cannula 444.

As depicted in a second style of broken lines in FIG. 9, and as depicted in FIG. 13, the extraction assembly 440 can be coupled to the cutting assembly 420 (which, again, may also be referred to as a coring assembly) after the trocar assembly 410 has been removed from the cutting assembly 420, as further discussed below. Thus, the trocar assembly 410 and the cutting assembly 420, when coupled together, form the cortical drilling assembly 402; similarly, the extraction assembly 440 and the cutting assembly 420, when coupled together, form the coring and extraction assembly 404. Operation of these assemblies is discussed further below.

With continued reference to FIGS. 9 and 13, in some embodiments, the coring and extraction assembly 404 includes a locking system or locking mechanism 456 that is configured to selectively lock the extraction assembly 404 to the cutting assembly 420. In the illustrated embodiment, the locking mechanism 456 includes a plurality of coupling arms 443 defined by the extraction assembly hub 442 that are configured to engage with a portion of the cutting assembly hub 422. The coupling arms 443 may be resiliently flexible and have inward protrusions that snap about the hub 422 in manners such as described below. In the illustrated embodiment, the locking mechanism 456 further includes a locking collar 458 that is selectively translatable relative to the hub 440, and in particular, can be translated distally or proximally relative to the arms 443. In the illustrated embodiment, the locking collar 458 is configured to deform when advanced distally over the arms 443 to prevent the arms 443 from flexing outwardly away from the hub 422 and to thereby lock the arms 443 relative to the hub 422, as discussed further below.

Figure 15A:
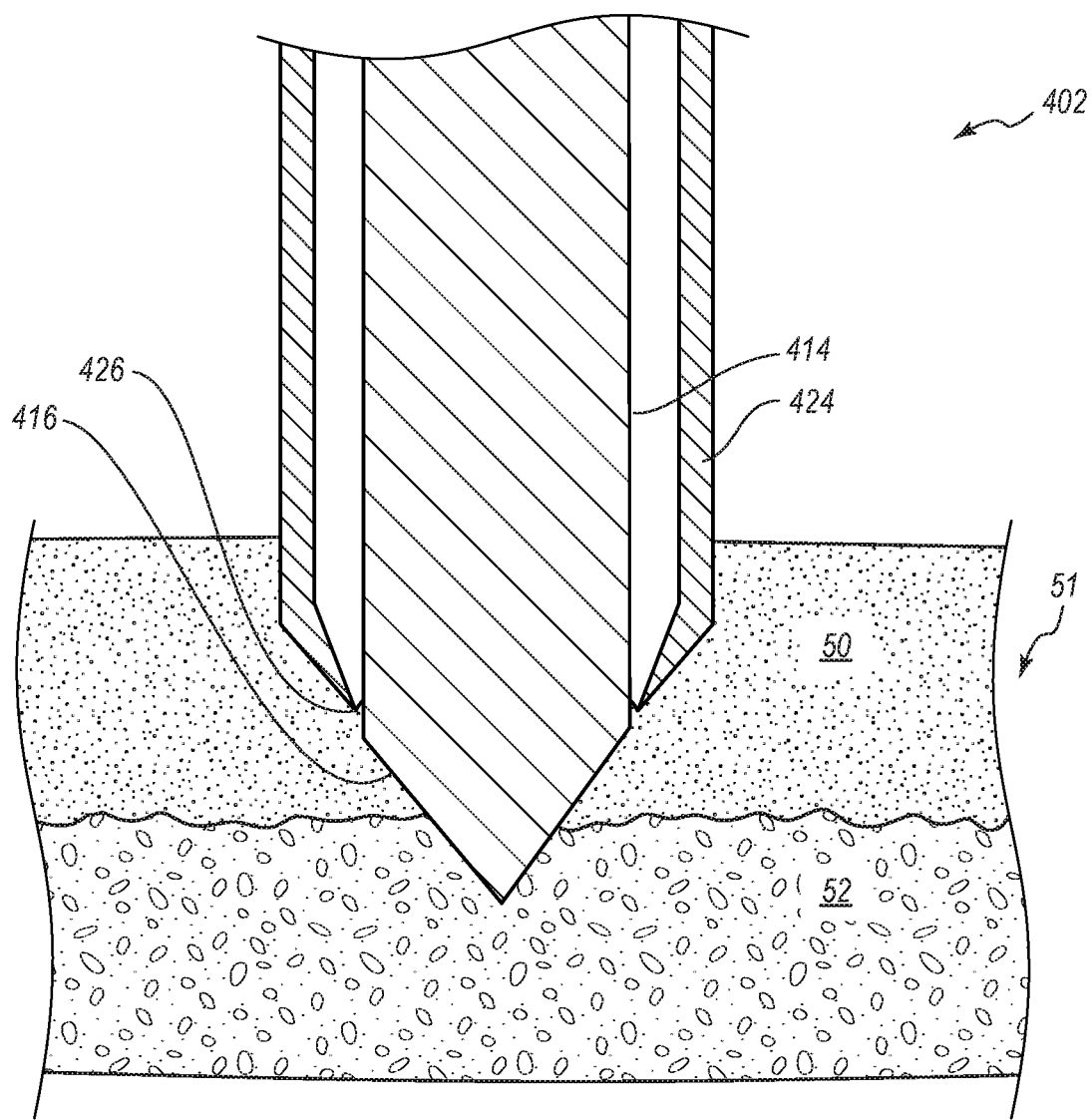
FIG. 15A is a cross-sectional view of a distal end of a portion of the system of FIG. 9 during a stage of an illustrative method of using the system, wherein a distal end of the cortical drilling assembly is being drilled through a cortical layer of a bone of a patient.
Figure 15B:
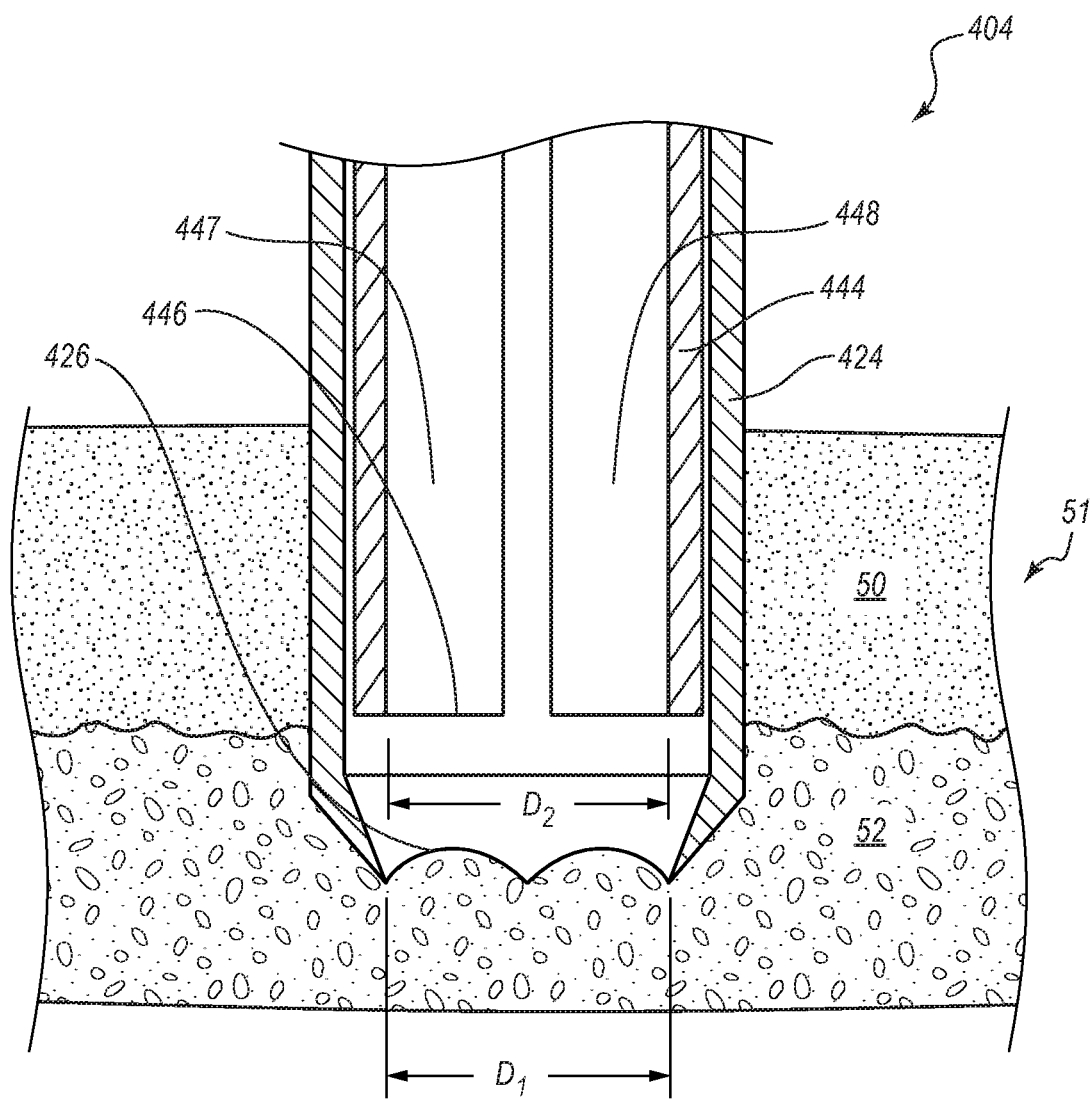
FIG. 15B is a cross-sectional view of the distal end of a portion of the system during a subsequent stage of the illustrative method, wherein a cutting cannula has been drilled through the cortical layer of the bone and has been left implanted in the bone, wherein a trocar has been removed from the cutting cannula, and wherein a distal end of an extraction cannula is being inserted distally through the cutting cannula as the extraction cannula is coupled to the cutting cannula.

With continued reference to FIG. 9, and with additional reference to FIG. 15B, the cutting tip 426 of the cutting assembly 420 can include a cutting configuration suitable both for cutting through the cortical layer of bone and for cutting through marrow so as to core a sample from the marrow. For example, the cutting tip 426 can include any suitable number or configuration of teeth, serrations, embedded cutting elements, and/or other cutting members.

As shown in FIG. 15B, in some embodiments, at least an inner surface of the distal cutting tip 426 of the cutting cannula 424 can narrow slightly to define a reduced diameter $D_1$. In particular, as with other embodiments discussed herein, the coring tip 426 can define the inner diameter $D_1$ (which may be a minimum inner diameter of the tip 426) that is identical to, substantially identical to, or slightly larger than an inner diameter $D_2$ of at least a distal tip of the extraction cannula 444—in particular, that is identical to, substantially identical to, or slightly larger than an inner diameter $D_2$ defined by at least the distal end of the extraction tip 446 of the extraction cannula 444. That is, in various embodiments, the diameter $D_1$ may be the same, substantially the same as, or slightly larger than the diameter $D_2$. The distal region of the cutting cannula 424 that defines the reduced diameter $D_1$ may be referred to as a constriction, an extraction arm deflector, and/or a deflection region.

In manners similar to those discussed above with respect to the coring cannula 130, the cutting cannula 424 can cut through marrow to form a core sample from the marrow, and the core sample can have an outer diameter that matches or substantially matches an inner diameter defined by the distal tip 446 of the extraction cannula, or stated otherwise, the core sample is sized to be readily received into the distal tip 446 of the extraction cannula 444 and engage therewith, such that the extraction cannula 444 becomes rotationally fixed relative to the core sample.

With reference again to FIG. 9, the system 400 can further include a push rod assembly 460, which can include a hub 462 and a push rod 464 fixedly secured to the hub 462. As depicted in a third style of broken lines, the push rod 464 can be inserted into the extraction assembly 440 after the extraction assembly 440 has been decoupled and removed from the cutting assembly 420.

As previously discussed, and as shown in FIGS. 9 and 13, the extraction assembly 440 can define a lumen 445 that extends from a proximal end thereof to a distal end thereof. In particular, in the illustrated embodiment, the extraction cannula 444 defines an entirety of the lumen 445. Thus, after a sample has been extracted from the bone via the extraction cannula 444, the push rod 464 can be inserted through the proximal end of the extraction cannula 444 and advanced distally through the lumen 445 to push the sample through the distal end of the extraction cannula 444, thereby releasing the sample from the extraction cannula 444, as discussed further below.

Figures 10A, 10B:
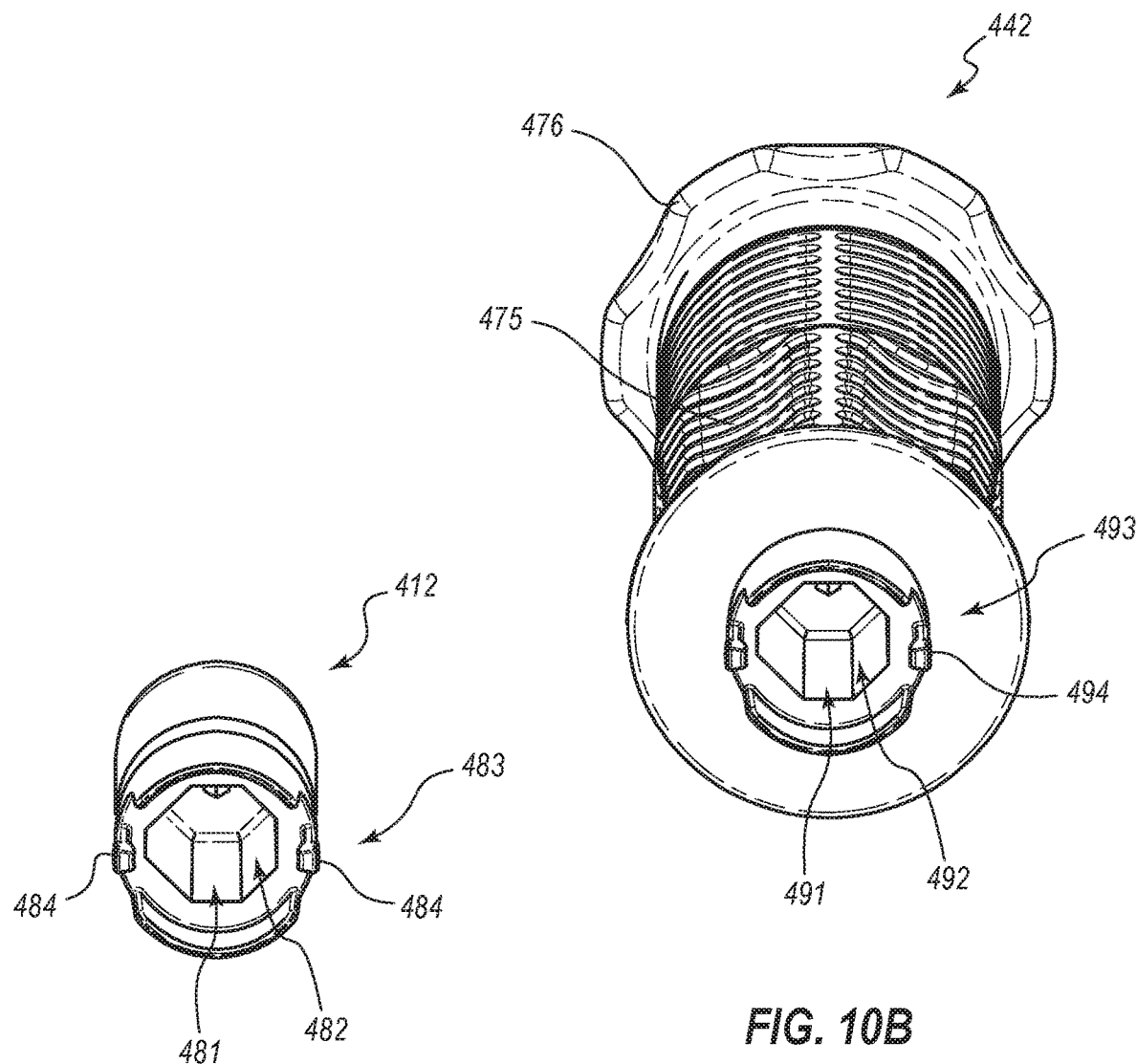
FIG. 10A is a bottom perspective view of an embodiment of a trocar assembly hub.
FIG. 10B is a bottom perspective view of an embodiment of an extraction assembly hub.

FIG. 10A depicts a bottom perspective view of the trocar assembly hub 412. The hub 412 defines a rotational connection interface 481 that is configured to couple in a rotationally fixed manner with a rotational connection interface of the cutting assembly hub 422. In particular, the connection interface 481 of the illustrated embodiment is a socket 482. The socket 482 can define a keyed shape that permits the cutting assembly hub 422 to be coupled to the trocar assembly hub 412 in only one unique rotational or angular orientation. In particular, in the illustrated embodiment, the socket 482 defines an elongated right octagonal prism of which five contiguous sides are substantially identically sized, two enlarged sides that extend from the ends of the five contiguous sides are lengthened relative to the five contiguous sides, and an eighth shortened side that extends between the two enlarged sides is shorter than the five contiguous sides. Any other suitable keying configuration is contemplated.

The trocar assembly hub 412 can further define a translational connection interface 483 that is configured to secure the assembly hub 412 to the cutting assembly hub 422 in a manner that inhibits translational movement between the hubs 412, 422. In the illustrated embodiment, the connection interface 483 comprises a pair of resilient arms 484 that are configured to snap onto the cutting assembly hub 422—specifically, to snap over an outer rim of the cutting assembly hub 422. A strength of the snapping engagement of the arms 484 to the cutting assembly hub 422 can be adjusted to a desired level. During drilling, distally directed forces that are applied to the trocar assembly 410 can tend to maintain the trocar assembly 410 coupled to the cutting assembly 420, independent of a coupling strength provided by the connection interface 483.

In some embodiments, the arms 484 provide only a light coupling force such that the trocar assembly 410 can be readily removed from the cutting assembly 420. For example, in some embodiments, it can be desirable to withdraw the trocar assembly 410 proximally from the cutting assembly 420 with relatively little force, such as after the cutting cannula 422 has been embedded within the cortex of a bone. In particular, it may be desirable to remove the trocar assembly 410 from the cutting assembly 420 merely by pulling back, or proximally, on the trocar assembly hub 412 while the cutting cannula 422 remains engaged with or secured in the bone.

FIG. 10B depicts a bottom perspective view of the extraction assembly hub 442. The hub 442 can resemble the manual driver 374 discussed above with respect to FIGS. 7 and 8 in many respects. Indeed, the hub 442 may also be referred to as a manual driver, a handle, etc. In some embodiments, the hub 442 includes a body 475 and a cap 476, which can resemble the body 375 and the cap 376 discussed above, respectively. For example, in some embodiments, the body 475 and the cap 476 can rotate relative to each other, whereas in other embodiments, the body 475 and the cap 476 are fixedly secured together (e.g., they may be formed of a unitary piece of material).

The extraction assembly hub 442 can define a rotational connection interface 491 that is configured to couple in a rotationally fixed manner with a rotational connection interface of the cutting assembly hub 422. For example, the connection interface 491 can resemble the connection interface 481 discussed above. In particular, the connection interface 491 of the illustrated embodiment is a socket 492. The socket 492 can define a keyed shape that permits the cutting assembly hub 422 to be coupled to the extraction assembly hub 442 in only one unique rotational or angular orientation. In particular, in the illustrated embodiment, the socket 492 defines an elongated right octagonal prism of which five contiguous sides are substantially identically sized, two enlarged sides that extend from the ends of the five contiguous sides are lengthened relative to the five contiguous sides, and an eighth shortened side that extends between the two enlarged sides is shorter than the five contiguous sides. Any other suitable keying configuration is contemplated.

The extraction assembly hub 442 can further define a translational connection interface 493 that is configured to secure the extraction assembly hub 442 to the cutting assembly hub 422 in a manner that inhibits translational movement between the hubs 442, 422. In the illustrated embodiment, the connection interface 493 comprises a pair of resilient arms 494 that are configured to snap onto the cutting assembly hub 422. A strength of the snapping engagement of the arms 494 to the cutting assembly hub 422 can be adjusted to a desired level. During manual drilling, distally directed forces that are applied to the extraction assembly hub 442 can tend to maintain the extraction assembly 440 coupled to the cutting assembly 420, independent of a coupling strength provided by the connection interface 493.

In some embodiments, the arms 494 of the extraction assembly hub 442 provide a stronger coupling force with the cutting assembly 420 than do the arms 484 of the trocar assembly 410. In other embodiments, the coupling force may be approximately the same or even smaller. In various embodiments, regardless of the amount of coupling force provided by the arms 494 on their own, the locking collar 458 (see FIGS. 9 and 13) may be used in conjunction with the arms 494 to achieve a secure connection between the hubs 442, 422. In various embodiments, an overall strength of connection between the extraction assembly hub 442 and the cutting assembly hub 422 (e.g., via the locking mechanism 456) when they are coupled together is greater than the strength of connection between the trocar assembly hub 12 and the cutting assembly 422 hub when they are coupled together.

In some instances, a stronger connection may be desirable for removal of the cutting assembly 420 from the bone. That is, whereas it may be desirable to leave the cutting assembly 420 implanted in the bone during removal of the trocar assembly 410, it can instead, in some instances, be desirable to remove the cutting assembly 420 from the bone concurrently with removal of the extraction assembly 440 from the bone. In certain of such instances, the connection forces provided by the locking mechanism 456 are sufficient to permit such concurrent withdrawal of the extraction assembly 440 and the cutting assembly 420 from the bone.

Figure 10C:
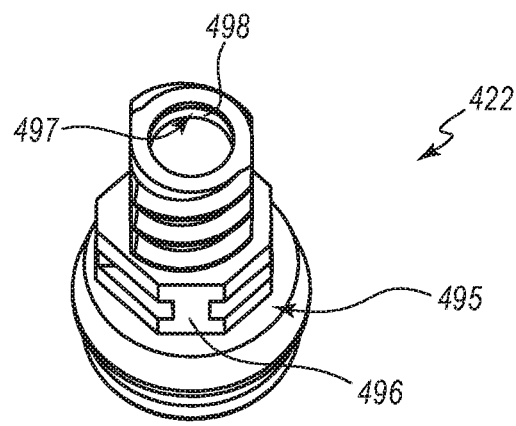
FIG. 10C is a top perspective view of an embodiment of a cutting assembly hub.

FIG. 10C depicts a top perspective view of the cutting assembly hub 422. The cutting assembly hub 422 can define a rotational connection interface 495 that is configured to individually couple in a rotationally fixed manner with each of the rotational connection interfaces 481, 491 of the trocar assembly hub 412 and the extraction assembly hub 442, respectively. The connection interface 495 of the illustrated embodiment is a post 496 that defines a keyed shape that is complementary to the keyed shapes of the sockets 482, 492 discussed above. In particular, in the illustrated embodiment, the post 496 defines an elongated right octagonal prism of which five contiguous sides are substantially identically sized, two enlarged sides that extend from the ends of the five contiguous sides are lengthened relative to the five contiguous sides, and an eighth shortened side that extends between the two enlarged sides is shorter than the five contiguous sides. Any other suitable keying configuration is contemplated.

The cutting assembly hub 442 can further define a coupling interface 497 by which the safety shield 419 can be selectively secured to the cutting assembly hub 442. In the illustrated embodiment, the coupling interface 497 is a recess 498 into which portions of the safety shield 419 can be received, as further discussed below. In particular, the illustrated recess 498 comprises an annular groove that extends about a full periphery of an inner surface of the cutting assembly hub 442.

The cutting assembly hub 442 can also define a coupling interface 499 by which each of the connection interfaces 483, 493 of the trocar assembly hub 412 and the extraction assembly hub 442, respectively, can be selectively secured to the cutting assembly hub 442. In the illustrated embodiment, the coupling interface 499 comprises an annular protrusion over which the resilient arms 484, 494 can snap. Another other connection mechanisms are contemplated.

Figure 10D:
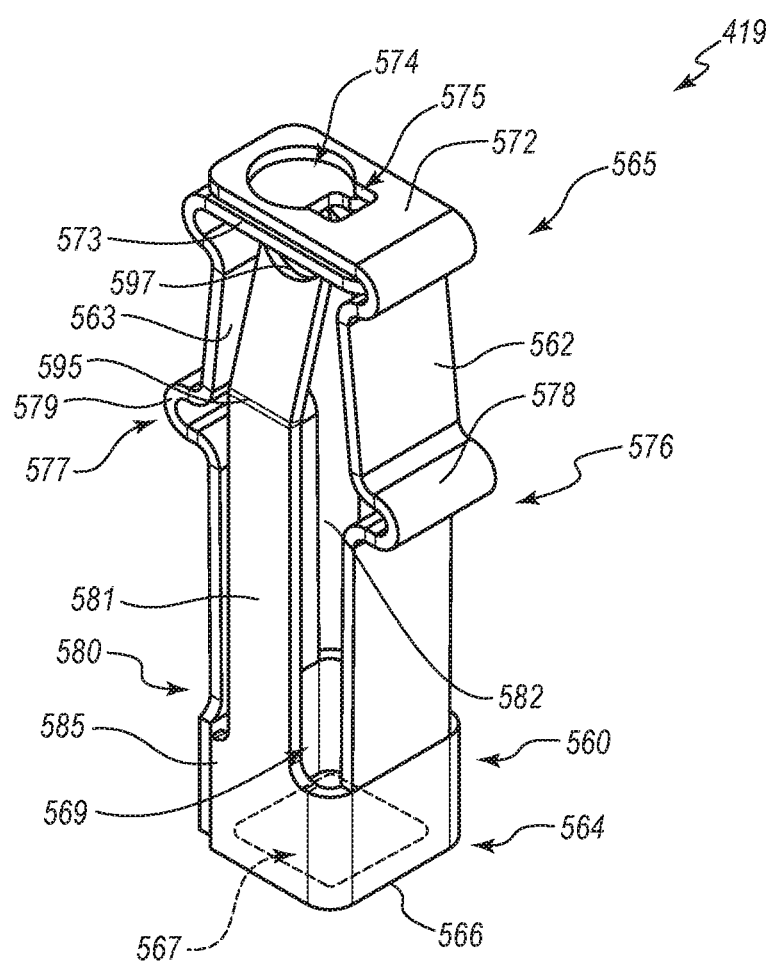
FIG. 10D is a top perspective view of an embodiment of a safety shield.

FIG. 10D depicts a perspective view of an illustrative embodiment of the safety shield 419, which may also be referred to as, for example, a guard, clip, cover, or stick-prevention element. The safety shield 419 includes a collar 560 and a pair of arms 562, 563. In the illustrated embodiment, the arms 562, 563 extend proximally from a proximal end of the collar 560. As further discussed below, the arms 562, 563 may be resiliently flexible members. The arms 562, 563 may be formed such that they are in a natural, resting, non-deflected, nondisplaced, nondeformed, undistorted, unflexed, or relaxed state when in the low-profile orientation depicted in FIG. 10D, or are at least closer to such a low-energy state than then are when moved to an outwardly displaced state such as that depicted in FIGS. 9 and 11. For example, the arms 562, 563 may be deformed, displaced, flexed, or deflected laterally or radially outwardly away from a longitudinal axis of the shield 419 to achieve an orientation such as that depicted in FIGS. 9 and 11, which may give rise to an internal bias that naturally urges the arms 562, 563 back toward their natural state or toward a lower energy state.

The shield 419 can define a distal end 564 and a proximal end 565. In the illustrated embodiment, the collar 560 is positioned at the distal end 564 of the shield 419. The illustrated collar 560 defines a substantially rectangular transverse cross-section, although other configurations are contemplated. The collar 560 can define a distal tip 566 or distal edge of the shield 419. In the illustrated embodiment, the distal tip 566 includes a substantially planar face.

The collar 560 can define a distal opening 567 through which the trocar 414 can pass. In various embodiments, the distal opening 567 may define a fixedly open configuration. Stated otherwise, in some embodiments, the opening 567 is configured to remain open even after the distal tip 416 of the trocar 414 has been drawn into the shield 419. In other terms, the collar 560 may be substantially nondeformable or may define a single shape throughout full operation of the shield 419.

As further discussed below, in some embodiments, the collar 560 is capable of inhibiting or preventing undesired contact with the distal tip 416 of the trocar 414, although the distal opening 567 remains open when the shield 419 is locked onto the trocar 414. For example, the distal opening 567 may be sized to prevent the skin of a user or other individual from entering into a cavity 569 of the shield 419 to a sufficient distance to come into contact with the distal tip 416 of the trocar 414.

In the illustrated embodiment, the cavity 569 is generally defined by the collar 560, distal ends of the arms 562, 563, and a pair of panels 581, 582. Stated otherwise, a cage 580 or receptacle may be defined by the collar 560, the arms 562, 563, and the panels 581, 582. The cage 580 can prevent inadvertent contact with the distal tip 416 of the trocar 414 when the distal tip 416 has been drawn into and is being retained therein.

In the illustrated embodiment, at the proximal end 565 of the shield 419, the arms 562, 563 define lateral extensions 572, 573, respectively, which may extend in opposite directions. Each of the lateral extensions 572, 573 can define openings 574, 575 through which the trocar 414 can pass. The openings 574, 575 can be keyhole shaped with enlarged regions that permit ready passage of the trocar 414 and narrowed portions that are configured to enter into the groove 417 of the trocar 414 to lock, delimit, inhibit, or prevent axial movement between the shield 419 and the trocar 414 (see FIG. 12). In the illustrated embodiment, the openings 574, 575 are shaped substantially identical to each other, but are oriented in opposite directions. The enlarged portions of the openings 574, 575 are shaped substantially as semicircles, and the constricted portions of the openings 574, 575 are shaped substantially as rectangles. Other configurations are contemplated.

In some embodiments, one or more of the arms 562, 563 can define one or more connection interfaces 576, 577, respectively, that can engage the needle hub 203, as discussed further below. In the illustrated embodiment, the connection interfaces 576, 577 are directed outwardly so as to engage the connection interface 497 of the cutting assembly hub 422 when the arms are deformed or distorted outwardly and are held in this outward orientation by the larger diameter portion of the trocar 414. In the illustrated embodiment, the connection interfaces 576, 577 are formed as outwardly directed protrusions 578, 579. For example, in the illustrated embodiment, the protrusions 578, 579 are formed as outward bends in the arms 562, 563, respectively.

The shield 419 further includes a pair of panels 581, 582 at separate opposing sides thereof. In particular, the panels 581, 582 are offset from the arms 562, 563 by 90 degrees about a longitudinal axis of the shield 419. The panels 581, 582 may also be referred to as supports, struts, beams, etc.

Figure 12:
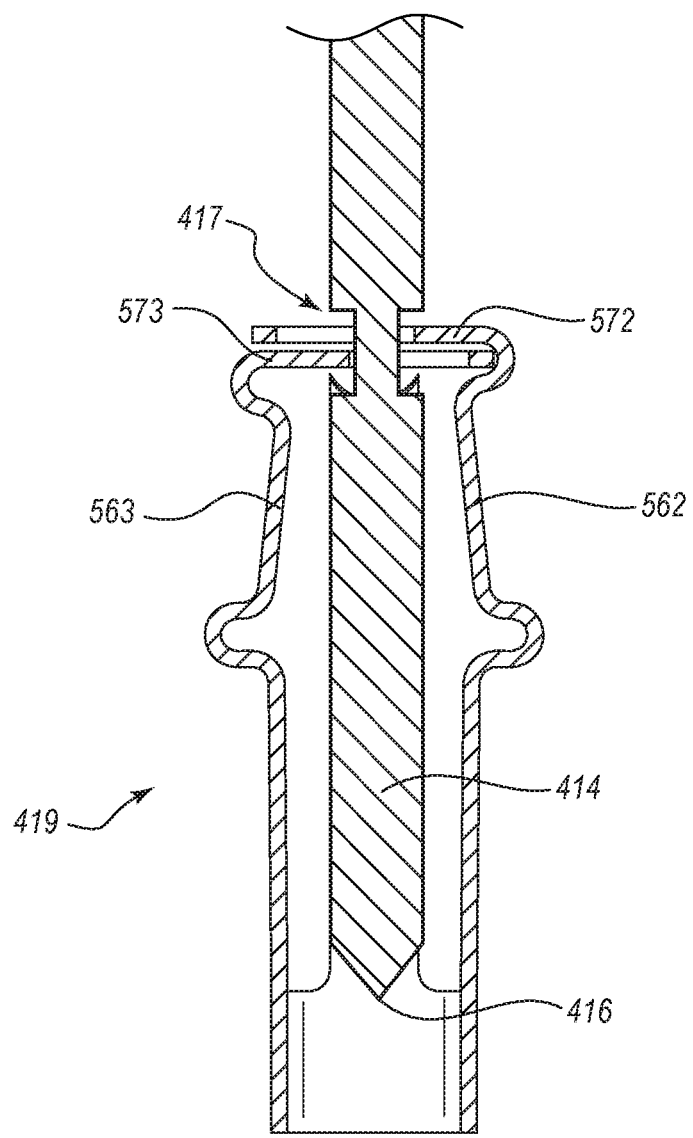
FIG. 12 is a cross-sectional view of the safety shield of FIG. 10D engaged to a distal end of a trocar.

The panels 581, 582 can be configured to provide support (e.g., supplemental support), to prop up, to strengthen, or otherwise assist the lateral extensions 572, 573. The panels 581, 582 can have proximal ends that are positioned adjacent to, beneath, or in contact with a distal surface of the lateral extension 573. In the event of a large distally directed force on the upper lateral extension 572, the lateral extension 572 may move downward into contact with the lateral extension 573, which may in turn move downward into contact with the proximal ends of the panels 581, 582. The panels 581, 582 can prevent any further distal movement or displacement of the lateral extensions 572, 573, which can prevent deformations of the lateral extensions 572, 573 that might otherwise decouple the lateral extensions 572, 573 from the trocar 414 (e.g., when the shield 419 is in the locked configuration, as shown in FIG. 12), such as by reorienting openings defined by the lateral extensions 572, 573 to a position where the trocar 414 can pass through the openings. For example, such deformations or reorientations could decouple the lateral extensions 572, 573 from the recess 417 of a trocar 414.

As an illustrative example, in some instances, the lateral extensions 572, 573 may be securely locked within the trocar recess 417, which can include a proximal sidewall. In the event of application of inadvertent pressure to the distal end of the shield 419 (e.g., a practitioner's inadvertent bumping against the distal end of a trocar assembly, such as might otherwise result in a sharps injury in the absence of the shield 419), reactive forces from the proximal sidewall of the trocar recess can act on the upper lateral extension 572, tending to push it distally. As previously discussed, the panels 581, 582 can assist in preventing such inadvertent force from decoupling the shield 419 from the trocar in a manner that might expose the distal tip of the trocar.

In the illustrated embodiment, the support panels 581, 582 are angled inward, such that their proximal ends are positioned beneath the lateral extension 573. In particular, each support panel 581, 582 includes a bend 595 that directs the support structure inward. This bend 595 provides further strength to the system. The bends 595 redirect forces inward, thus pushing the upper ends of the support panels 581, 582 against the trocar and tending to ensure that the upper ends remain beneath the lateral extensions 573, 572. In some embodiments, the upper ends of the support panels 581, 582 define a curve 597 to achieve better contact with a rounded trocar.

In various embodiments, the shield 419 may be formed of a unitary monolithic piece of material, or stated otherwise, may have a single-piece construction. For example, in some embodiments, the shield 419 may be formed of a single piece of sheet metal (e.g., stainless steel) that has been folded and/or bent into the configuration depicted in FIG. 10D. For example, in the illustrated embodiment, the shield 419 is folded into a substantially rectangular form at four primary bends, one at each corner of the collar 560. Additional bends (in some instances, two bends each) yield each of the lateral extensions 572, 573. In some embodiments, the additional bends (in some instances, three bends each) yield the outward protrusions 578, 579. Upon folding or bending the single sheet of metal, opposite edges of the sheet may be in contact or in close proximity with each other along a seam 585. In the illustrated embodiment, the seam 585 extends longitudinally along the arm 581. In other embodiments, the seam 585 may instead be located at one of the bends of the collar 560, so as not to be present along or through any of the arms 562, 563, 581, 582.

In other embodiments, the shield 419 may be injection molded, 3D-printed, or formed in any other suitable manner. In other or further embodiments, the shield 419 may be formed of multiple pieces that are joined together.

Any other suitable shield configuration is contemplated. For example, illustrative shield configurations are disclosed in U.S. patent application Ser. No. 15/914,964, filed Mar. 7, 2018, titled SAFETY SHIELDS FOR ELONGATED INSTRUMENTS AND RELATED SYSTEMS AND METHODS, published as U.S. Patent Application Publication No. 2018/0256209 on Sep. 13, 2018, the entire contents of which are hereby incorporated by reference herein.

With reference to FIG. 11, the trocar 414 can be positioned within the cutting cannula 424 and the hub 412 of the trocar assembly 410 can receive the hub 422 of the cutting assembly 420 therein. For example, during assembly of the cutting assembly 402, the trocar 414 can be advanced distally through a lumen 425 defined by the cutting cannula 424. As previously discussed, the hubs 412, 422 can define any suitable connection interfaces via which the hubs 412, 422 can be coupled together in a locked angular orientation. In the illustrated embodiment, an outer surface defined by a portion of the hub 422 is keyed to fit within a complementarily shaped inner surface defined by a portion of the hub 412. The keyed surfaces lock the hubs 412, 422 in a fixed angular orientation such that rotation of the hub 412 achieves simultaneous rotation of the hub 422. The hub 412 can define a connection interface at a proximal end thereof for coupling with a driver, such as, for example, a hex-shaped post 415. The driver may be of a manual variety, such as a handle that may be rotated or otherwise manipulated by hand (e.g., the manual driver 374 discussed above), or may be of a powered variety, such as a power drill (e.g., the powered driver 172 discussed above). In the system discussed with respect to FIG. 14, the post 415 is configured to couple with a complementary interface defined by a power drill 472.

Operation of the safety shield 419 will now be discussed with reference to FIGS. 10D, 11, and 12. In the pre-use, assembled, or drilling configuration of the cortical drilling assembly 402, as depicted in FIG. 11, the safety shield 419 is in an unlocked state, which may also be referred to as a deflected state or as an open state. In this state, the arms 562, 563 are maintained in an outwardly deflected position by interaction between the openings in through the lateral extensions 572, 573, respectively, and the larger diameter proximal region of the trocar 414. That is, the portion of the trocar 414 that is proximal of the recess 417 defines a diameter that is larger than the diameter of the recess 417. This portion of the trocar 414 fits within the larger openings 574, but is too large to be received within the smaller openings 575.

When the safety shield 419 is in this open or unlocked state, because of the outwardly deflected configuration of the arms 562, 563, the connection interfaces 576, 577 of the safety shield 419 (i.e., the outward protrusions 578, 579 of each arm) are maintained within the connection interface 497 of the cutting assembly hub 422 (i.e., within the groove 498). This interaction between the connection interfaces 576, 577 and the connection interface 497 maintains the safety shield 419 in a coupled configuration with the cutting assembly hub 422. In particular, the safety shield 419 is maintained in a substantially fixed longitudinal position relative to the cutting assembly hub 422. Thus, although the safety shield 419 is in an unlocked state relative to the trocar 414, the safety shield 419 is simultaneously in a coupled, secured, locked, or substantially fixed configuration relative to the cutting assembly hub 422.

After the cortical drilling assembly 402 has been used to drill an access channel through the cortex of a bone in manners such as described below, the trocar assembly 410 can be removed, withdrawn, or pulled proximally away from the cutting assembly 420 while the cutting assembly 420 remains lodged in the bone of the patient. As the trocar assembly 410 is moved proximally relative to the cutting assembly 420, the larger diameter proximal portion of the trocar 414 maintains the safety shield 419 in the unlocked state (relative to the trocar 414) and coupled state (relative to the cutting assembly hub 422).

Eventually, the trocar 414 is withdrawn proximally by a sufficient amount to bring the recess 417 into the region of the lateral extensions 572, 573. With reference to FIGS. 10D and 12, the trocar 414 defines a reduced diameter in the region of the recess 417. Accordingly, the reduced-diameter region of the trocar 414 can be received into the smaller opening 575 defined by each lateral extension 572, 573. In particular, as the reduced-diameter region of the trocar 414 is positioned within the openings of the lateral extension 572, 573, the arms 562, 563 can spring inwardly under a natural bias to urge the smaller openings 575 into the recess 417. The narrowed regions of the lateral extensions 572, 573 that define the smaller openings 575 can interfere with proximal and distal faces of the recess 417 to prevent proximal and distal movement of the shield 419 relative to the trocar 414, respectively. The shield 419 thus can prevent or inhibit inadvertent contact with the distal tip 416 of the trocar 414, as shown in FIG. 12.

With reference to FIG. 13, as previously mentioned, after the trocar assembly 410 has been removed from the cutting assembly 420, the extraction assembly 440 can be inserted into the cutting assembly 420. In particular, the extraction cannula 444 can be advanced distally into the cutting cannula 424 and the extraction assembly hub 442 can be coupled with the cutting assembly hub 420.

In certain embodiments, the extraction assembly 440 includes a stop or stopper 600 coupled to the extraction cannula 444. The stopper 600 can comprise one or more outward extensions of any suitable variety. In the illustrated embodiment, the stopper 600 comprises an outwardly extending ring. The stopper 600 defines an outer diameter that exceeds an outer diameter of a channel 602 defined by the body 475, and thus does not pass through the channel 602. Stated otherwise, the stopper 600 can interface (e.g., interfere) with an inner surface of the body 475 that defines the socket 492 to delimit proximal movement of the extraction cannula 444 relative to the body 475.

Similarly, the actuator 449 can delimit distal movement of the extraction cannula 444 relative to the body 475. In particular, the actuator 449 can interface (e.g., interfere) with an external surface of the cap 476 to limit how far the extraction cannula 444 can move relative to the body 475 in the distal direction.

Accordingly, the extraction cannula 444 can be coupled to the extraction assembly hub 442 so as to have rotational freedom relative thereto and limited translational freedom relative thereto. Stated otherwise, in some embodiments, the extraction cannula 444 can have rotational freedom (e.g., unrestricted rotational freedom) about a longitudinal axis of the extraction cannula 444, whereas a translational freedom of the extraction cannula 444 in the longitudinal direction can be delimited. The longitudinal axis can extend through at least a portion of an interior of the extraction cannula 444. In the illustrated embodiment, the longitudinal axis extends longitudinally through an entirety of the extraction cannula 444.

When the extraction cannula 444 is in a distalmost position, relative to the extraction assembly hub 442, a contact surface, or contact surfaces, of the actuator 449 can be spaced from one or more contact surfaces of the cap 476 with which it/they interact to delimit the distal movement of the extraction cannula 444 by a distance $L_4$. Stated otherwise, the actuator 449 and the stop 600 can cooperate with the extraction assembly hub 442 to delimit a maximum longitudinal distance through which the extraction cannula 444 can move relative to the extraction assembly hub 442 to the distance $L_4$.

During a coring event, the extraction cannula 444 may naturally assume the proximally shifted or retracted orientation depicted in FIG. 13 due to proximally directed forces from the marrow of the bone as the coring and extraction assembly 404 is advanced distally into the marrow. As discussed further below with respect to FIG. 16, in other embodiments, a biasing member may be provided to maintain the extraction cannula 444 in the proximally shifted or retracted orientation prior to distal actuation of the actuator 449.

With continued reference to FIG. 13, the distal tip 446 of the extraction cannula 444 can be recessed relative to the distal tip 426 of the cutting cannula 424 by a distance $L_5$ when the coring and extraction assembly 404 is in a pre-use state, or prior to drilling into marrow. With continued reference to FIG. 13, and with additional reference to FIG. 15E, at a later stage of use, the actuator 419 may be pressed downward toward and into contact with the hub 422 (in particular, into contact with the cap 476) to cause the distal tip 446 of the extraction cannula 444 to extend distally past the distal tip 426 of the cutting cannula 424 by a distance $L_6$. Accordingly, the distance $L_4$ can desirably be at least as great as the distance $L_5+L_6$. In various embodiments, the distance $L_6$ can be no greater than about 0.3, 0.4, 0.5, 0.6, 0.7, or 0.8 millimeters.

The extraction cannula 444 can be configured to rotate freely relative to the extraction assembly hub 442. Similar to the rotational freedom of the extraction cannula 144 discussed above, the rotational freedom of the extraction cannula 444 can permit the extraction cannula 444 to remain rotationally stationary relative to the marrow of the bone while the extraction assembly hub 442 and the cutting assembly 420 rotate in unison during manual coring of the bone marrow. In some embodiments, an upper surface of the stop 600 may contact an inner surface of the hub 442 at an upper end of the socket 492 during the rotation. In some embodiments, the hub 442 and/or the stop 600 may include a friction-reducing material and/or have a friction-reducing coating or other layer disposed thereon in at least the region of contact. For example, in some embodiments, Delrin® may be used to reduce friction.

As previously noted, in some embodiments the locking mechanism 456 can be engaged to lock the hubs 422, 442 together. In the illustrated embedment, the locking mechanism 456 comprises a locking collar 458. The locking collar 458 can be transitioned between an unlocked or retracted position and a locked or deployed position. In the illustrated embodiment, the unlocked position is at or above the proximal end of the attachment arms 443 of the hub 442, thus the locking collar 458 may not interfere with flexure of the arms 443, thus permitting the arms 443 to snap over the hub 422 to connect the hubs 422, 442 to each other or permitting the arms 443 to snap off of the hub 422 to disengage the hubs 422, 442 from each other. In the illustrated embodiment, the locked position is at a position that is over the arms 443, or stated otherwise, that encompasses the arms 443. In particular, as the locking collar 458 is moved distally to the locked position, it is advanced over the arms 443. The locking collar can compress the arms inwardly toward the hub 422, thus preventing outward flexure of the arms 443. In some embodiments, the shape of the locking collar 458 changes during transition from locked to unlocked orientation. For example, in some embodiments, the locking collar 458 defines a substantially circular cross-section when in the retracted position, and is deformed into a more ovalized orientation (with the arms 443 at respective apices of the oval) when advanced into the deployed position. Any other suitable arrangement is contemplated. The deformation may be elastic or plastic in various embodiments. In some embodiments, the deformation gives rise to a restorative bias within the collar 458 that provides inwardly directed forces to the arms 443.

Figure 14:
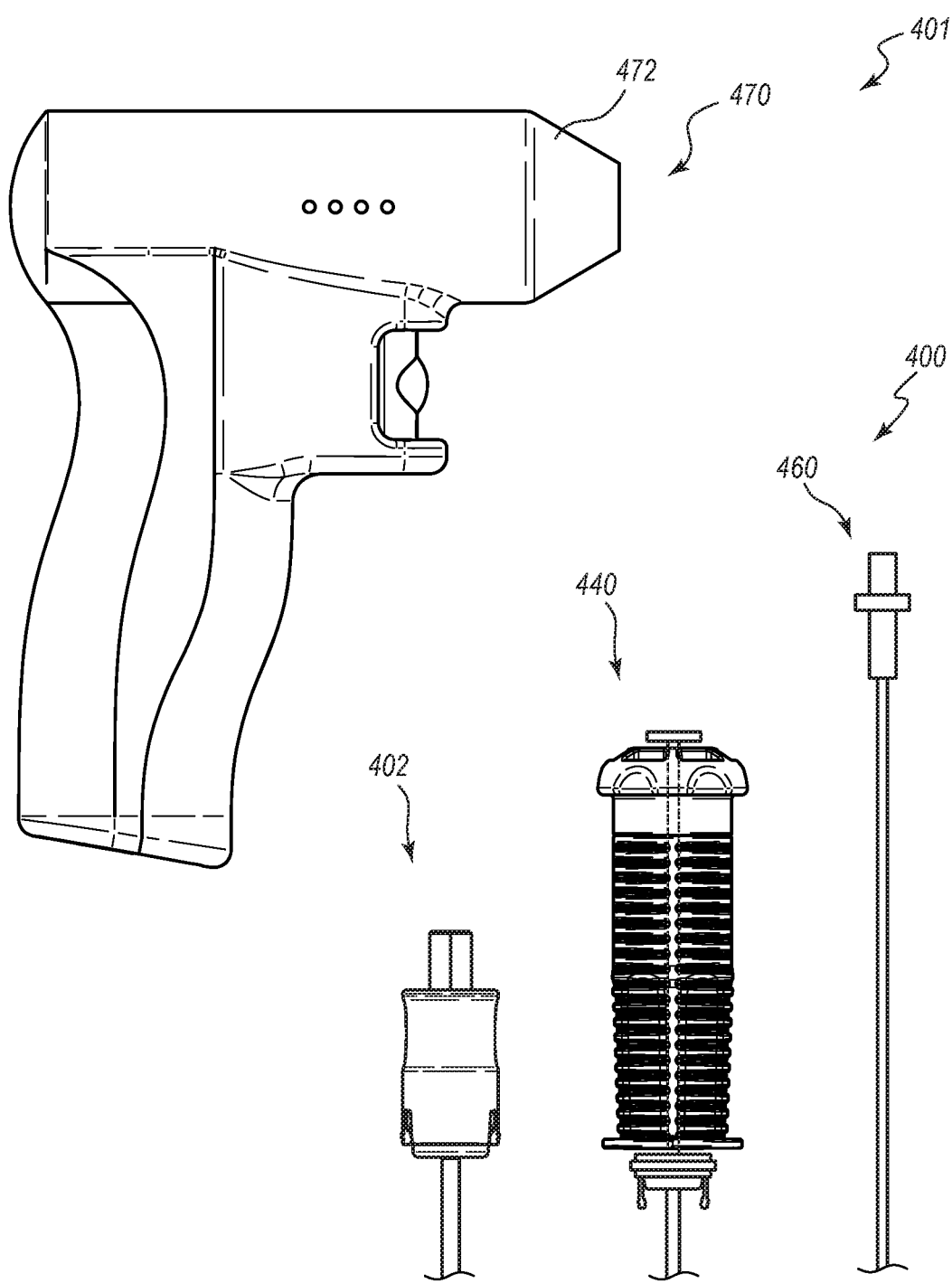
FIG. 14 is an elevation view of a further embodiment of a bone biopsy system that includes the system of FIG. 9 and additionally includes a driver configured to couple with a portion thereof.

With reference to FIG. 14, in some embodiments, a bone biopsy system 401 can include not only the system 400 just described, but also a driver 470. The driver 470 can be selectively coupled with the cortical drilling assembly 402. In particular, the driver 470 can be configured to selectively couple with the driver connector or connection interface 415 (FIG. 9) at the proximal end of the hub 412, as previously described. Any suitable driver 470 is contemplated. In the illustrated embodiment, the driver 470 comprises a power drill 472, which can achieve powered insertion of the cortical drilling assembly 402 into bone.

Illustrative examples of methods of using the systems 400, 401 will now be described. Where a particular drawing is not specified, the figures may be referenced generally.

With reference to FIG. 15A, in some methods, the cortical drilling assembly 402 is provided. This may also be referred to as a cortical cutting assembly or as a marrow access assembly. In particular, with reference to FIGS. 9 and 11, the trocar assembly 410 can be coupled with the cutting assembly 420 in manners such as previously disclosed. This may be referred to as a power drilling configuration of the system 400. In some instances, the trocar assembly 410 and the cutting assembly 420 may come preassembled in this fashion, such as by being prepackaged and shipped in this configuration. That is, a user may remove the system 400 from packaging with the cutting assembly 420 and the trocar assembly 410 in the coupled state or power drilling configuration. The trocar hub 412 can be coupled to the drill 472 in manners such as previously disclosed, and the cutting assembly 420/trocar assembly 410 combination can thereby be drilled into a bone 51 of a patient as the drill 472 is actuated.

With reference again to FIG. 15A, the trocar 414 and the cutting cannula 424 can rotate in unison and each cut through the cortical layer 50 of the bone to reach the marrow 52 of the bone. In the stage of the method depicted in FIG. 15A, a portion of the distal tip 416 of the trocar 414 has passed through the cortical layer 50 into the marrow 52, whereas the remainder of the distal tip 416 of the trocar 414 and the distal tip 426 of the cutting cannula 424 continue to cut through the cortical layer 50.

The cortical drilling assembly 402 can continue to cut deeper into the bone 51 until the distal tip 426 of the cutting cannula 424 passes through the cortical layer 50 of the bone. Thus, the distal cutting tip 426 of the cutting cannula 424 can be positioned within the marrow 52 of the bone (see FIG. 15B). The drill 472 is decoupled and removed from the cortical drilling assembly 402—specifically, is decoupled from the trocar hub 412. The trocar assembly 410 is decoupled and removed from the cortical cutting assembly 420 as the cortical cutting assembly 420 is left in place in the bone 51. In various instances, the drill 472 may be removed from the trocar hub 412 before or after removal of the trocar assembly 410 from the cutting assembly 420.

After the trocar assembly 410 has been removed from the cutting assembly 420, the extraction assembly 440 is coupled to the cutting assembly 420, which forms the coring and extraction assembly 404. The coring and extraction assembly 404 is then used to obtain a sample of the marrow 52.

FIG. 15B depicts a point in time after the extraction assembly 440 has been coupled to the cutting assembly 420 and just before the extraction assembly hub 442 is manipulated by a user to core the marrow 52. This configuration of the system 400, in which the hub 442 (which can also be referred to as the handle 442, as previously noted) is coupled to the cutting assembly 420 for purposes of manual coring, may be referred to as a manual coring configuration of the system 400. Coring can be achieved by rotating the extraction assembly hub 442 and by urging the extraction assembly hub 442 distally into the marrow 52. For example, in some instances a user can press distally on the cap 476 and/or the body 475 (see FIG. 13) while rotating the body 475 and/or the cap 476. The rotation can be in a single direction, in some instances, or can be back and forth in opposite directions, in other or further instances.

Figure 15C:
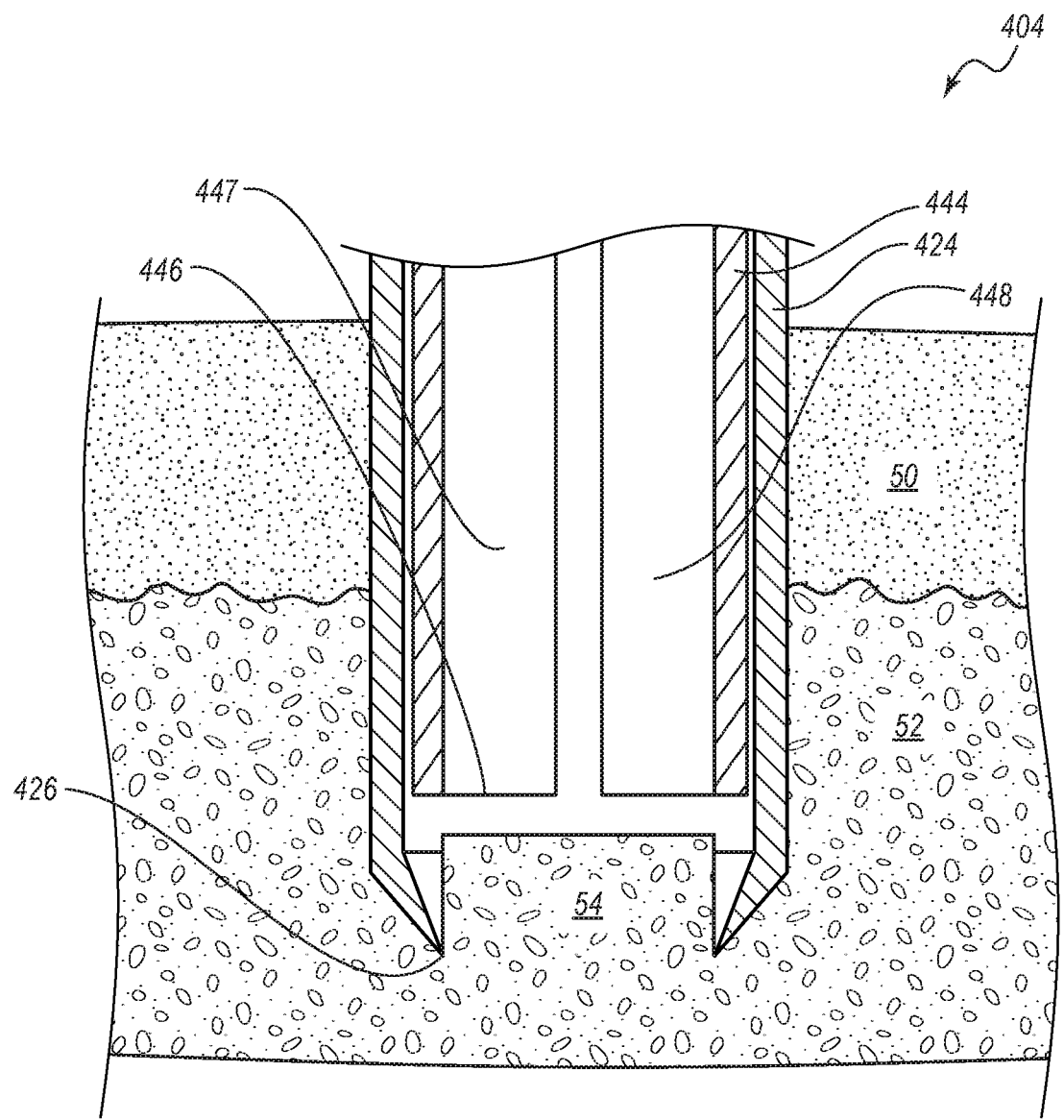
FIG. 15C is a cross-sectional view of the distal end of the portion of the system during a subsequent stage of the illustrative method, wherein the distal tip of the cutting cannula (which may also be referred to as a coring cannula) has begun cutting through marrow of the bone to form a core sample, or core, of the marrow.

With reference to FIG. 15C, manipulation of the extraction assembly hub 442 such as just described can cause the distal tip 426 of the cutting cannula 424 to cut through the marrow 52. That is, as the coring and extraction assembly 404 is rotated and advanced distally, the cutting tip 426 cuts the marrow 52 to core a sample 54 therefrom. The sample 54 may also be referred to as a core, specimen, etc. An outer diameter of the sample 54 can be the same as the inner diameter of the cutting tip 426.

Figure 15D:
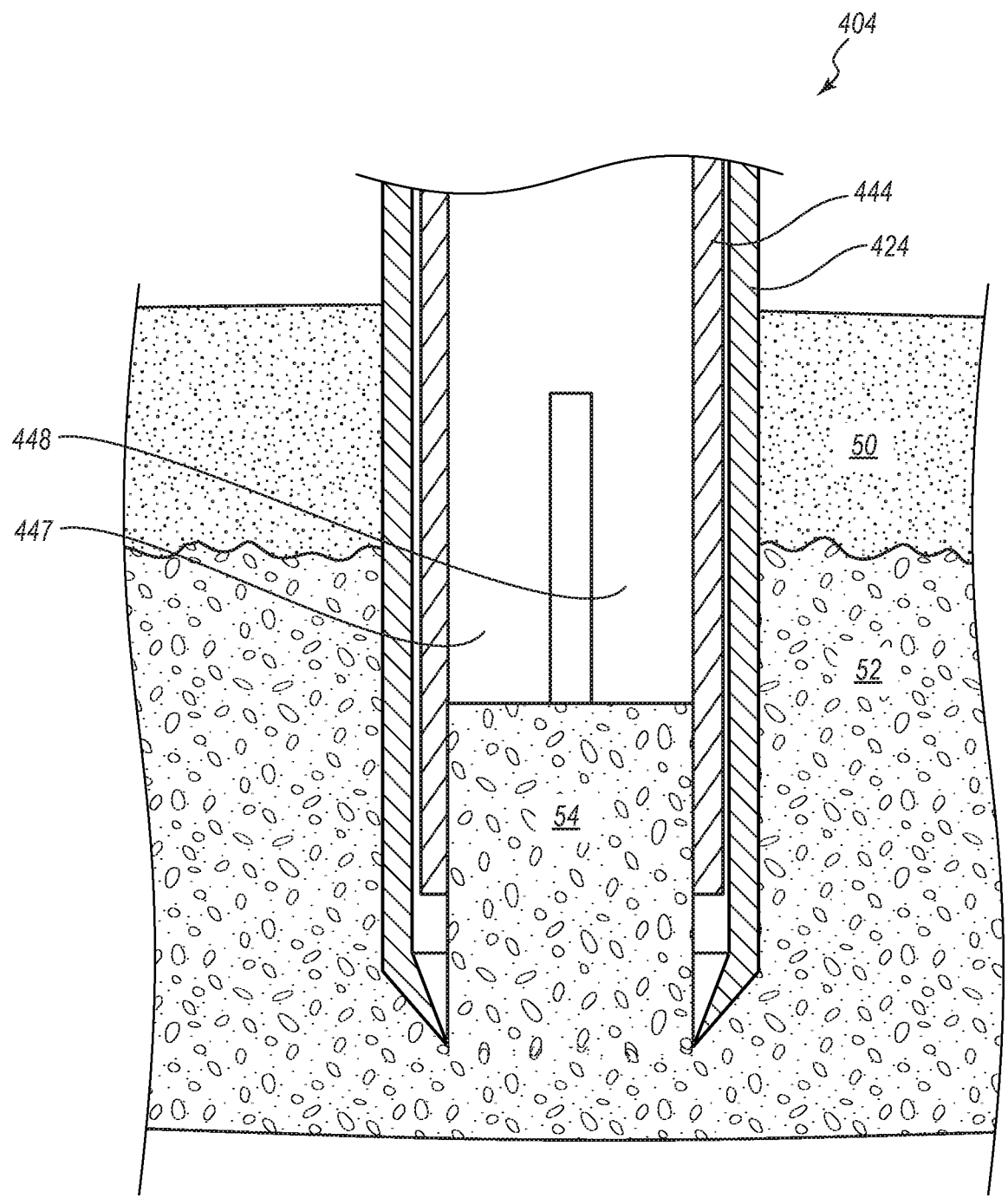
FIG. 15D is a cross-sectional view of the distal end of the portion of the system during a subsequent stage of the illustrative method, wherein the distal tip of the cutting (or coring) cannula has continued cutting through the marrow of the bone to increase the size of the core, and the core has entered into a distal tip of a sample extraction cannula.

With reference to FIG. 15D, as the coring and extraction assembly 404 continues to rotate and advance distally, the coring tip 436 continues to core the sample 54 from the marrow 52. That is, the sample 54 grows in size and is advanced proximally into the coring and extraction assembly 404. Stated otherwise, distal advancement of the coring and extraction assembly 404 positions the growing sample 54 deeper within the coring and extraction assembly 404. Eventually, the sample 54 is advanced proximally by a sufficient amount to enter into the extraction cannula 444. in particular, the sample 54 is advanced proximally between the arms 447, 448 at the distal end of the extraction cannula 444. Again, the outer diameter of the sample 54 is the same or substantially the same as the inner diameter of the cutting tip 426, which is the same as, substantially the same as, or slightly larger than the inner diameter of at least a distal end of the extraction cannula 444. Contact between the sample 54 and the inner wall of the extraction cannula 444 can yield an engagement or frictional force sufficient to rotationally fix the extraction cannula 444 relative to the marrow 52, which can stop and/or prevent the extraction cannula 444 from rotating in unison with the coring cannula 424. Thus, the extraction cannula 444 can be rotationally fixed relative to the sample 54 while the remainder of the coring and extraction assembly 404 continues to rotate for further coring. Stated otherwise, because the extraction cannula 444 has rotational freedom relative to the remainder of the coring and extraction assembly 404 (e.g., relative to the cutting cannula 424 and the extraction assembly hub 442), the extraction cannula 444 can engage the sample 54 and not rotate relative thereto. This can assist in maintaining the structural integrity of the sample 54.

As the coring and extraction assembly 404 is distally advanced further, the sample 54 can advance (e.g., slide) deeper (e.g., more proximally) into the extraction cannula 444 and can be held thereby. The proximal advancement in this manner can proceed smoothly, due to the approximate size match of the sample diameter 54 and the inner diameter of the extraction cannula 444. Eventually, a desired size of the sample 54 is achieved and drilling discontinues.

Figure 15E:
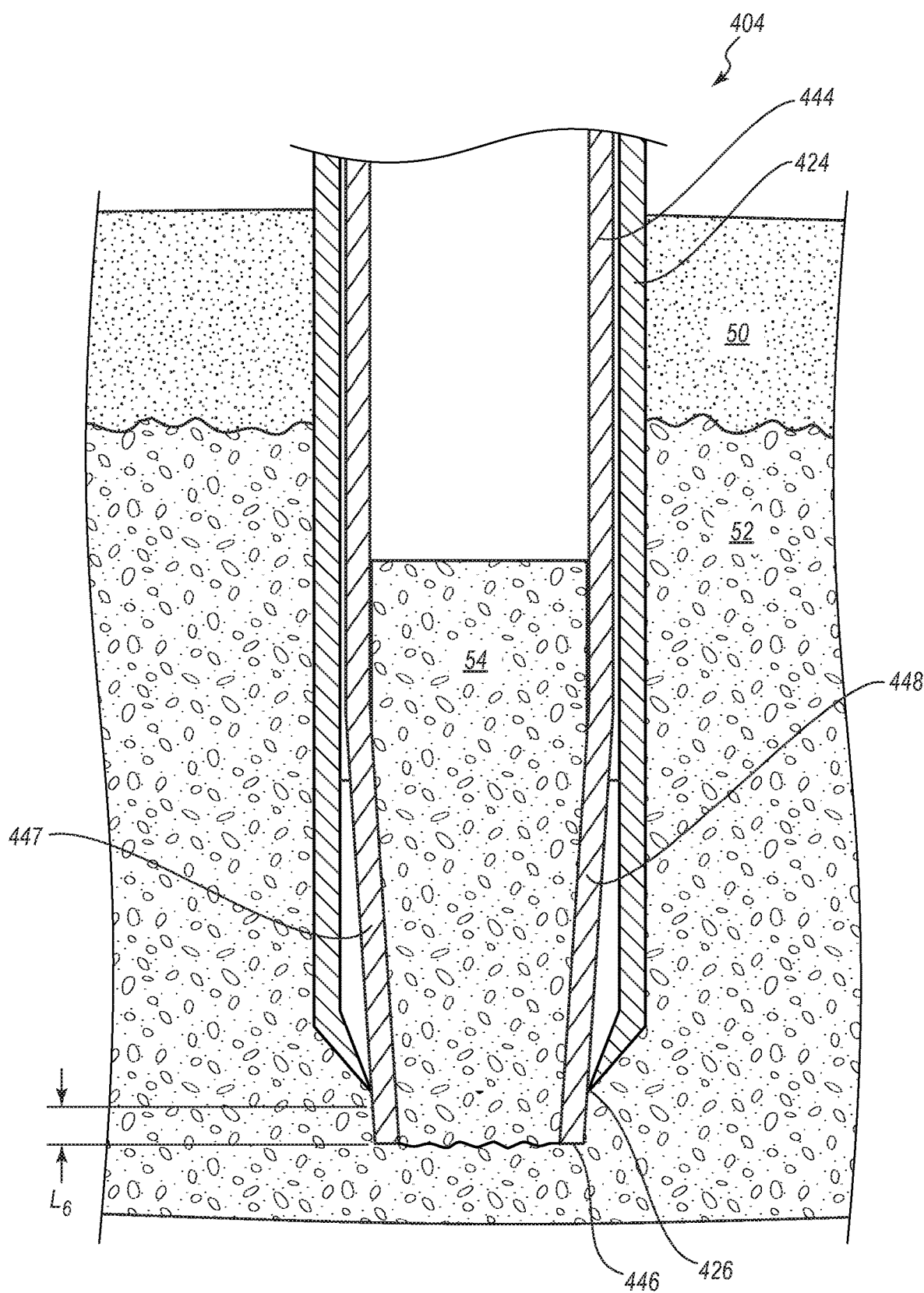
FIG. 15E is a cross-sectional view of the distal end of the portion of the system during a subsequent stage of the illustrative method, wherein the distal tip of the cutting (or coring) cannula has finished cutting through the marrow of the bone, and wherein the distal tip of the sample extraction cannula is advanced through the distal tip of the cutting cannula and the sample extraction cannula is rotated to break the core from the adjacent bone marrow.

With reference to FIG. 15E, once the sample 54 has reached a desired size, the user can press distally on the actuator 449 (see FIGS. 9 and 13) to advance the distal tip 446 of the extraction cannula 444 distally beyond the distal tip 426 of the cutting cannula 424. That is, as the extraction cannula 444 is advanced distally relative to the cutting cannula 424, the distal tip of the extraction cannula (which includes the deformable arms 447, 448) is advanced through the narrowed or constricted opening defined by the distal tip of the cutting cannula 424. The narrowed or constricted arrangement corresponds with the property of the inner diameter being approximately the same as the inner diameter of the extraction cannula 444, as previously discussed.

The arms 447, 448 can deflect or compress inwardly slightly as they are advanced past the distal tip of the cutting cannula 424. The inward deflection of the arms 447, 448 may, for some embodiments, be exaggerated in the depiction shown in FIG. 15E. In any event, the arms 447, 448 can press inwardly on the sample 54 and can thereby increase a grip on the sample 54. In some instances, the inwardly directed, reactive compressive forces of the distal tip 426 of the cutting cannula 424 on the arms 447, 448, which can result from the hoop strength of the distal tip 426, can be sufficient to maintain the extraction cannula 444 in the distally advanced position relative to the cutting cannula 424. In other or further instances, the inward forces can be sufficient to maintain the gripping configuration of the arms 447, 448 relative to the sample 54, such as during rotation of the extraction cannula 444 relative to the cutting cannula 444 as discussed further below.

Once the arms 447, 448 are in their distally advanced state and have achieved an enhanced grip on the sample 54, at least a portion of the extraction assembly hub 442 can be rotated, whether in a single direction (clockwise or counterclockwise) or back and forth, which can effect rotation of the extraction cannula 444 relative to the cutting cannula 424 and the body of marrow 52 that surrounds the cutting cannula 424. The arms 447, 448 can remain in their inwardly deflected state during such rotation, and thus can maintain their grip on the sample 54. Such rotation of the extraction cannula 444 can break or otherwise sever or separate the sample 54 from the body of the marrow 52.

In some instances, the user may continue depressing the actuator 449 during said rotation of at least a portion of the extraction assembly hub 442. For example, the user may press downwardly on the actuator 449 to contact the actuator 449 against the cap 476 with sufficient force to achieve frictional engagement between the actuator 449 and the cap 476 that causes the actuator 449, the extraction tube 444 that is coupled thereto, and the cap 476 to rotate in unison.

In some instances, the user may continue pressing downwardly on the actuator 449 in this manner while rotating the cap 476 relative to the body 475. In other instances, the user may continue pressing downwardly on the actuator 449 in this manner while rotating both the cap 476 and the body 475 together in unison.

In some instances, the user need not continue pressing downwardly on the actuator 449 to maintain the extraction tube 444 in the extended or deployed orientation depicted in FIG. 15E. For example, due to the sandwiching of the distal portions of the arms 447, 448 between the distal tip 426 and the sample 54, the inwardly directed reactive forces from the distal tip 426 of the cutting tube 424 and the outward forces from the sample 54 can be sufficiently strong to prevent distal retraction of the extraction tube 444. In certain of such instances, the user need not continue pressing on the actuator 449 during rotation of at least a portion of the coring and extraction assembly 404—e.g., rotation of the cap 476 and/or rotation of the body 475—in order to break or otherwise sever or separate the sample 54 from the neighboring regions of the marrow 52.

Other arrangements are also contemplated. For example, in some embodiments, the actuator 449 may be configured to selectively lock the extraction tube 444 in the extended or deployed orientation. For example, in some embodiments, the actuator 449 may engage (e.g., via a releasable latch) the cap 476 when depressed into close proximity to the cap 476, and may be selectively released from its depressed orientation. Any suitable locking mechanism is contemplated. In other or further embodiments, the actuator 449 may be lockable in the retracted position. For example, a locking mechanism at the proximal end of the extraction tube 444 may be used, such as a removable spacer that maintains a set distance between the actuator 449 and the cap 476 and that permits rotation of the spacer 449 and the extraction tube 444 relative to the cap 476.

Figure 15F:
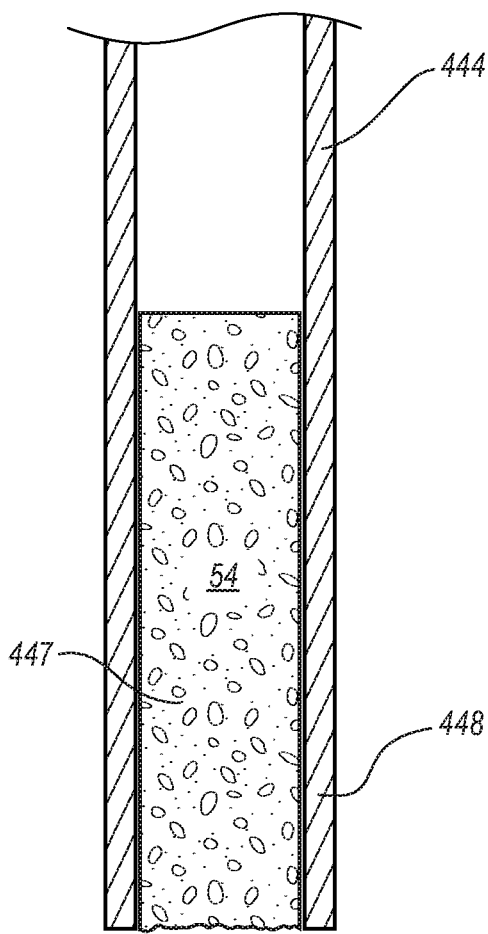
FIG. 15F is a cross-sectional view depicting another stage of the method in which the core has been obtained and is being held by the sample extraction cannula, and in which the sample extraction cannula has been removed from the cutting cannula.
Figure 15G:
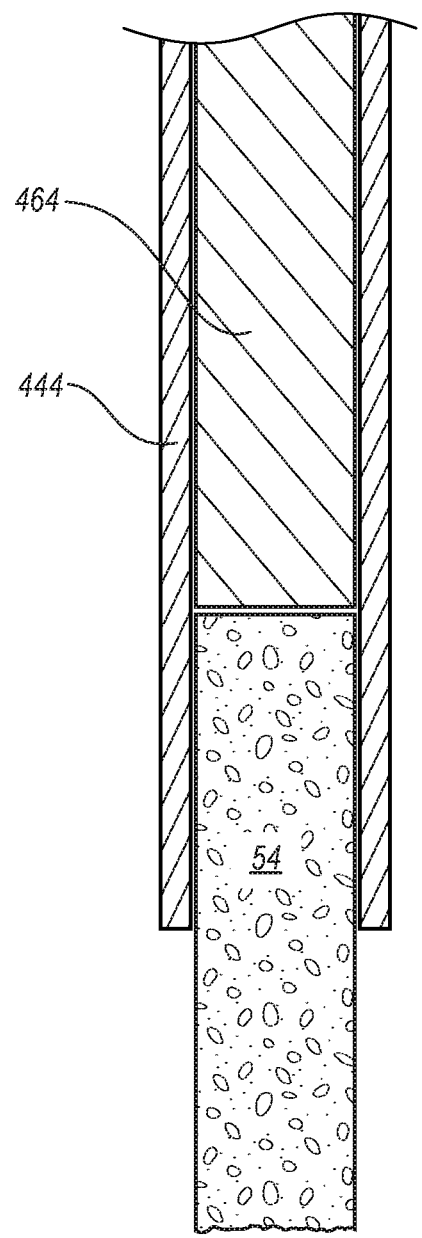
FIG. 15G is a cross-sectional view depicting the core being pushed from the extraction cannula.

With reference to FIG. 15F, the cutting assembly 420 and the extraction assembly 440 can be removed from the patient. In some instances, the locking mechanism 456 is unlocked by pulling the locking collar 458 to its proximal retracted position, thus permitting the extraction assembly 440 to be decoupled from the cutting assembly 420. In some instances, the locking mechanism 456 is unlocked while the coring and extraction assembly 404 is still positioned within the bone of the patient, the extraction assembly 440 is removed from the cutting assembly 420, and then the cutting assembly 420 is removed from the patient. In other instances, the full coring and extraction assembly 404 is removed from the patient, the locking mechanism 456 is then unlocked, and the extraction assembly 440 is then removed from the cutting assembly 420.

Once the extraction assembly 440 has been removed, the push rod 460 can be inserted through the proximal end of the extraction assembly 440 and advanced distally. Specifically, the push rod 460 can be inserted into the proximal end of the lumen or channel 445, advanced through the extraction cannula 444, and into contact with a proximal end of the sample 54. The push rod 460 can be advanced distally by a further amount to push the sample 54 through or out of the distal end of the extraction cannula 444.

In other embodiments, the system may be devoid of a push rod 460. In certain of such embodiments, the trocar 414 may instead be inserted through the extraction cannula 444 to urge the sample 54 through the distal end of the extraction cannula 444.

As previously discussed, the arms 447, 448 may be flexible or readily deformable, such that the arms 447, 448 exert only a loose grip on the sample 54 at this stage. As the sample 54 is pushed past the arms 447, 448, the arms 447, 448 may, in some embodiments, expand or otherwise deform to permit ready passage thereby of the sample 54. In other instances, the arms 447, 448 remain in a natural or unflexed state as the sample 54 is pushed past the arms 447, 448. The sample 54 may thus be provided from the system with a high diagnostic yield. In various instances, the sample 54 may be no less than about 0.5, 1, 1.5, or 2 cm in length.

Figure 16:
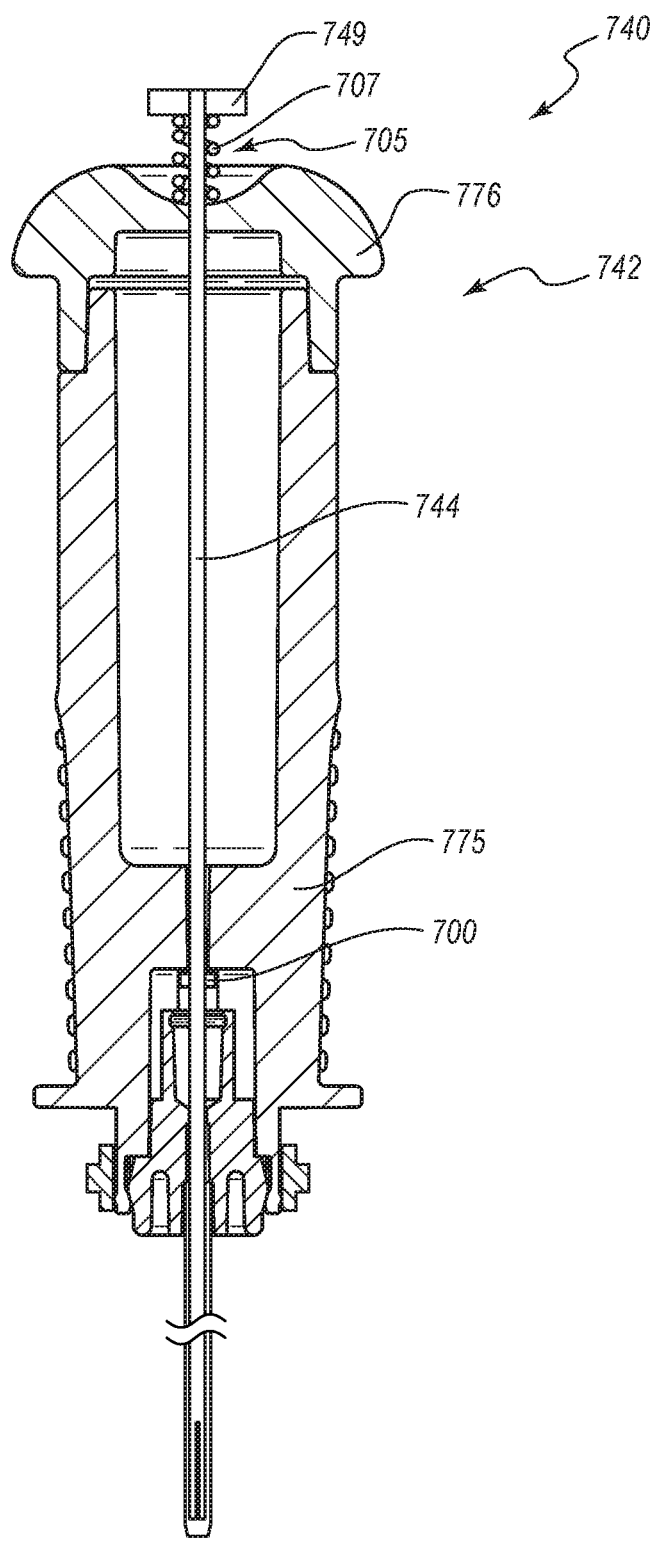
FIG. 16 is a cross-sectional view of another embodiment of an extraction assembly that is compatible, for example, with the system of FIG. 9.

FIG. 16 depicts another embodiment of an extraction assembly 740, which can be used, for example, in place of the extraction assembly 440. The extraction assemblies 440, 740 are substantially similar to each other, except that the extraction assembly 740 includes a biasing member 705 that is configured to retain an extraction tube 744 in a retracted orientation. Stated otherwise, the biasing member 705 biases the extraction tube 740 toward the retracted orientation, such that the bias must be overcome to advance the extraction tube 740 distally. In the illustrated embodiment, the biasing member 705 comprises a compression spring 707 that interfaces with an actuator 749 at a proximal end thereof and that interfaces with an extraction hub 742—specifically, with a cap 776 of the extraction hub 742—at a distal end thereof. The biasing member 705 maintain a stop 700 in contact with a body 775 of the extraction hub 742.

Figure 17:
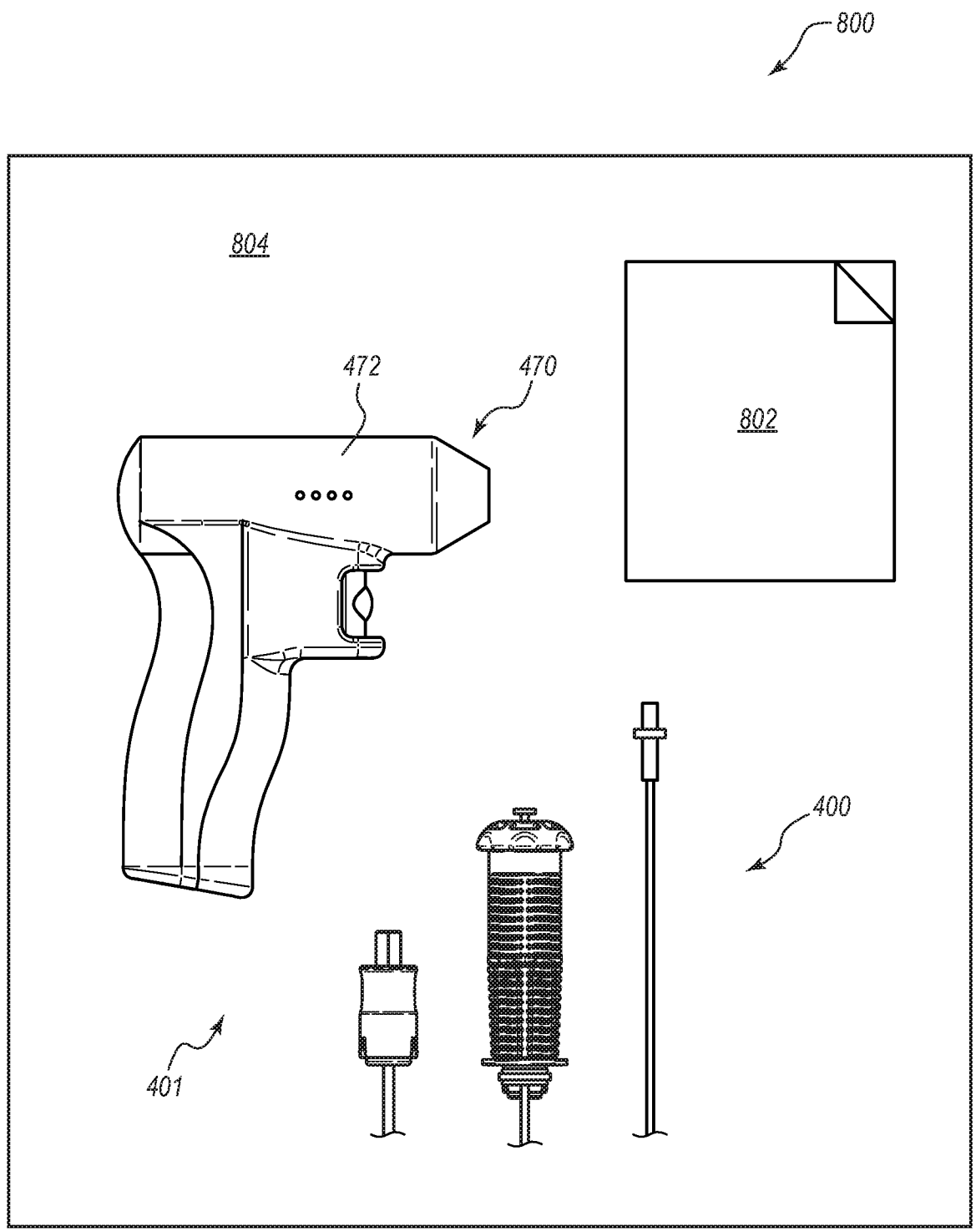
FIG. 17 is an elevation view of an embodiment of a kit that includes the system depicted in FIG. 14.

FIG. 17 depicts an embodiment of a kit 800 for performing a bone biopsy, or stated otherwise, depicts an embodiment of a bone biopsy kit 800. The kit 800 can include any of the bone biopsy systems disclosed herein (e.g., the bone biopsy systems 100, 101, 200, 300, 400, 401) and/or components thereof, or alternative components therefor. For example, in the illustrated embodiment, the kit 800 includes the bone biopsy system 401 described above, which includes the bone biopsy system 400 and a driver 470 for use therewith. In particular, in the illustrated embodiment, the driver 470 is the powered handheld drill 472.

The kit 800 can include instructions for use 802, which may provide directions with respect to any of the methods or processes disclosed herein. That is, any of the methods or method steps described herein with respect to any of the bone biopsy systems may be included as directions in the instructions for use 802. In various embodiments, the kit 800—and, in particular, the instructions for use 802 thereof—can be approved of or authorized by a regulating body of a particular jurisdiction. For example, the kit 800, and the instructions for use 802 thereof, may be approved of or authorized by the Food and Drug Administration of the United States of America and/or may comply with the regulations of other jurisdictions, such as by qualifying for CE marking in the European Union.

The kit 800 may further include packaging 804 that contains the system 401. In some embodiments, the instructions for use 802 are physically contained within the packaging 804. In other or further embodiments, the instructions for use 802 are printed on the packaging 804.

Figure 18:
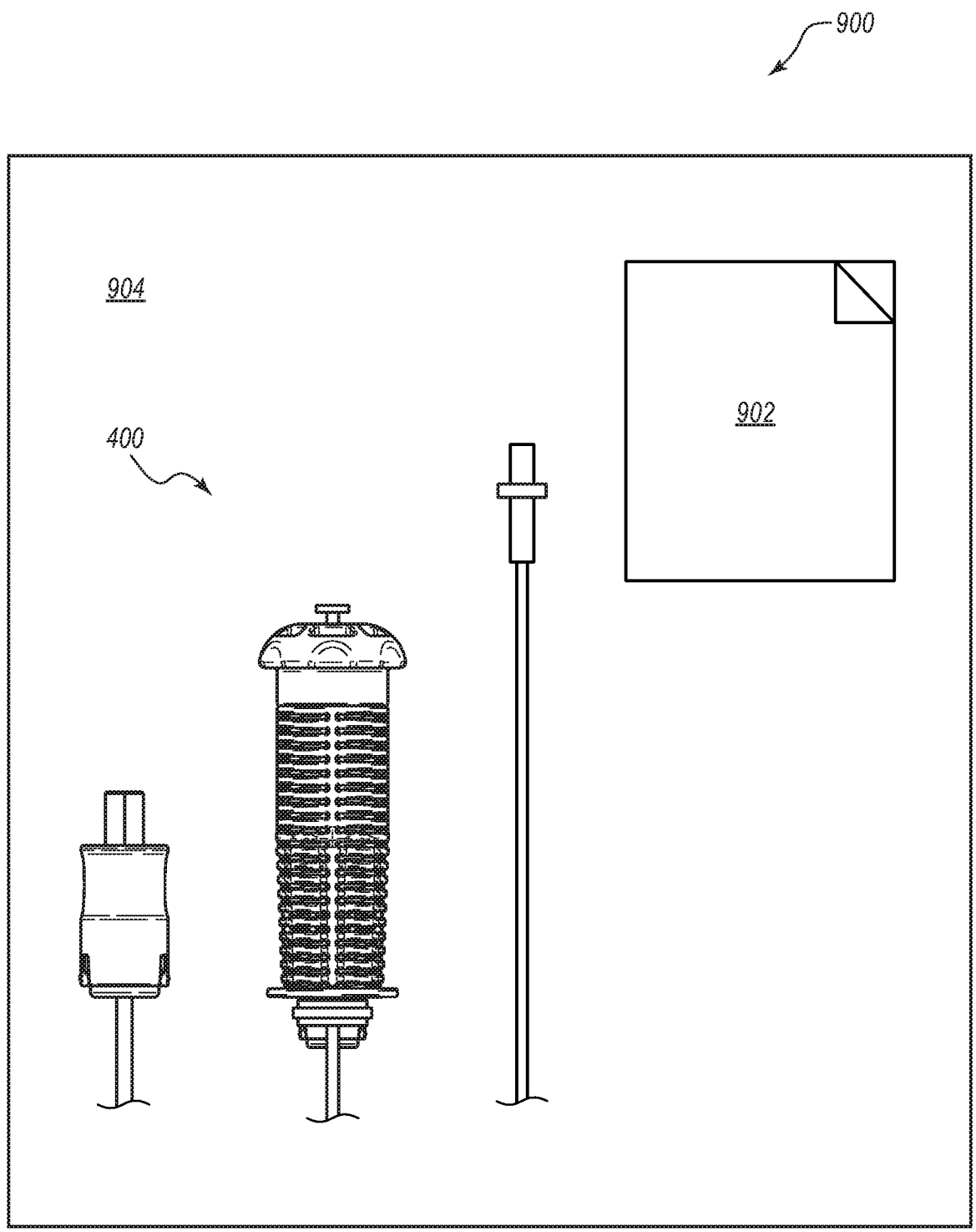
FIG. 18 is an elevation view of another embodiment of a kit that includes the system depicted in FIG. 9.

FIG. 18 depicts another embodiment of a bone biopsy kit 900, which can resemble the kit 800 in many respects. For example, the kit 900 includes instructions for use 902 and packaging 904 similar to those of the kit 800. Rather than including a drill, however, the kit 900 only includes a single-use bone biopsy system 400. Such a kit may be used by a practitioner who already possesses a reusable drill.

Each of the trocar assemblies 110, 410 and the obturator assembly 211 can also be referred to herein as a drilling insert assembly, or as an insert assembly. In some instances, such as in certain embodiments of the trocar assemblies 110, 410, the drilling insert assembly—specifically, a distal tip thereof—can at least partially contribute to cutting through the cortical layer of bone during a drilling phase. In other instances, such as in certain embodiments of the obturator assembly 211, the distal tip of the drilling insert assembly does not cut through the cortical layer of the bone during the drilling phase. In either case, the drilling insert assembly can be positioned within the cutting assembly 120, 420 during the drilling phase, or stated otherwise, when the bone biopsy system is in the power drilling configuration.

Each of the trocars 114, 414 and the obturator 215 can also be referred to herein as an elongated member or as an elongated insert. In some instances, such as in certain embodiments of the trocars 114, 414, the elongated insert extends through a full length of the cutting tube 124, 424 when the cortical drilling assembly (e.g., the cortical drilling assemblies 102, 402) is in a drilling configuration. In other instances, such as in certain embodiments of the obturator 215, a distal tip of the elongated insert can be recessed relative to a distal tip of the cutting tube 224 when the cortical drilling assembly (e.g., the cortical drilling assembly 202) is in the drilling configuration.

As previously discussed, any suitable arrangement or combination of the features discussed herein is contemplated. For example, various cutting assemblies, or features thereof, may be interchanged. Thus, while some systems may be described with respect to a cutting assembly that includes a trocar and a cutting tube, other systems may instead include an obturator and a cutting tube. Moreover, further variations are contemplated.

For example, in some embodiments, at least the cutting tip 426 of the cutting cannula 424 may be radially recessed relative to cutting surface of the trocar 414, such that only the trocar 414 cuts through the cortical layer of the bone. For example, the cutting tip 416 of the trocar 414 may include deployable and retractable cutting surfaces. The cutting surfaces can assume a high-profile arrangement to cut an opening sufficiently large for passage therethrough of the distal end of the cutting cannula 424. After the cutting cannula 424 is introduced into the marrow, the cutting surfaces can be retracted to a lower profile orientation and the trocar 414 can be removed. Thereafter, the cutting cannula 424 can core the marrow in manners such as previously discussed. Thus, in some instances, the cutting cannula 424 may only be used to cut through marrow.

As a further example, in various embodiments, any suitable number of grasping arms 147, 148, 447, 448 at the distal end of the extraction cannula 140, 440 is contemplated. For example, in various embodiments, the extraction cannula 140, 440 includes no fewer than 3, 4, 5, 6, 7, or 8 grasping arms.

In still other embodiments, the distal tip 446 of the extraction tube 444 (e.g., the distal ends of the grasping arms 447, 448) may not extend out of the cutting assembly 420 when the extraction cannula 444 is advanced distally. Rather, the distal tip 446 may remain at an interior of the cutting cannula 424. The distal end of the cutting cannula 424 may still taper inward (e.g., at a restriction, constriction, ramp, or chamfer) to cause the grasping arms 447, 448 to compress inwardly in manners such as previously discussed.

Figure 19:
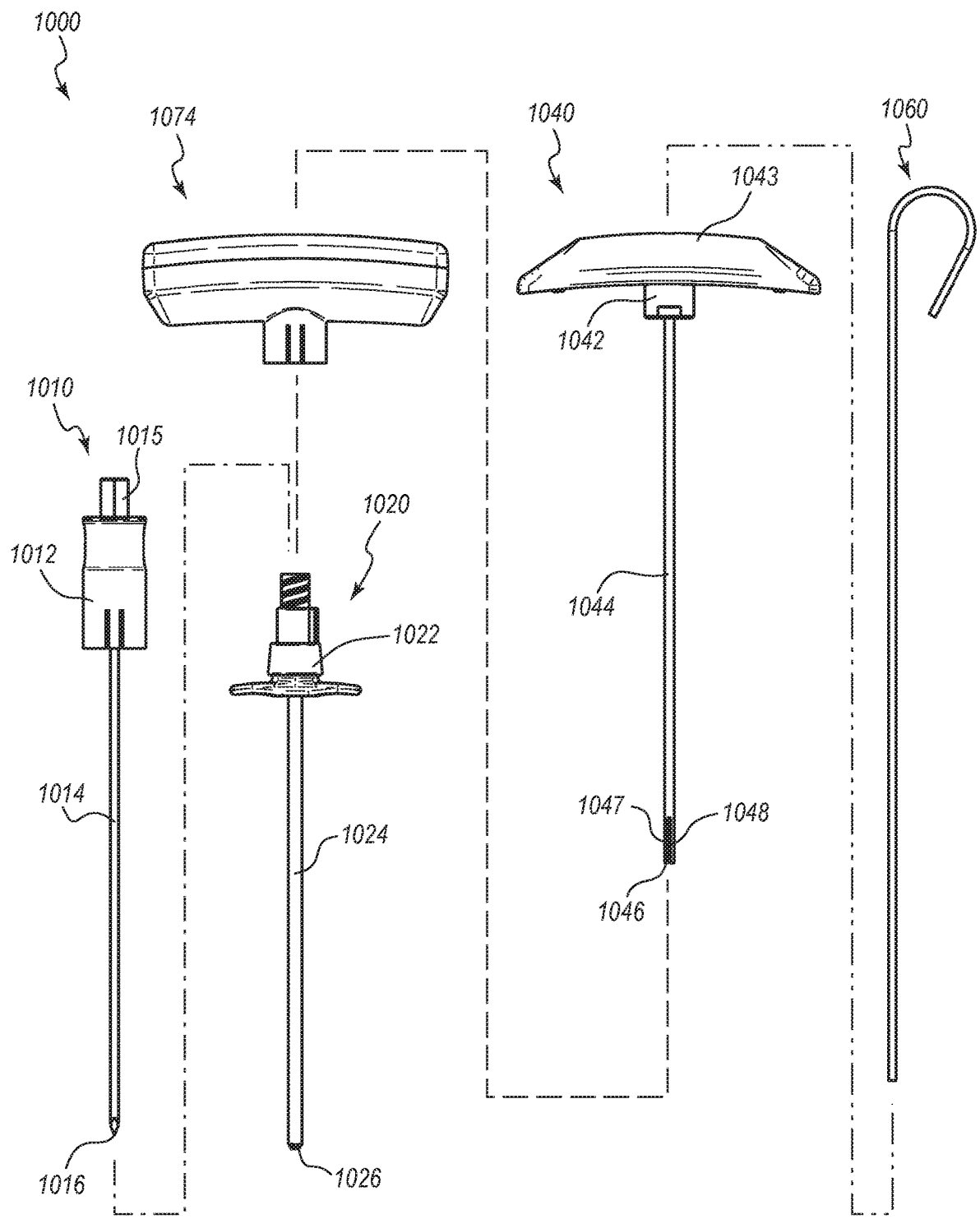
FIG. 19 is an elevation view of another embodiment of a bone biopsy system.

FIG. 19 is an elevation view of another embodiment of a bone biopsy system 1000 that resembles other bone biopsy systems disclosed herein in numerous respects. As with other systems disclosed herein, various features of the system 1000 can be used with the other systems, and vice versa.

The system 1000 can function as a hybrid system in which a powered driver (e.g., a power drill) is used to advance a cutting cannula through the cortex of a bone in a relatively rapid manner. Thereafter, the cutting cannula can be advanced manually further into the bone to gather a sample from a softer portion of the bone, or stated otherwise, from the cancellous region (e.g., for a bone marrow sample).

The bone biopsy system 1000 can include a trocar assembly 1010 (which may more generally be referred to as an elongated insert assembly), a cutting assembly 1020, a handle 1074, an extraction assembly 1040, and a push rod 1060, which may, in many respects, resemble similarly named and numbered components discussed elsewhere herein.

The trocar assembly 1010 includes a trocar hub 1012, a trocar 1014, and a sharpened cutting tip 1016 at a distal end of the trocar 1014. As with other trocar assemblies, the trocar hub 1012 can include any suitable connection interface 1015 for coupling the trocar assembly 1010 to a powered driver, such as a powered drill. In the illustrated embodiment, the connection interface 1015 comprises a proximally projecting hex-shaped post configured to securely couple to a complementarily shaped socket of a drill, such as any of the drills 172, 372, 472 previously disclosed. The post/socket arrangement can be reversed, in some embodiments, and/or any other suitable connection interfacing is contemplated.

In further embodiments, a manual driver (e.g., a separate manual driver, not shown) may selectively be used in place of the powered driver, such as in instances where little effort is required to pass through the cortex. In certain of such instances, a separate manual driver (e.g., such as the handle 1074) that includes a socket similar to that of the powered drill may be coupled to the coupling interface 1015 to effect the manual drilling.

With continued reference to FIG. 19, the cutting assembly includes a cutting cannula hub 1022, a cutting cannula 1024, and a distal cutting tip 1026 at a distal end of the cutting cannula 1024. The extraction assembly 1040 includes an extraction hub 1042, an extraction cannula 1044, and an extraction tip 1046 at a distal end of the extraction cannula 1044. As with other embodiments, the extraction tip 1046 can include a plurality of resiliently flexible grasping arms 1047, 1048 that can grip a cored sample. In the illustrated embodiment, the extraction hub 1042 further includes a transversely extending or T-shaped handle 1043. Various components of the system 1000 depicted in FIG. 19 will be described in further detail hereafter.

With reference to FIGS. 20A and 20B, the trocar hub 1012 can include a translational connection interface 1083 that is configured to secure the trocar hub 1012 to the cutting cannula hub 1022 in a manner that inhibits translational movement between the hubs 1012, 1022. In the illustrated embodiment, the connection interface 1083 comprises a pair of resilient arms 1084, each of which is configured to snap onto the cutting assembly hub 1022, as further discussed below.

FIG. 20B depicts a bottom perspective view of the trocar hub 1012. The trocar hub 1012 defines a rotational connection interface 1081 that is configured to couple in a rotationally fixed manner with a rotational connection interface of the cutting cannula hub 1022. In particular, the connection interface 1081 of the illustrated embodiment is a socket 1082. The socket 1082 can define a keyed shape that permits the cutting cannula hub 1022 to be coupled to the trocar hub 1012 in only one unique rotational or angular orientation. In particular, in the illustrated embodiment, the socket 1082 defines a substantially circular region having a recess projecting from one side. Any other suitable keying configuration is contemplated.

The trocar hub 1012 further defines a spline cavity 1085 for receiving a spline insert or spline element 1087 depicted in FIGS. 21A and 21B. The spline element 1087 defines a trocar cavity 1088 into which a proximal end of the trocar 1014 is received. The spline element 1087 can be fixedly secured to the trocar 1014 in any suitable manner (e.g., via an adhesive). Similarly, the spline element 1087 can be received into the spline cavity 1085 of the trocar hub 1012 and fixedly secured thereto in any suitable manner. The spline element 1087 can assist in transferring rotational motion, which is provided by the powered drill, from the trocar hub 1012 to the trocar 1014. Stated otherwise, the spline element 1087 can assist in maintaining a fixed rotational orientation between the trocar hub 1012 and the trocar 1014. Other spline arrangements disclosed herein can operate in similar manners. In other embodiments, the spline may be omitted.

FIG. 22 is a perspective view of an embodiment of a magnetic member 1099 that can facilitate coupling of the trocar hub 1012 with a powered driver. In the illustrated embodiment, the magnetic member 1099 is received within and fixedly coupled to a complementary recess at the upper end of the coupling interface 1015 (see FIG. 20A). The magnetic member 1099 can magnetically interact with another magnetic member within the powered driver. For example, in the illustrated embodiment, the magnetic member 1099 comprises a ferromagnetic material, such as ferromagnetic steel (e.g., 400 series stainless steel). A socket of the powered driver can either be magnetized itself or can include a magnet to attract the magnetic member 1099. In other embodiments, the magnetic member 1099 can comprise a magnet and the socket can comprise a ferromagnetic material to which the magnet is attracted.

FIG. 23 is an elevation view of the cutting tip 1016 at the distal end of the trocar 1014. In the illustrated embodiment, the cutting tip 1016 includes three substantially equal facets that come to a point. Any other suitable cutting arrangement is contemplated. Moreover, as with other embodiments described herein, the trocar 1014 may more generally be referred to as an elongated insert or elongated element.

Figure 24A:
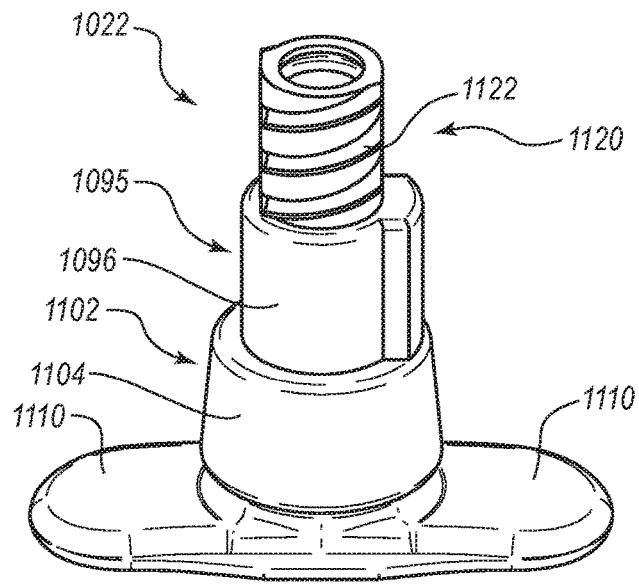
FIG. 24A is an upper perspective view of an embodiment of a hub compatible with an embodiment of a cutting assembly of the bone biopsy system of FIG. 19.
Figure 24B:
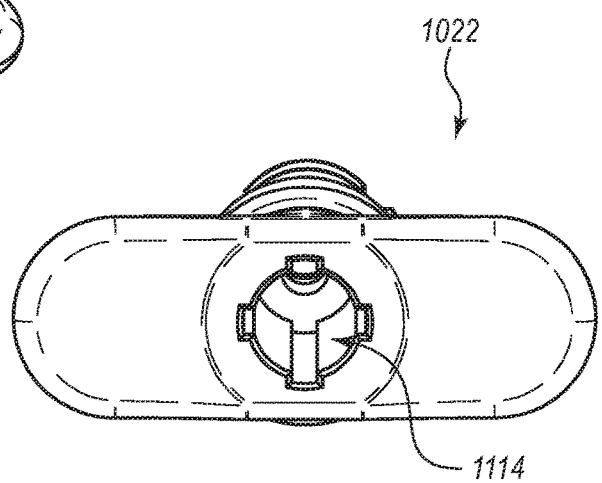
FIG. 24B is a lower perspective view of the hub.

With reference to FIGS. 24A and 24B, the cutting cannula hub 1022 can resemble the cutting cannula hub 422 discussed above in many respects. For example, the cutting cannula hub 1022 includes a rotational connection interface 1095 configured to couple with the rotational connection interface 1081 of the trocar hub 1012 in a rotationally fixed manner. In particular, the connection interface 1095 comprises a keyed post 1096 that is complementary to the socket 1082 of the trocar hub 1012.

The cutting cannula hub 1022 further includes a translational connection interface 1102, which in the illustrated embodiment, comprises a frustoconical collar or protrusion 1104 that extends laterally outward at the base of the rotational connection interface 1081. The translational connection interface 1083 of the trocar hub 1012 can couple with the translational connection interface 1102 of the cutting cannula hub 1022 in any suitable manner. In the illustrated embodiment, the resilient arms 1084 of the trocar hub 1012 snap over the protrusion 1104 and engage a distal surface thereof. Although the snapping arrangement is not specifically shown between the resilient arms 1084 and the protrusion 1104, a similar interaction is shown between a similar set of resilient arms and the connection interface 1102 in FIG. 34C.

The cutting cannula hub 1022 can further include a pair of finger rests or wings 1110 that extend laterally outward in opposite directions from a base of the connection interface 1083. As discussed further below, the wings 1110 can facilitate removal of the cutting cannula hub 1022 from the bone after a sample has been gathered. Each wing 1110 can extend outwardly from an outer surface of the cutting cannula 1024 by a sufficient amount to permit at least one finger of a practitioner to rest on an underside thereof. A practitioner thus may position at least one finger at the underside of each wing 1110—that is, on opposite sides of the cutting cannula 1024—and pull proximally to remove the cutting cannula 1024 from the bone.

Figure 25A:
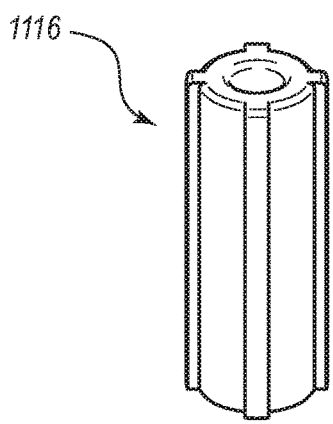
FIG. 25A is an upper perspective view of an embodiment of a spline element compatible with the hub of FIG. 24A.
Figure 25B:
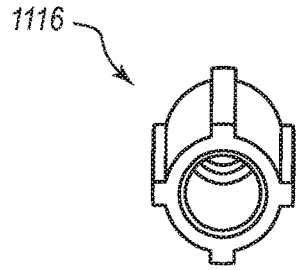
FIG. 25B is a lower perspective view of the spline element.
Figure 27B:
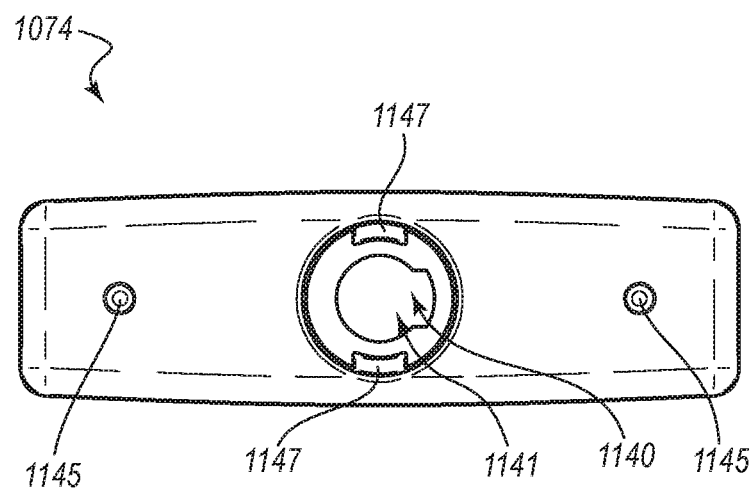
FIG. 27B is a top plan view of the handle.
Figure 27C:
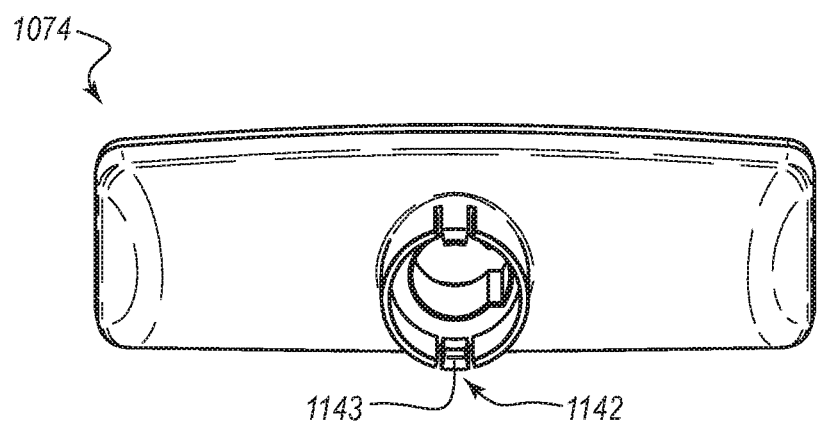
FIG. 27C is a lower perspective view of the handle.
Figure 27D:
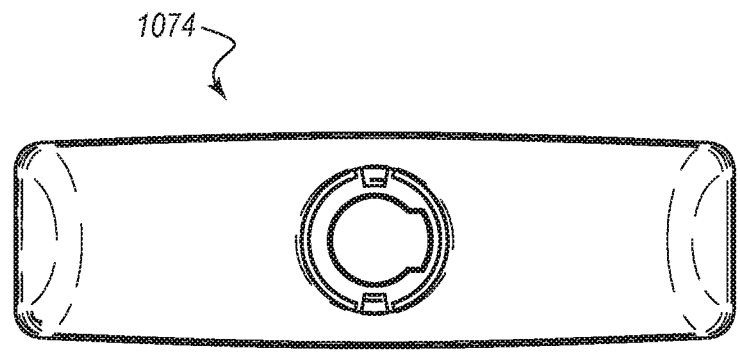
FIG. 27D is a bottom plan view of the handle.

The illustrated cutting cannula hub 1022 further includes a spline cavity 1114, which can receive the spline element 1116 depicted in FIGS. 25A and 25B. As with other spline arrangements depicted herein, the spline element 1116 can assist in maintaining a fixed rotational orientation between the cutting cannula hub 1022 and the cutting cannula 1024.

With further reference to FIG. 24A, as with other embodiments herein, the cutting cannula hub 1022 includes a medical connector 1120, which in the illustrated embodiment, comprises a Luer fitting 1122. Any suitable medical device can be coupled to the medical connector 1120, such as to aspirate fluid from within the bone after the cutting cannula 1024 has been introduced into an interior thereof. In the illustrated embodiment, the Luer fitting 1122 extends proximally from the keyed post 1096.

FIGS. 26A and 26B depict the distal end of the cutting cannula 1024. In the illustrated embodiment, the distal end includes a constriction 1025 that reduces an inner diameter of the cutting cannula 1024. In particular, in this embodiment, the constriction 1025 comprises a small length of an inner cannula 1126 that is spot welded to an inner surface of a primary outer cannula 1128. The inner cannula 1126 includes an angled surface, deflection surface, ramp, or chamfer 1130 at an upper end thereof. As further discussed below, the chamfer 1130 can interact with the resilient arms 1047, 1048 at the distal end of the extraction assembly 1040 to urge the arms 1047, 1048 inward to grip a cored sample.

As the cutting cannula 1024 is advanced in a distal direction through the bone, the resulting cored sample is advanced proximally within a lumen 1132 of the cutting cannula 1024. As previously noted, in some instances, the extraction assembly 1040 can be advanced distally through the cutting cannula 1024 to encompass the sample, and the angled surface of the chamfer 1130 can urge the resilient arms 1047, 1048 inward to grasp and retain the cored sample. Thus, the chamfer 1130 can advantageously cooperate with the extraction assembly 1040 to facilitate grasping a cored sample and/or breaking the cored sample free.

In some instances, the cored sample naturally expands laterally outwardly, at least somewhat, as the sample is advanced into the lumen 1132 proximally past the upper end of the inner cannula 1126. The expansion may, in further instances, be sufficient such that the chamfer 1130 is able to independently retain the sample within the lumen. For example, the cutting cannula 1024 may be rotated to break away the sample, and the sample may thereafter be retained in the cutting cannula 1024 due to the interaction of the chamfer 1130 with the distal end of the sample. Accordingly, in some instances, the sample may be retained within the cutting cannula 1024 without using the extraction assembly 1040. In certain of such instances, the cored sample may be removed from the cutting cannula 1024 in manners such as described below with respect to the system 1300 depicted in FIG. 37.

With continued reference to FIGS. 26A and 26B, in the illustrated embodiment, the distal cutting tip 1026 includes facets 1027 that yield sharpened edges and points that facilitate drilling into bone. The illustrated embodiment includes six facets 1027, although other numbers and arrangements are contemplated. The facets 1027 extend along the distal faces of both the inner and outer cannulas 1126, 1128.

FIGS. 27A-27D depict various views of the handle 1074. The handle 1074 is configured to be coupled to the cutting cannula hub 1022 and to impart both translational (i.e., in the distal direction) and rotational movement thereto. The rotational movement can be in both clockwise and counterclockwise directions.

The handle 1074 can define any suitable shape or configuration, and may desirably be ergonomic for ready manipulation by a single hand. In the illustrated embodiment, the handle 1074 is substantially elongated in a lateral direction, relative to an axis of rotation thereof. The handle 1074 substantially defines a T-shape. The handle 1074 is formed of two separate molded pieces joined together. Any other suitable arrangement and manufacturing method is contemplated.

The handle 1074 includes a rotational coupling interface 1140 and a translational coupling interface 1142, similar to the like-named coupling interfaces 1081, 1083 of the trocar hub 1012. In particular, the rotational coupling interface 1140 comprises a keyed socket 1141 and the translational coupling interface 1142 comprises a pair of resilient arms 1143.

The handle 1074 can include a temporary attachment mechanism for selectively securely attaching with the extraction hub 1042. Any suitable coupling mechanism is contemplated. In the illustrated embodiment, the handle 1074 includes a pair of divots 1145 and a pair of inward protrusions 1147. The divots 1145 are recessed relative to a top surface of the handle 1174. The protrusions 1147 extend radially inward at opposite sides of a cavity at the upper end of the handle 1174.

Figure 28A:
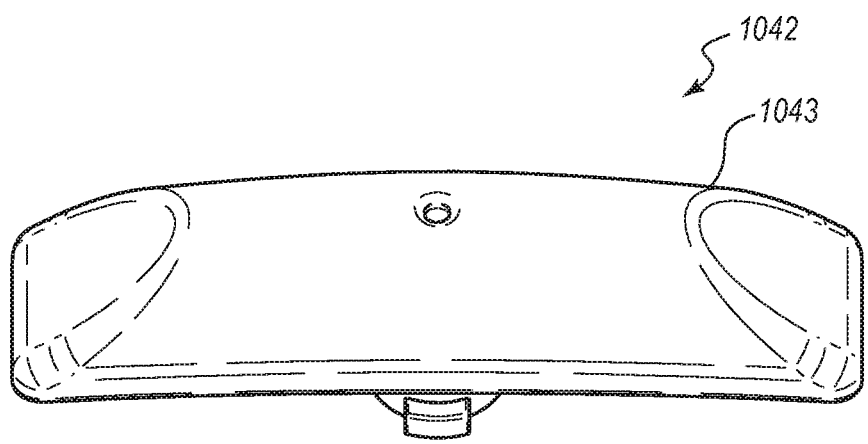
FIG. 28A is an upper perspective view of an embodiment of a hub compatible with an embodiment of an extraction assembly of the bone biopsy system of FIG. 19.
Figure 28B:
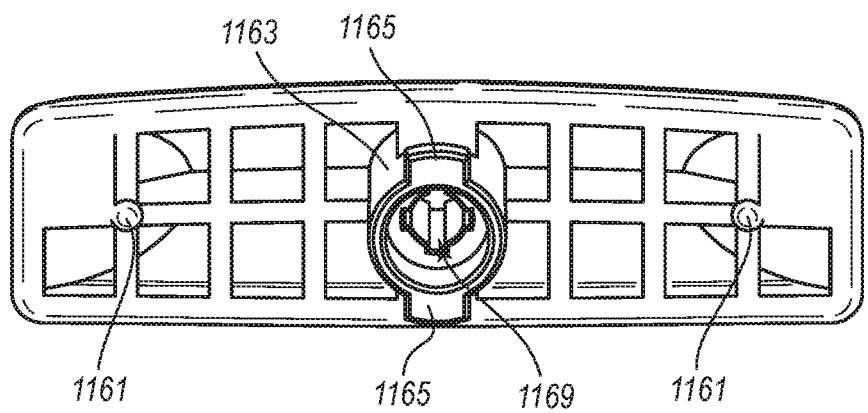
FIG. 28B is a lower perspective view of the hub of FIG. 28A.
Figure 34B:
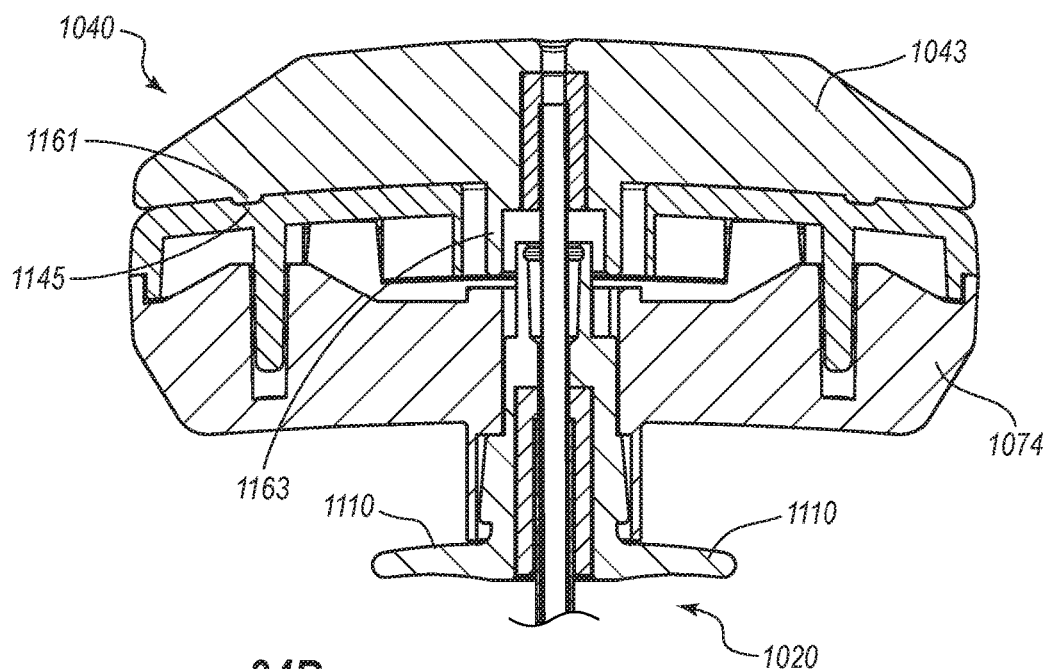
FIG. 34B is a cross-sectional view of the extraction assembly coupled with the cutting assembly taken along the view line 34B-34B in FIG. 34A.
Figure 34A:
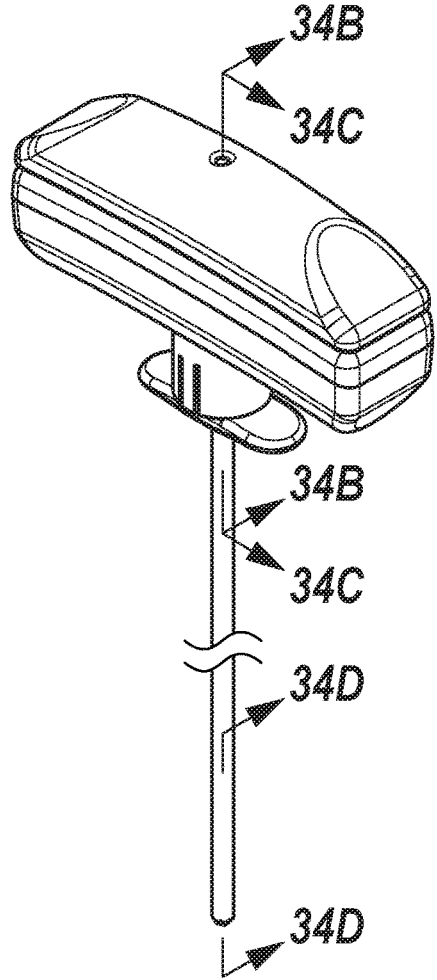
FIG. 34A is a perspective view of the extraction assembly coupled with the cutting assembly.
Figure 34C:
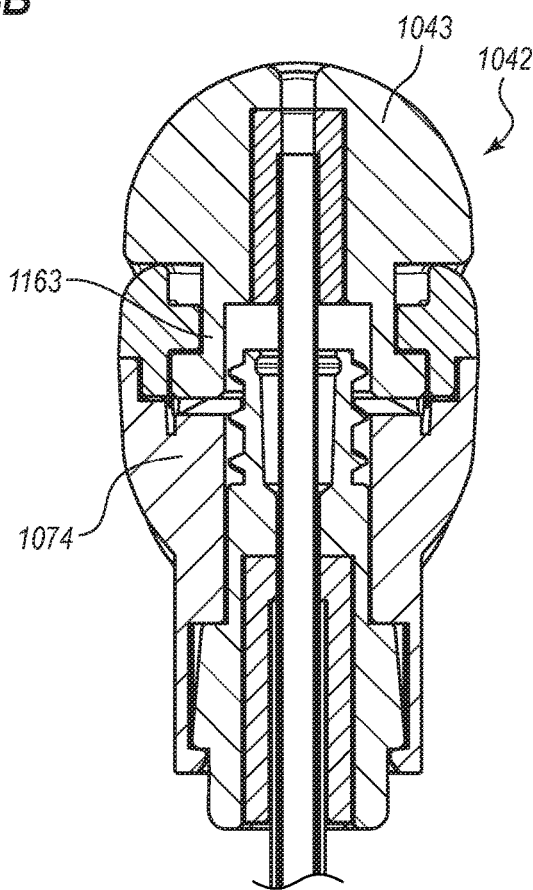
FIG. 34C is a cross-sectional view of the extraction assembly coupled with the cutting assembly taken along the view line 34C-34C in FIG. 34A.

With reference to FIGS. 28A and 28B, the extraction hub 1042 includes a temporary attachment mechanism complementary to that of the extraction hub 1042. In particular, the handle 1043 of the extraction hub 1042 includes a pair of detents 1161 at an underside thereof that are configured to seat within the divots 1145 of the handle 1074 when proper rotational and longitudinal alignment is achieved, as shown in FIG. 34B. The extraction hub 1042 further includes a distally extending post 1163 sized to fit within the upper cavity of the handle with two diametrically opposed protrusions 1165 extending outwardly therefrom. The outward protrusions 1165 are configured to seat underneath the inward protrusions 1147 of the handle 1074 when the handle 1043 portion of the extraction hub 1042 is rotated into alignment with the handle 1074, as shown in FIG. 34C.

Figure 29A:
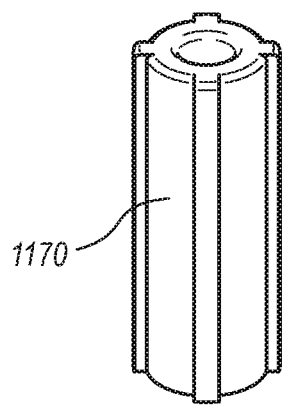
FIG. 29A is an upper perspective view of an embodiment of a spline element compatible with the hub of FIG. 28A.
Figure 29B:
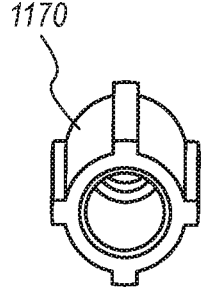
FIG. 29B is a lower perspective view of the spline element.

The extraction hub 1042 can include a spline cavity 1169 for receiving a spline element 1170 therein. The spline element 1170 is depicted in FIGS. 29A and 29B.

Figure 30:
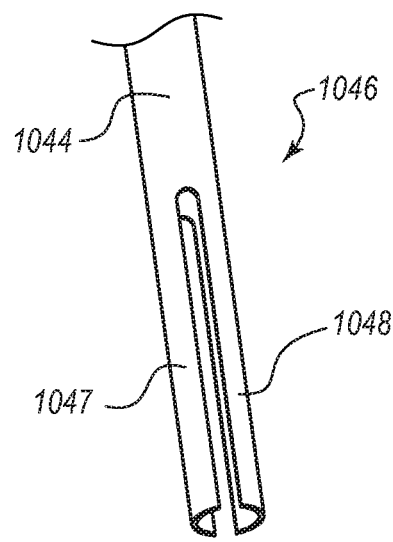
FIG. 30 is a perspective view of a distal end of an extraction cannula of the extraction assembly.

FIG. 30 depicts the distal end 1046 of the extraction cannula 1044. The resilient arms 1047, 1048 can function in manners substantially such as previously described with respect to, for example, the arms 147, 148.

Figure 31A:
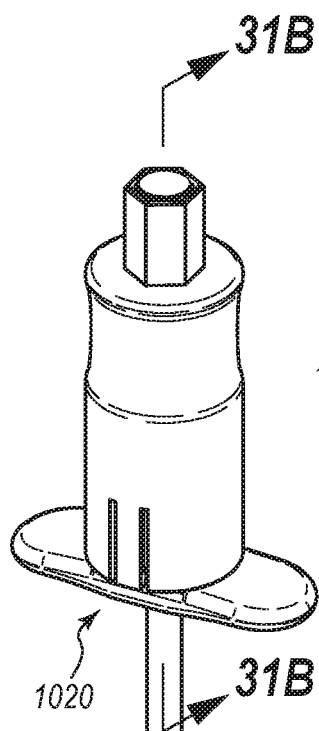
FIG. 31A is a perspective view of the trocar assembly and the cutting assembly of the system of FIG. 19 in a coupled configuration, such as may be used to drill through cortical bone.
Figure 31B:
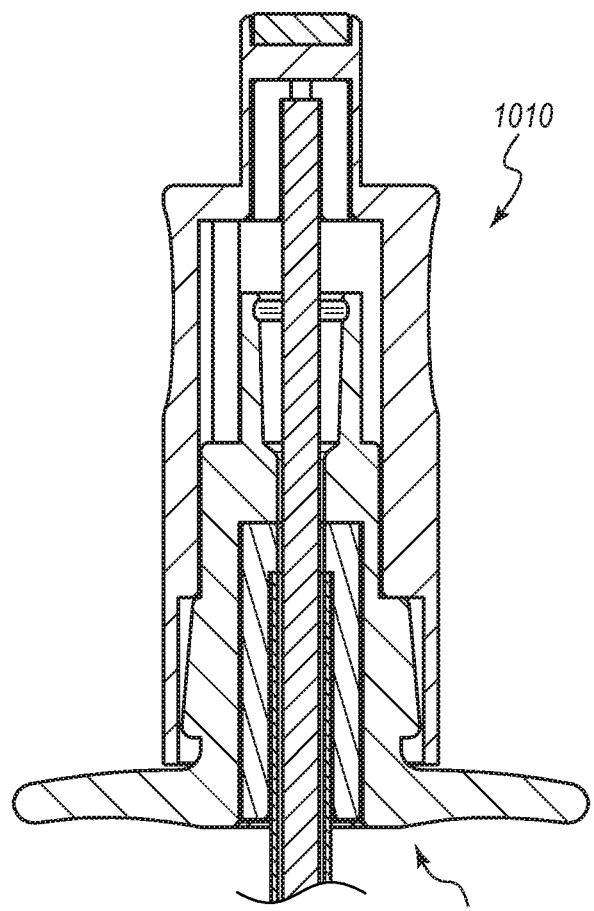
FIG. 31B is a cross-sectional view of the trocar assembly coupled with the cutting assembly taken along the view line 31B-31B in FIG. 31A.
Figure 31C:
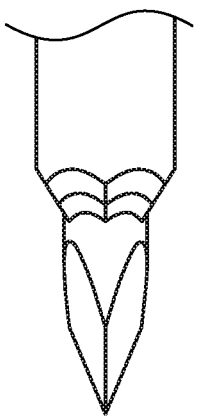
FIG. 31C is a perspective view of a distal end of the trocar assembly and the cutting assembly in the coupled configuration.

Illustrative examples of methods of using the bone biopsy system 1000 will now be described with respect to FIGS. 31A-35. As shown in FIGS. 31A-31C, in some embodiments, a bone biopsy procedure begins with the trocar assembly 1010 and the cutting assembly 1020 in the assembled state. The assemblies 1010, 1020 may either be provided in a pre-assembled state (e.g., may be prepackaged in this configuration), or the user may couple the assemblies together as an early stage in the procedure. Coupling the trocar assembly 1010 and the cutting assembly 1020 in this manner may be referred to as placing the bone biopsy system 1000 in a power drilling configuration.

The trocar hub 1012 is then coupled to a driver. In many instances, the driver is a powered driver (e.g., a drill). The powered driver is actuated or energized and the user urges the system distally into the bone. The distal ends of the trocar and the cutting cannula drill through the cortical layer of the bone. Once the distal tip of the cutting cannula has passed through the cortical layer, the operator can deenergize the powered driver. The user may know that the interior of the bone has been reached, for example, when drilling becomes easier.

While leaving the cutting assembly 1020 in place with the cutting cannula 1022 lodged in the bone, the trocar assembly 1010 can be removed from the cutting assembly. The user can steady the cutting assembly in any suitable manner while the operator draws the trocar assembly proximally from the cutting assembly. The resilient arms or catches 1084 of the trocar hub 1012 (see FIG. 20A) may, in some embodiments, be configured to readily release from the cutting cannula hub 1022 in manners such as previously described with respect to other embodiments.

Figures 32, 33A:
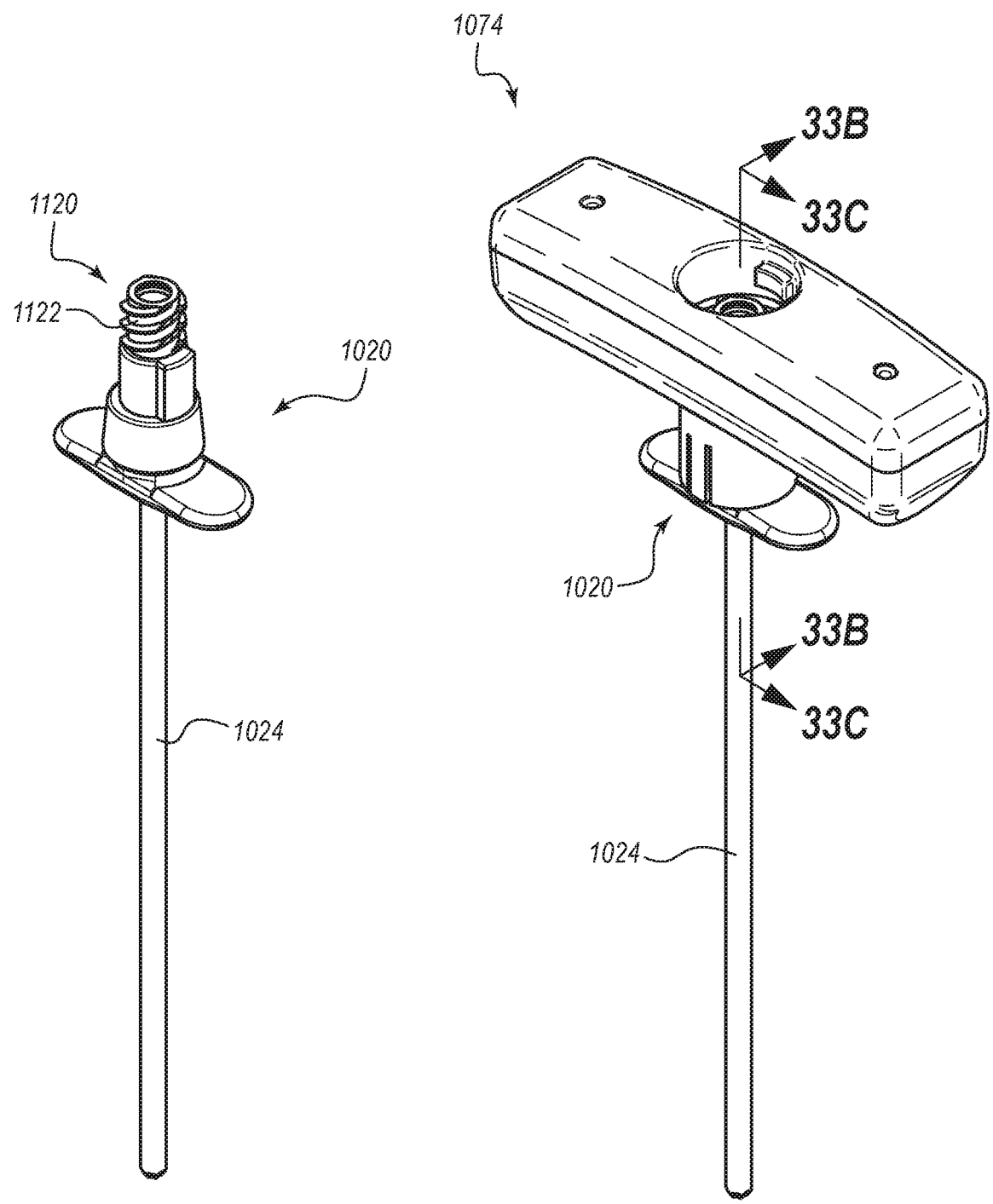
FIG. 32 is a perspective view of the cutting assembly after the trocar assembly has been removed therefrom.
FIG. 33A is a perspective view of the handle of FIGS. 27A-27D coupled with the cutting assembly.

FIG. 32 depicts the cutting assembly 1020 after the trocar assembly 1010 has been withdrawn therefrom. The medical connector 1120 (e.g., the Luer fitting 1122) is accessible in this configuration. If desired, any suitable medical device can be coupled to the medical connector, such as for aspiration through the cutting cannula 1024. In some instances, an extension tube may be coupled to the connector 1120 to facilitate the aspiration process.

Figure 33B:
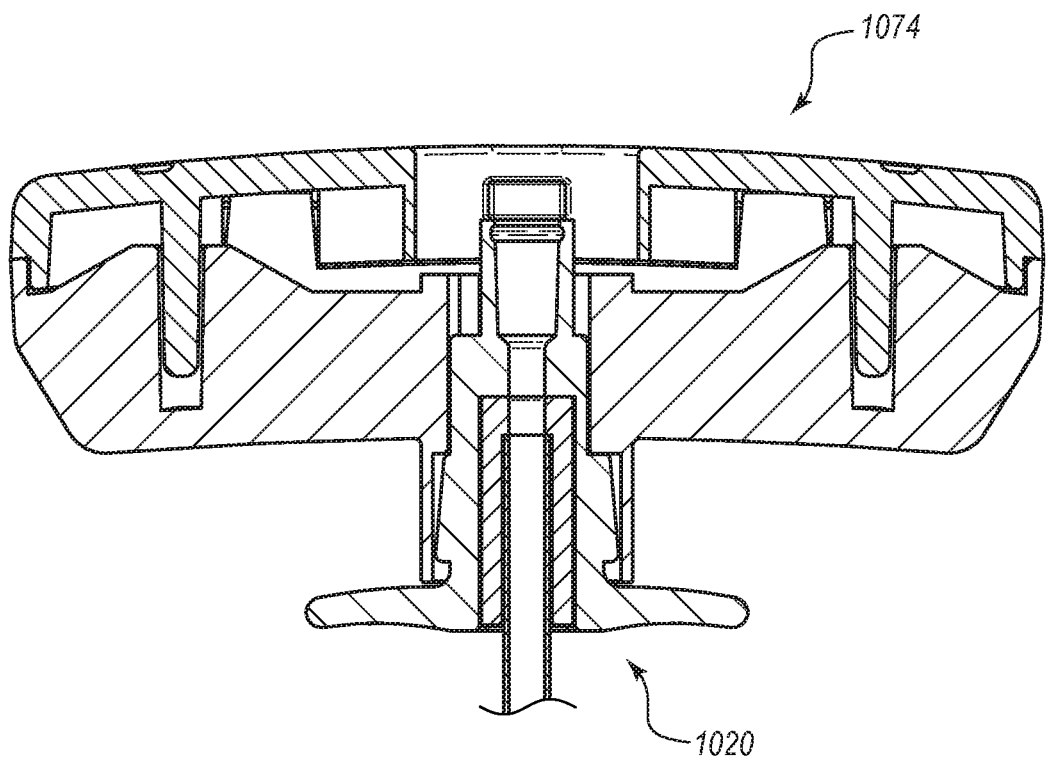
FIG. 33B is a cross-sectional view of the handle coupled with the cutting assembly taken along the view line 33B-33B in FIG. 33A.
Figure 33C:
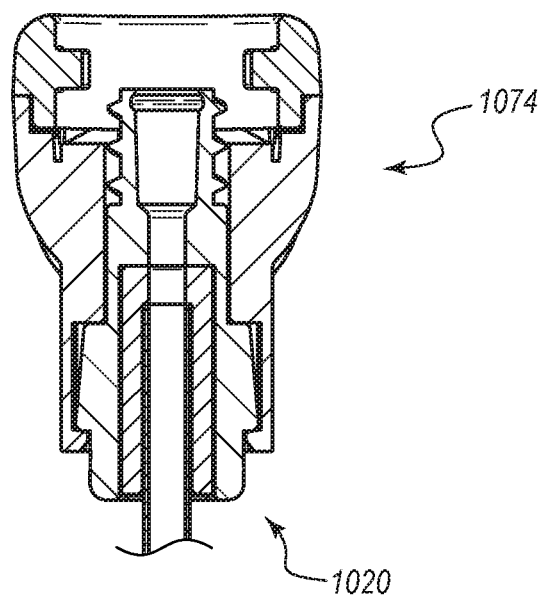
FIG. 33C is a cross-sectional view of the handle coupled with the cutting assembly taken along the view line 33C-33C in FIG. 33A.

With reference to FIGS. 33A-33C, the handle 1074 can be coupled to the cutting assembly 1010. This may be referred to as a manual coring configuration of the system 1000. The user can manually manipulate the handle 1074, such as by pressing in a distal direction while rotating the handle 1074 about a longitudinal axis of the cutting cannula 1024. In some instances, the rotation may be back and forth in opposite directions (i.e., clockwise and counterclockwise). The user can urge the cutting cannula 1024 into the bone to a desired depth. In some instances, the cutting cannula 1024 includes depth markings, which can facilitate determination of a depth to which the cutting cannula 1024 has been advanced. The cutting action of the cutting cannula 1024 cores a sample from the interior of the bone, as previously discussed. The cored sample advances proximally into the lumen of the cutting cannula 1024 as the cutting cannula 1024 is advanced distally, as previously discussed. In some instances, the cored sample expands radially outwardly as it passes proximally past the chamfer 1130 (see FIG. 26B).

Figure 34D:
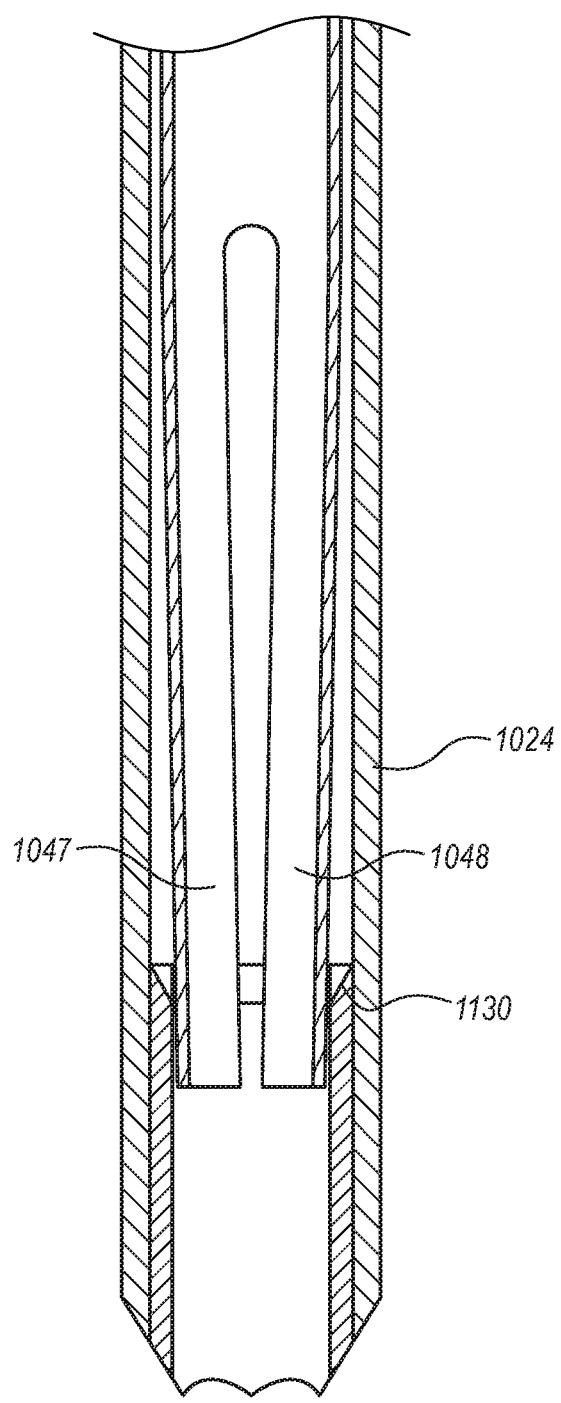
FIG. 34D is a cross-sectional view of a distal end of the extraction assembly coupled with the cutting assembly taken along the view line 34D-34D in FIG. 34A.

With reference to FIGS. 34A-34D, the extraction assembly 1040 can be inserted into the cutting assembly 1020 to retrieve the cored sample. As shown in FIG. 34D, the inner chamfer 1130 of the cutting cannula 1024 can urge the resilient arms 1047, 1048 inward to grip the sample (see also FIG. 5E).

In some embodiments, the handle portion 1043 of the extractor hub 1042 is pushed down into contact with the upper surface of the handle 1074 to urge the arms 1047, 1048 inward by the amount shown in FIG. 34D. In this orientation, the arms 1047, 1048 can have a good grip on the sample. In order to initially seat the post 1163 of the extractor assembly 1040 fully into the upper cavity of the handle 1074, the outward projections 1165 from the post must be misaligned relative to the inward projections 1147 of the handle 1074. In some instances, once the post 1163 has bottomed out in this manner, the handle portion 1043 of the extractor hub 1042 is rotated relative to the handle 1074 to securely couple these elements together by engaging the detents 1161 and the divots 1145. In some instances, a secured connection between the handles 1043, 1074 can be desirable or removing the extractor assembly and the cutting assembly in unison. In rotating the extractor assembly 1040 into the locked orientation relative to the cutting assembly 1020 while the arms 1047, 1048 are in the constricted orientation depicted in FIG. 34D, the sample, which is thus gripped by the arms, can be rotated relative to the cutting cannula 1024. Stated otherwise, the arms 1047, 1048 rotate the captured sample relative to the cancellous bone structure from which the sample has been cored as the extractor assembly 1040 is rotated into a locked orientation. In some instances, this may break the core sample away from the remaining bone structure. Accordingly, in some instances, the locking arrangement of the handles 1043, 1074 can encourage a user to twist the gripped cored sample and break it free from the remaining bone structure to which it is attached. This can facilitate extraction of the cored sample.

In some embodiments, once the handles 1043, 1074 are locked together, the user can grasp the handle 1043 (e.g., can rest the palm against the handle 1043), the handle 1074 (e.g., may wrap fingers around the handle 1074), and the wings 1110 (e.g., may wrap fingers around the underside of the wings 1110) and pull upward to withdraw the system from the patient. The user may twist the system back and forth about a longitudinal, rotational axis thereof while pulling proximally to assist in the removal. After the cutting assembly 1020 and the extraction assembly 1040 have been removed in unison in this manner, they can be separated from each other by again twisting the handles 1043, 1074 out of the locked orientation and by retracting the extraction assembly 1040 from the cutting assembly 1020.

In other instances, a user may remove the extraction assembly 1040 from the cutting assembly 1020 prior to removing the cutting assembly 1020 from the patient. For example, the user may unlock the handle 1043 from the handle 1074 by twisting the handle 1043, and may then withdraw the extraction assembly 1040 from the cutting assembly 1020. The user may then remove the cutting assembly 1020 from the patient by grasping the handle 1074 (e.g., with the palm) and the wings 1110 (e.g., by wrapping two or more fingers under the wings 1110).

Figure 35:
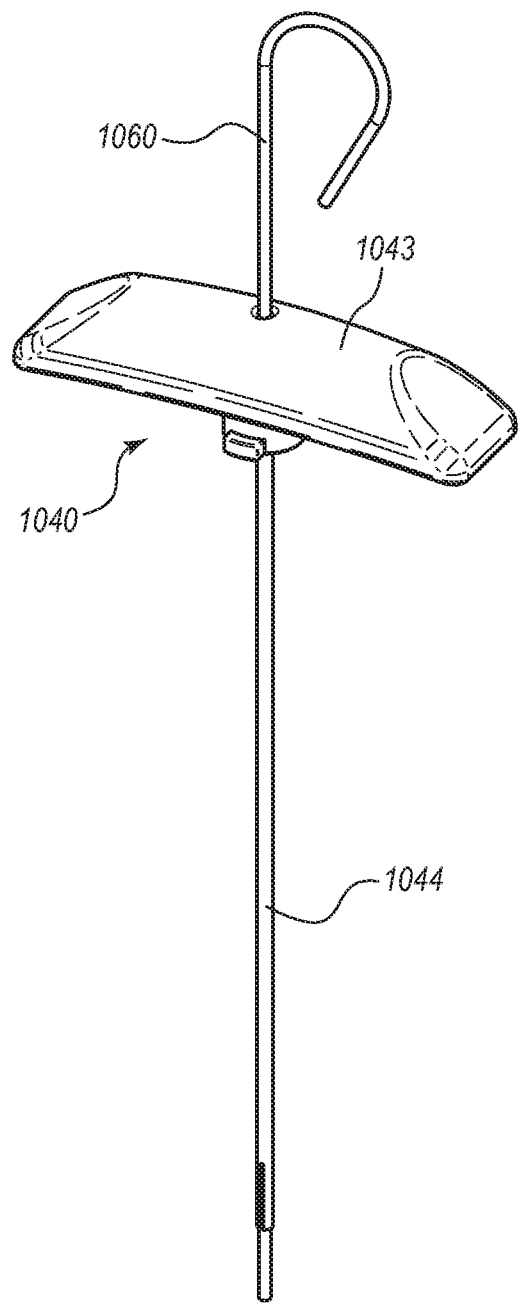
FIG. 35 is a perspective view of an embodiment of a push rod that has been inserted through the extraction assembly to clear a cored sample therefrom.

FIG. 35 depicts a later stage in an illustrative method after the extraction assembly 1040 has been removed from the cutting assembly 1020. In order to remove the cored sample from the extraction cannula 1044, the push rod 1060 is advanced distally through a channel defined by the handle 1043 and through a lumen defined by the extraction cannula 1044 to push the sample out the distal end of the extraction cannula 1044.

Figure 36:
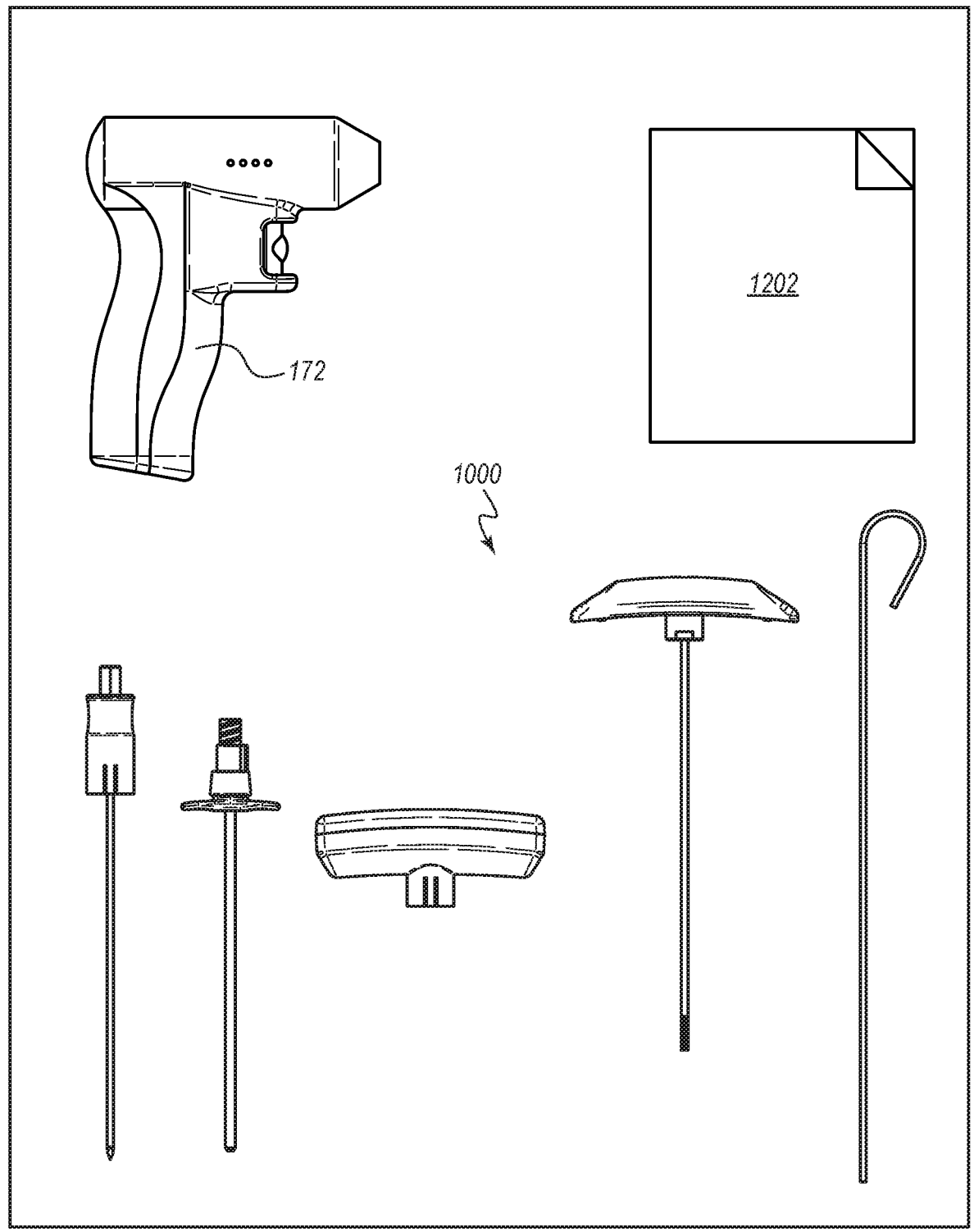
FIG. 36 is an elevation view of an embodiment of a kit that includes a powered driver and the bone biopsy system of FIG. 19.

FIG. 36 is an elevation view of an embodiment of a kit 1200 that includes a powered driver 172 and the bone biopsy system 1000. The kit 1200 further includes instructions for use 1202, which may provide directions with respect to any of the methods or processes disclosed herein. The instructions for use 1202 can resemble the instructions for use 802, 902, such as with respect to being approved by a regulatory agency. In other embodiments, the powered driver 172 is omitted from the kit. More or fewer items may be included in the kit. Moreover, in various embodiments, the system 1000 may be replaced with any other system disclosed herein, and the instructions for use 1202 can provide directions with respect to any of the methods or processes disclosed herein with respect that system. Thus, for example, any of the systems disclosed hereafter may likewise be included in a kit that includes instructions for use, which instructions provide directions with respect to any of the processes disclosed herein that are applicable to that system.

Figure 37:
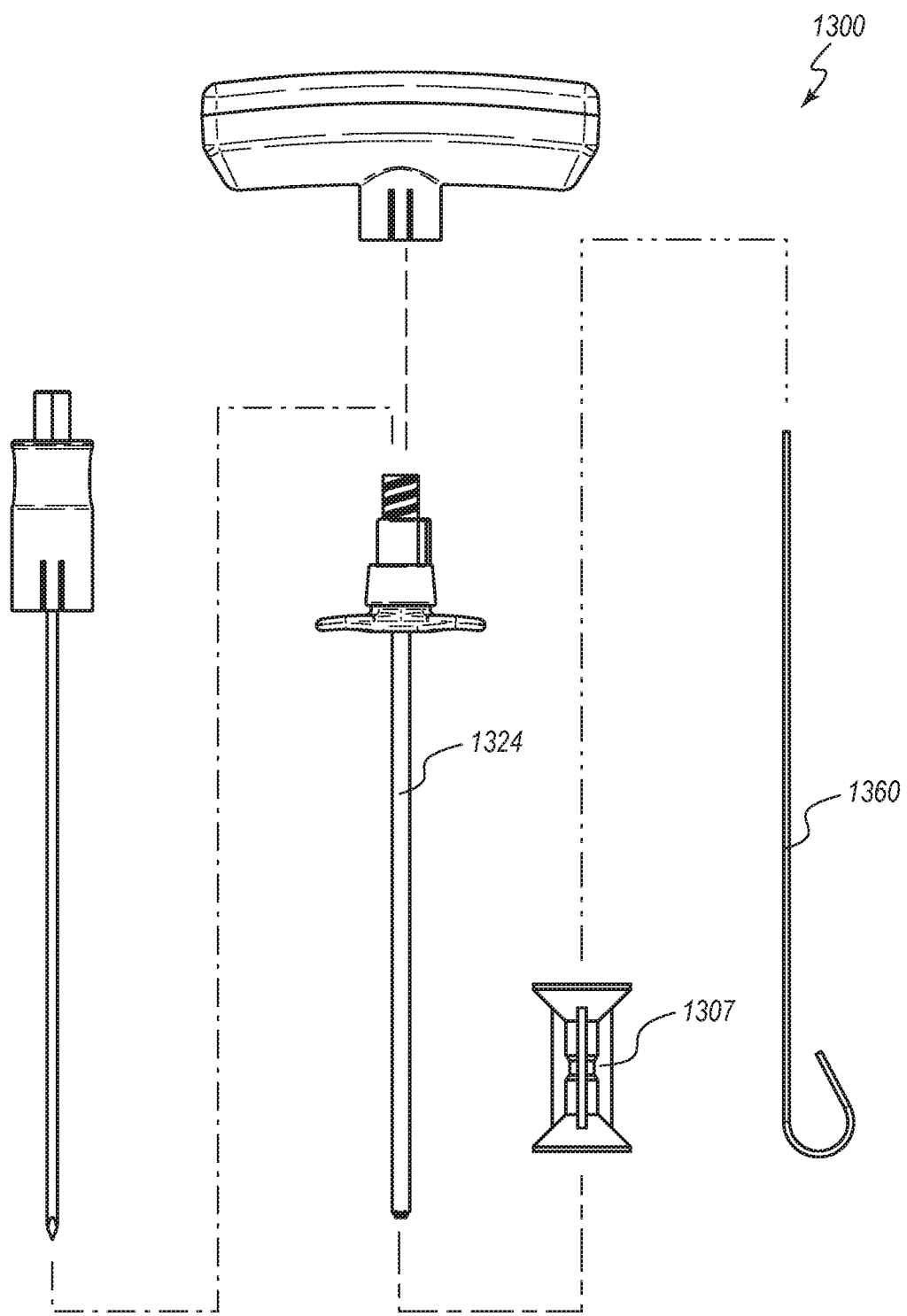
FIG. 37 is an elevation view of another embodiment of a bone biopsy system similar to the bone biopsy system of FIG. 19 that does not include an extraction assembly, but includes a differently configured cutting cannula and an embodiment of a guide.

FIG. 37 is an elevation view of an embodiment of a bone biopsy system 1300 that resembles the bone biopsy system 1000 in many respects. The bone biopsy system 1300 differs from the bone biopsy system 1000 illustrated in the drawings, however, in that the system 1300 does not include an extraction assembly. Instead, a distal end of a cutting cannula 1324 is configured to retain a cored sample within the cutting cannula 1324, and the cored sample can be removed by urging the sample proximally through the cutting cannula 1324 via a pushing rod 1360. Further, the system 1300 includes a guide 1307 configure to assist in advancing a tip of the pushing rod 1360 through the distal end of the cutting cannula 1324.

FIG. 38 is a cross-sectional view of a distal end of the cutting cannula 1324, similar to the view depicted in FIG. 26B. Rather than being chamfered, a proximal end, proximal surface, or upper surface 1431 of an inner cannula 1426 is substantially squared. For example, the upper surface 1431 of the inner cannula 1426 can define an angle relative to a longitudinal axis of the cutting cannula 1324 that is within a range of from about 70 to about 110 degrees. In the illustrated embodiment, the angle is substantially 90 degrees.

As a cored sample advanced proximally into the cutting cannula 1324, it may expand slightly as it moves past the upper surface 1431 of the inner cannula 1426. The sample may catch on the upper surface 1431 as the cutting cannula 1324 is removed from the bone, thus remaining in the cutting cannula 1324.

Figure 40A:
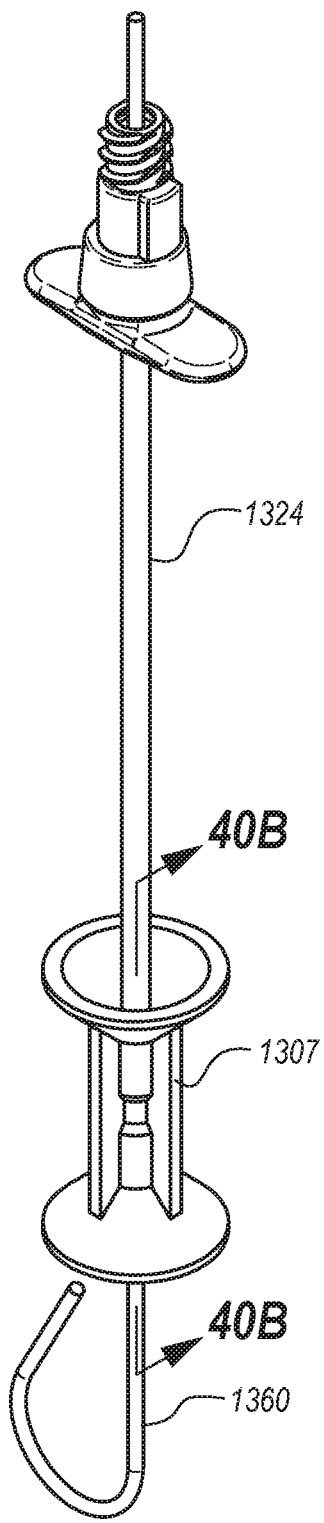
FIG. 40A is a perspective view of a push rod that has been inserted through the cutting assembly to clear a cored sample therefrom.
Figure 40B:
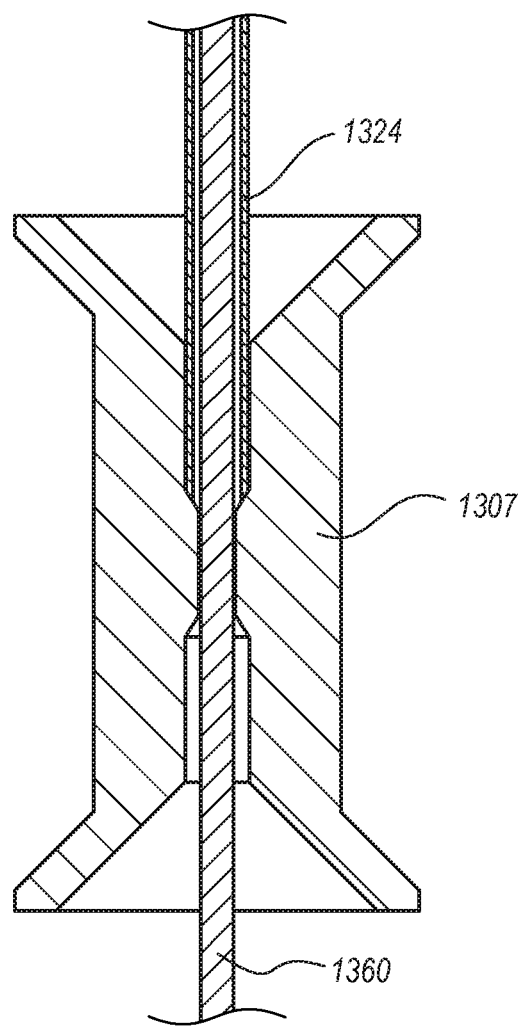
FIG. 40B is a cross-sectional view depicting an operational relationship among the guide, the push rod, and the cutting assembly, taken along the view line 40B-40B in FIG. 40A.

The guide 1307 can include a funnel at either end and an inner channel that narrows at a center thereof. Any suitable arrangement is contemplated for assisting in threading the pushing rod 1360 into the distal end of the cutting cannula 1324. The guide can inhibit inadvertent sticking from the distal end of the cutting cannula 1324. Operation of the guide 1307 is apparent from the foregoing and from FIGS. 40A and 40B.

Use of the system 1300 can proceed substantially the same as for the system 1000 with respect to many of the stages of operation. However, rather than inserting an extraction assembly into the cutting cannula 1324 to assist in retrieving the cored sample, the cutting cannula 1324 may instead be manipulated (e.g., rotated about the longitudinal axis and/or pivoted about the entry hole into the bone) to separate the cored sample from the remaining bone material. The cutting cannula 1324 is then removed from the patient with the cored sample therein, the guide 1307 placed on the distal end of the cutting cannula 1324, and the push rod 1360 is then advanced through the guide 1307 and through the cutting cannula 1324 in the proximal direction to urge the sample out of the cutting cannula 1324.

Figure 41A:
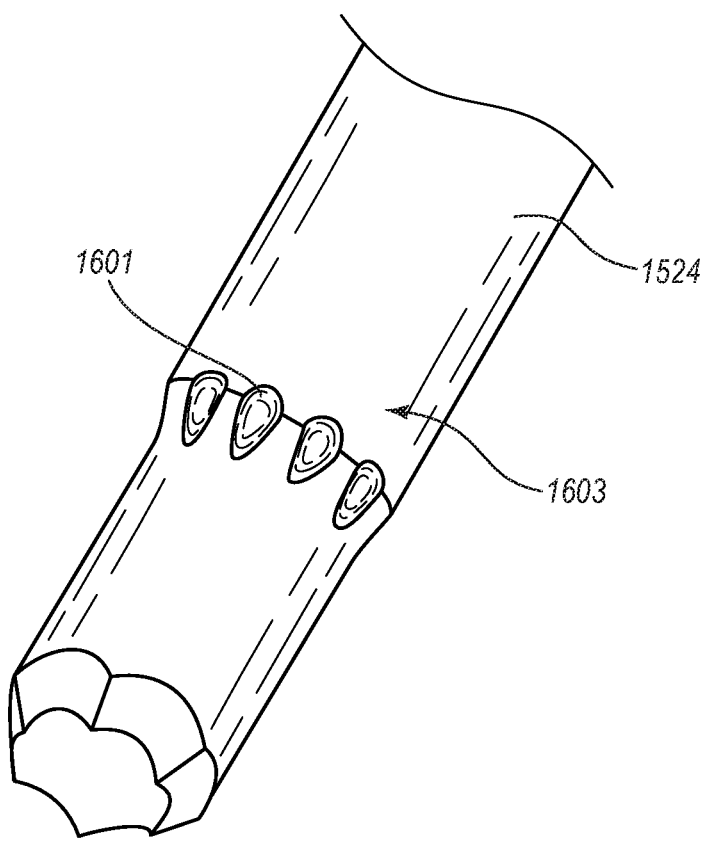
FIG. 41A is a perspective view of a distal end of another embodiment of a cutting cannula compatible with certain embodiments of bone biopsy systems disclosed herein.

FIG. 41A is a perspective view of a distal end of another embodiment of a cutting cannula 1524 compatible with certain embodiments of bone biopsy systems disclosed herein. The cutting cannula 1524 is narrower at the distal end than it is in more proximal regions. Stated otherwise, there is an angled step 1601 at the distal end at which the outer diameter decreases in the distal direction. To assist in cutting with such an arrangement, serrations or cutting flutes 1603 are positioned about the cutting cannula 1603.

Figure 41B:
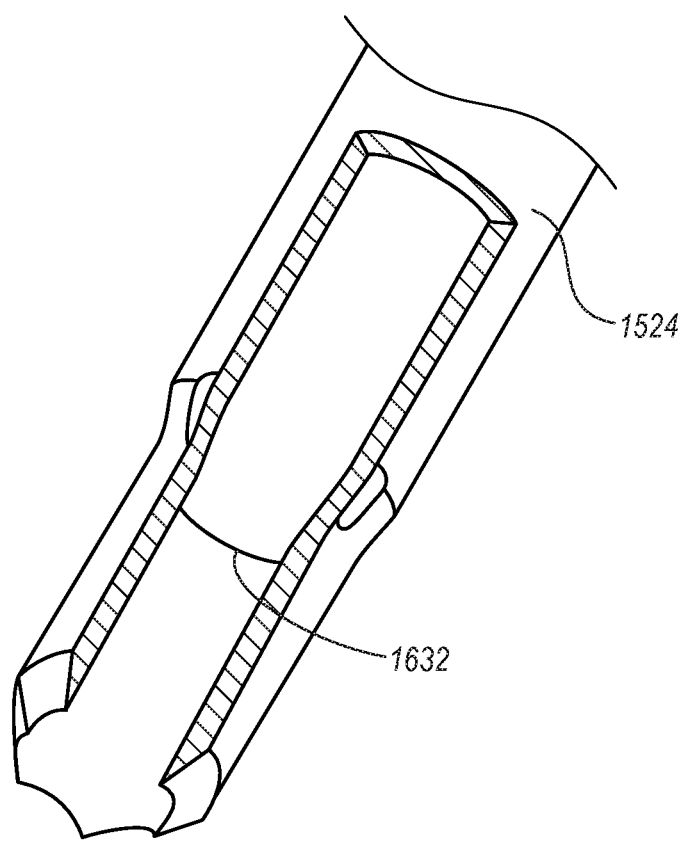
FIG. 41B is a partial cutaway view of the distal end of the cutting cannula of FIG. 41A depicting an interior of the cutting cannula.

With reference to FIG. 41B, the interior of the cutting cannula 1524 resembles the interior of the cutting cannula 1324 and includes an inner step or ridge 1632 at which the inner diameter expands in the proximal direction. The cutting cannula 1524 can function much the same as the cutting cannula 1324. Cored samples can expand with the cutting cannula 1524 and remain therein until pushed out in a proximal direction, e.g., via a pushing rod.

Figure 42:
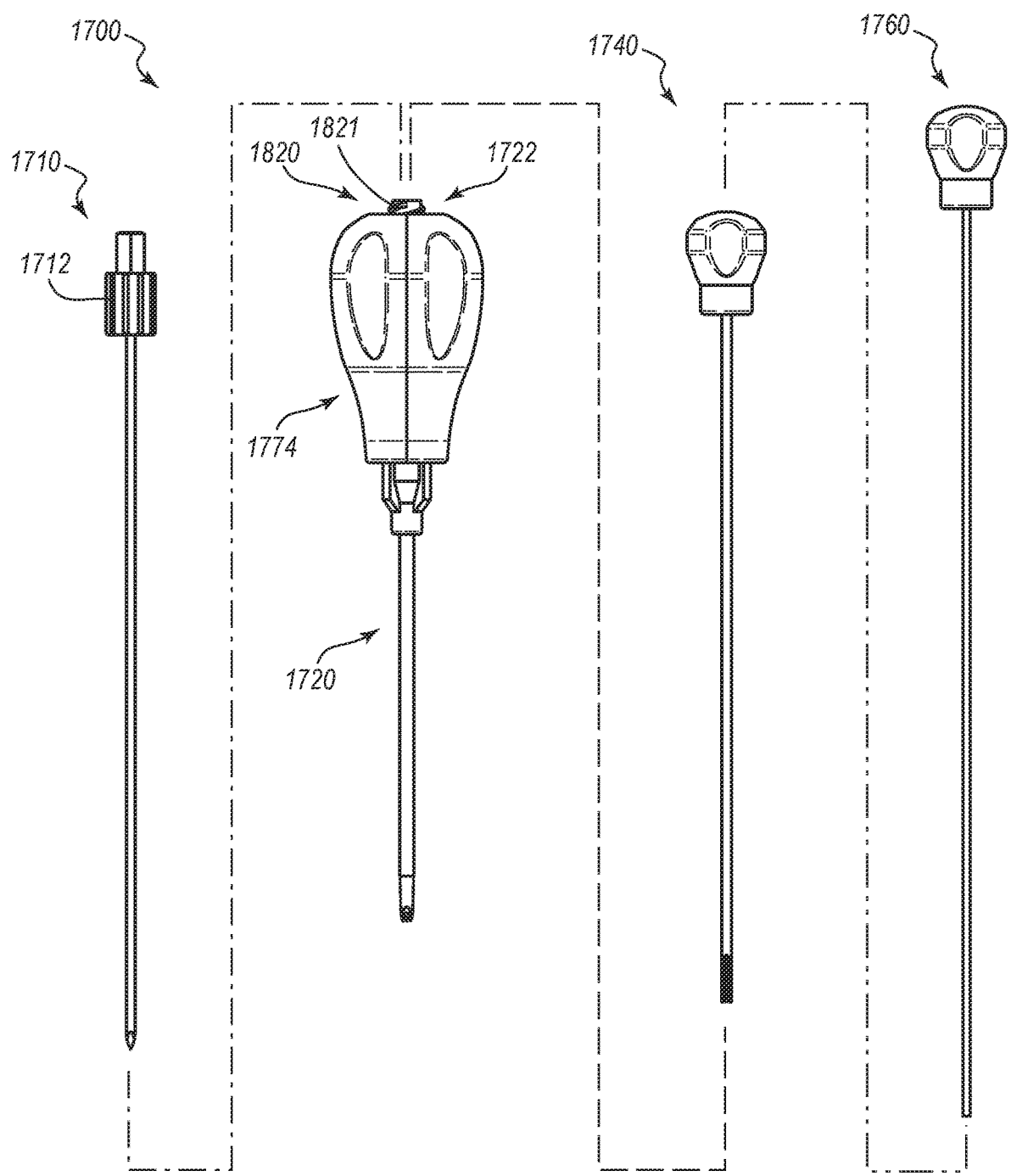
FIG. 42 is an elevation view of another embodiment of a bone biopsy system.

FIG. 42 is an elevation view of an embodiment of a bone biopsy system 1700 that resembles other bone biopsy systems disclosed herein in many respects. For example, the bone biopsy system 1700 is similar to the system 1000. Like the system 1000, the system 1700 includes a trocar assembly 1710, a cutting assembly 1720, a handle 1774, an extraction assembly 1740, and a pushing rod 1760. These various components can interact with each other and be used in methods or processes substantially such as those previously described.

Unlike the trocar assembly 1010, however, the trocar assembly 1710 includes a trocar hub 1712 that attaches directly to a medical connector 1820 portion (FIG. 44C) of a cutting cannula hub 1722, rather than to a collar or other separate feature of the cannula hub 1722. Further, unlike the removable handle 1074 of the system 1000, the illustrated handle 1774 is fixedly secured to the cutting cannula hub 1722. Other differences will also be apparent from the discussion that follows. As previously noted, however, any suitable feature of the present embodiment that differs from those of other systems can be incorporated into those other systems, and vice versa.

Figure 43A:
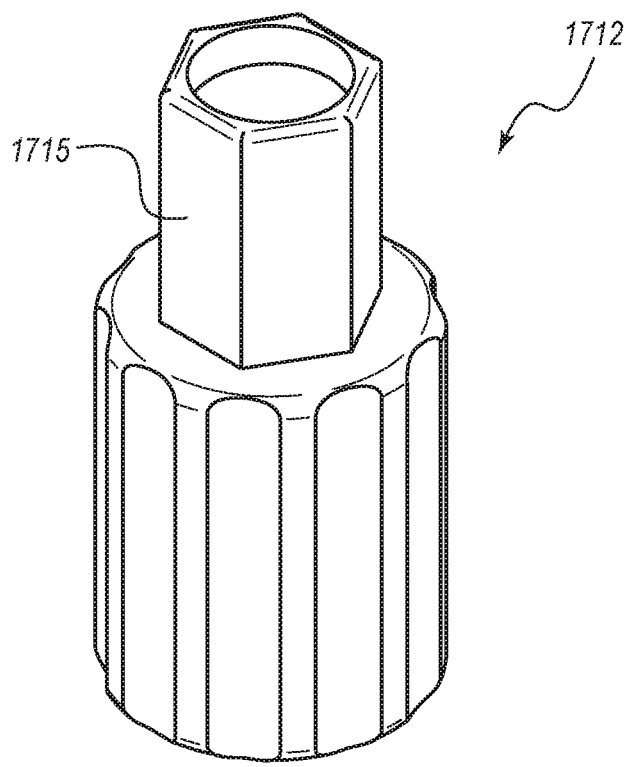
FIG. 43A is an upper perspective view of an embodiment of a trocar hub compatible with an embodiment of a trocar assembly of the bone biopsy system of FIG. 42.
Figure 43B:
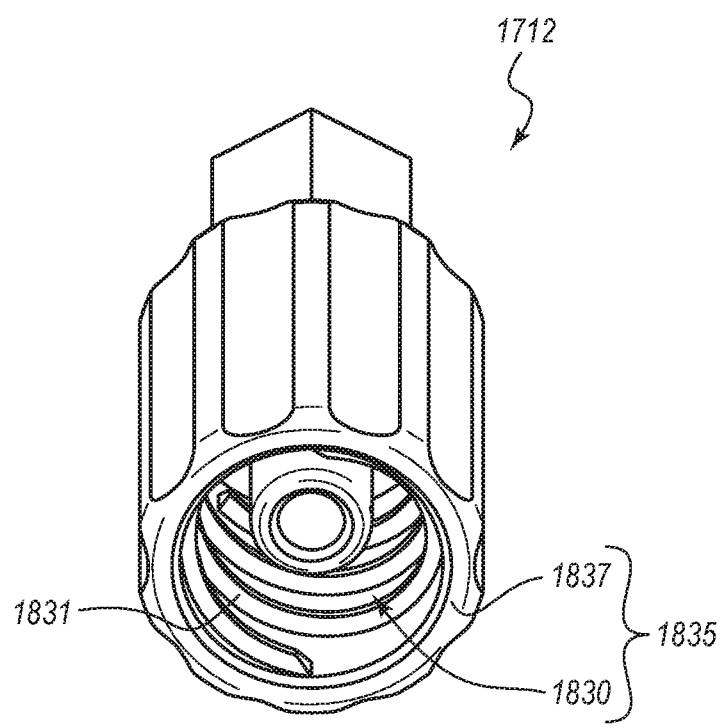
FIG. 43B is a lower perspective view of the trocar hub of FIG. 43A.

With reference to FIGS. 43A and 43B, the trocar hub 1712 includes a connection interface 1715, or driver connector, for coupling with a powered driver (and/or for separately coupling with a manual driver, in some instances, as further discussed with respect to other embodiments below). The connection interface 1715 is at an upper or proximal end of the trocar hub 1712. Again, as with other embodiments, the term "trocar" is used for convenience consistent with the illustrated embodiment, but the more general terms such as elongated insert may be used.

The lower or distal end of the trocar hub 1712 includes a connection interface 1835 that is configured to longitudinally and rotationally lock to the cutting cannula hub 1722. The illustrated connection interface 1835 includes a connector 1830 configured to couple with the medical connector 1820 of the cutting assembly 1720, as further discussed below. Due to its complementarity to the medical connector 1820, the connector 1830 may also be referred to as a medical connector. The illustrated medical connectors 1830 comprises a Luer fitting 1831.

The connection interface 1835 can further include a distal face 1837 of the trocar hub 1712. As further discussed below, the distal face 1837 can be configured to abut against a surface of the cutting cannula hub 1722 to assist with rotational and translational locking of the hubs 1712, 1722.

Figures 44A, 44B:
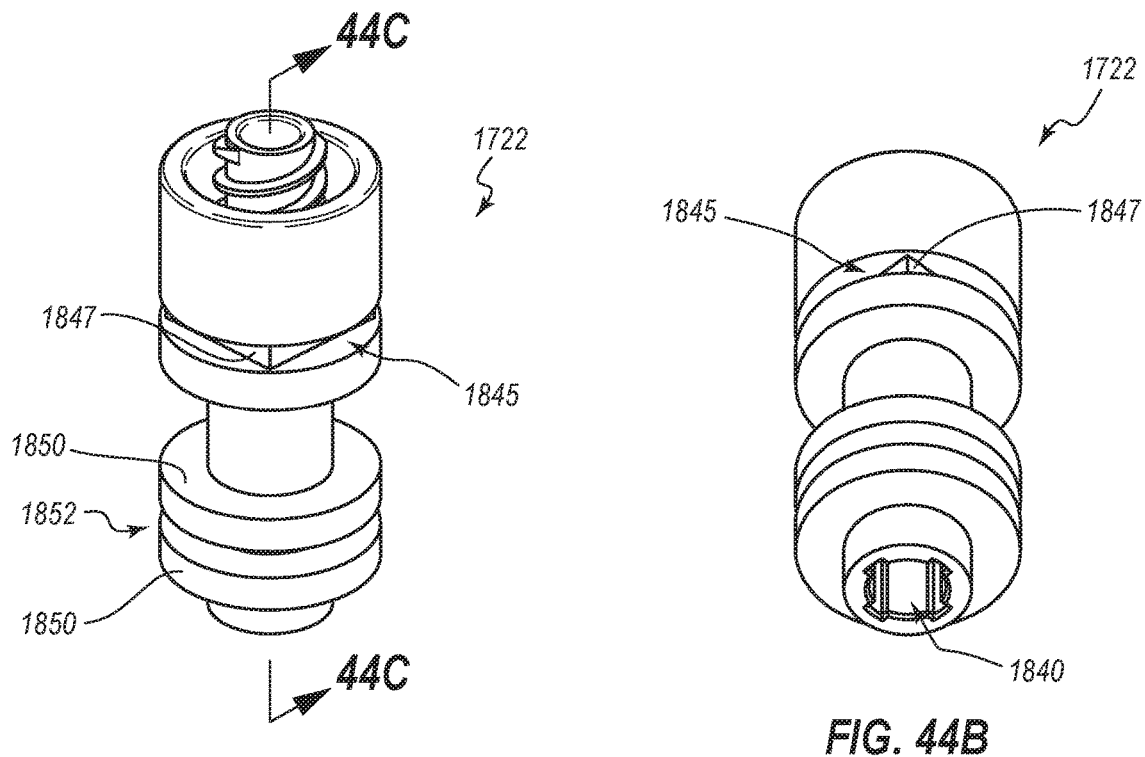
FIG. 44A is an upper perspective view of an embodiment of a hub compatible with an embodiment of a cutting assembly of the bone biopsy system of FIG. 42.
FIG. 44B is a lower perspective view of the hub of FIG. 44A.
Figures 44C, 45A, 45B:
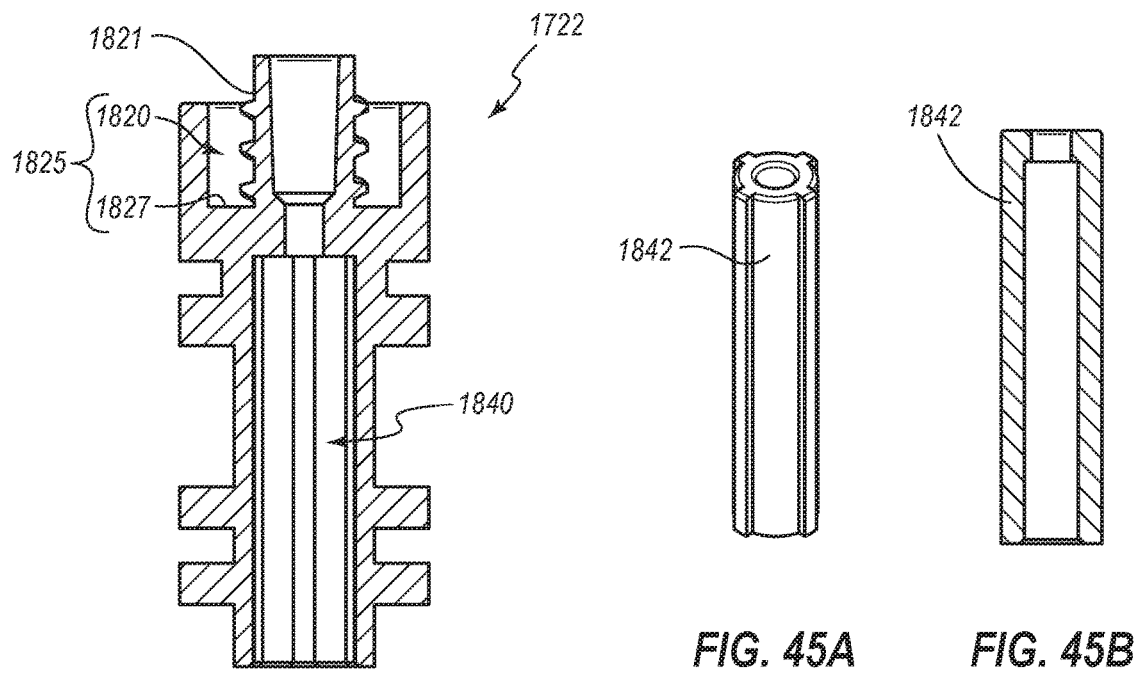
FIG. 44C is a cross-sectional view of the hub of FIG. 44A taken along the view line 44C-44C in FIG. 44A.
FIG. 45A is an upper perspective view of an embodiment of a spline element compatible with the hub of FIG. 44A.
FIG. 45B is a lower perspective view of the spline element.

With reference to FIGS. 44A-44C, the cutting cannula hub 1722 can include the medical connector 1820 previously mentioned, such as a Luer fitting 1821. The medical connector 1820 can be in fluid communication with a spline cavity 1840, which can receive the spline element 1842 depicted in FIGS. 45A and 45B. The spline element 1842 can define an opening at a proximal end thereof to establish fluid communication between the medical connector 1820 and the cutting cannula 1824, when the cutting cannula 1824 is received within and attached to the spline element 1842 (see FIG. 52B). With reference to FIG. 44C, a coupling interface 1825 can include the medical connector 1820, and can further include a proximally facing abutment surface 1827, as further discussed below.

With reference again to FIGS. 44A-44C, an external surface of the cutting cannula hub 1722 can include a rotational locking feature 1845, which can interact with the handle 1774 to maintain a fixed angular relationship between the cutting cannula hub 1722 and the handle 1774. In the illustrated embodiment, the rotational locking feature 1845 comprises a recess 1847 positioned between two substantially parallel disk-shaped lateral protrusions. The recess 1847 includes a base surface that is substantially square-shaped in cross section. Any other suitable rotational locking feature is contemplated.

The cutting cannula hub 1722 can include any other suitable features—e.g., surface features—for coupling with the handle 1774. For example, in the illustrated embodiment, the cutting cannula hub 1722 includes a distal pair of parallel disks 1850 that define another recess 1852 into which one or more extensions of the handle 1774 may protrude.

With reference again to FIG. 42, in the illustrated embodiment, the handle 1774 is formed of a plurality of parts. In particular, the handle 1774 includes two identical halves which are joined at the vertical seam depicted in FIG. 42. The assembled handle 1774 is substantially bulbous and readily grippable, graspable, and/or manipulable by a hand of a user, or stated otherwise, is ergonomically shaped for ready manipulation for manual drilling or coring. Other configurations are contemplated. For example, in some embodiments, the handle 1774 may be substantially T-shaped, or can include a plurality of grips that extend laterally from a longitudinal axis of the handle 1774. In some instances, a substantially bulbous handle 1774 may be well suited for relatively high rotational speeds, such as when the cutting assembly is 1720 is coupled to a powered driver for drilling.

Figure 46A:
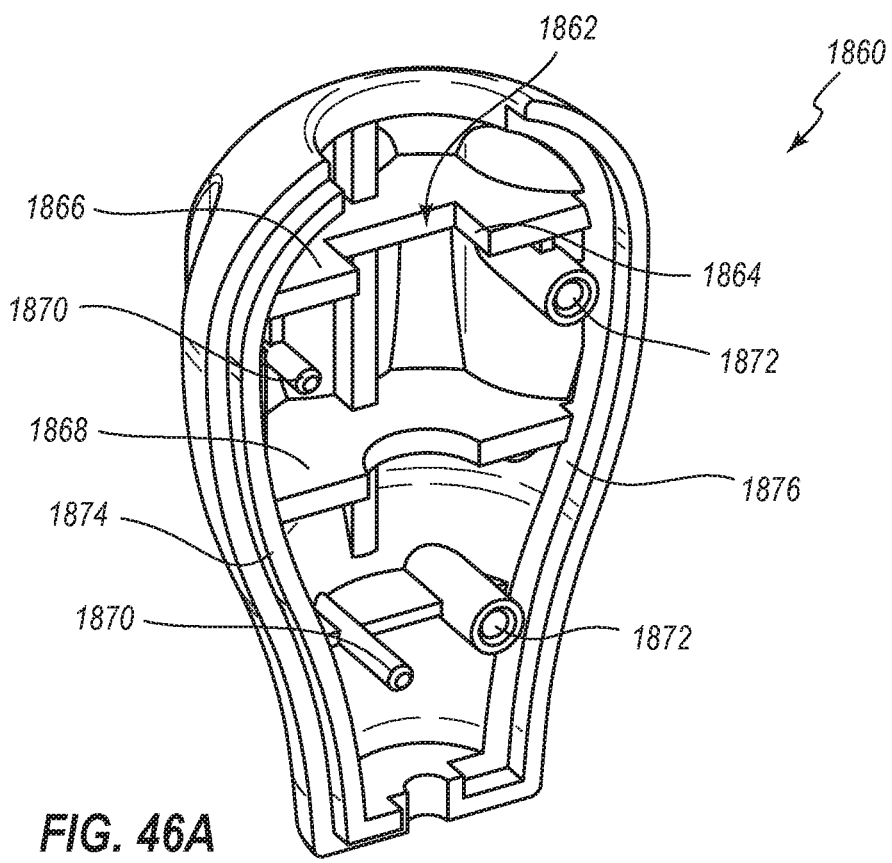
FIG. 46A is a perspective view of an embodiment of a handle element configured for coupling with the hub of FIG. 44A.
Figure 46B:
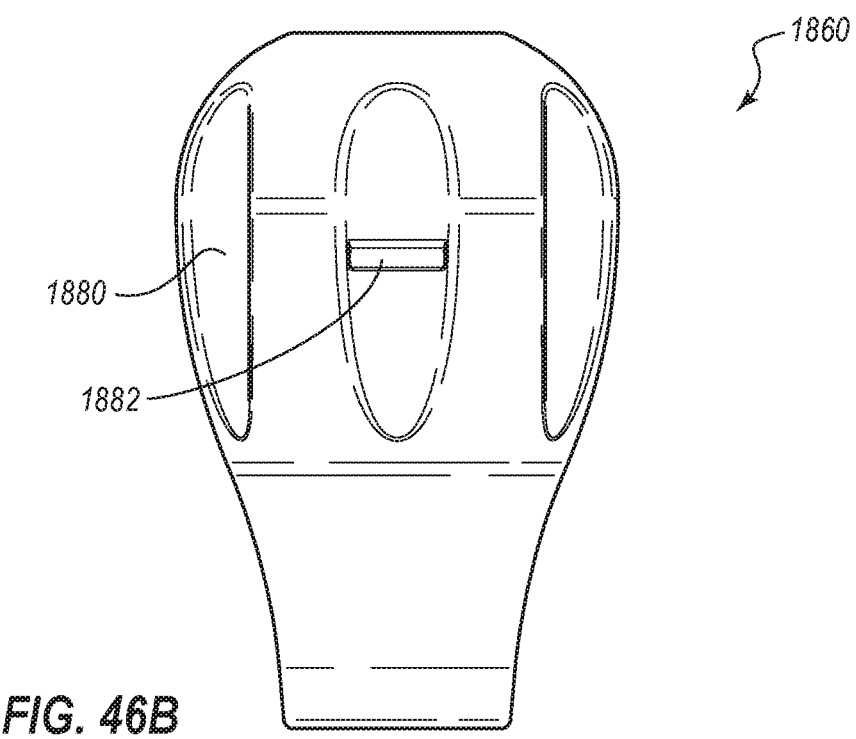
FIG. 46B is an elevation view of the handle element of FIG. 46A.

FIGS. 46A and 46B illustrate one embodiment of a handle element 1860. Again, in the illustrated embodiment, two such handle elements 1860 may be joined together to form the handle 1774. The joined handle elements 1860 may house or encompass the cutting cannula hub 1722. The handle elements 1860 may be permanently joined to each other (e.g., adhered, bonded, welded). Any other suitable arrangement is contemplated. For example, in other embodiments, the handle 1774 may be integrally formed with the cutting cannula hub as a monolithic unitary component.

With reference to FIG. 46A, the handle element 1860 can include a rotational locking feature 1862 configured to interact with the rotational locking feature 1845 of the cutting cannula hub 1722. In the illustrative embodiment, the rotational locking feature 1862 comprises a rectangular recess 1864 that is complementary to one half of the square-shaped recess 1847 of the cutting cannula hub 1722. When two handle elements 1860 are joined together, the surfaces that define the rectangular recesses 1864 abut the square-shaped base of the square-shaped recess 1845 to lock the handle 1774 in a fixed angular orientation relative to the cutting cannula hub 1722.

The handle element 1860 can include further features to achieve alignment and/or translational force transfer between the hub 1722 and the handle 1774. For example, the handle element 1860 includes a proximal platform 1866 and a distal platform 1868 that fit between the proximal and distal pairs of parallel disks defined by the hub 1722.

In the illustrated embodiment, each handle element 1860 includes a pair of posts 1870 and a pair of sockets 1872 that are configured to couple with the sockets 1872 and the posts 1870, respectively, of the other handle element 1860. Similarly, each handle element 1860 includes a peripheral protrusion 1874 along one edge and a peripheral recess 1876 along an opposite edge that are configured to mate with the peripheral recess 1876 and the peripheral protrusion, respectively, of the other handle element 1860.

With reference to FIG. 46B, in some embodiments, an external surface of each handle element 1860 can include a plurality of longitudinally extending flutes or recesses 1880. The recesses 1880 may be concavely rounded. In the illustrated embodiment, the recesses 1880 can facilitate gripping of the handle 1774.

As discussed further below with respect to another embodiment, the recesses 1880 may further be used to couple with a handle extension, handle cover, or manual driver to optionally use the system in a fully manual mode. For example, the recesses 1880 can assist in rotationally locking a manual driver to the handle 1774. In some embodiments, the handle element 1860 may include one or more securement notches 1882 for coupling with the manual driver. In other embodiments, the securement notches 1882 may be omitted.

Figure 47A:
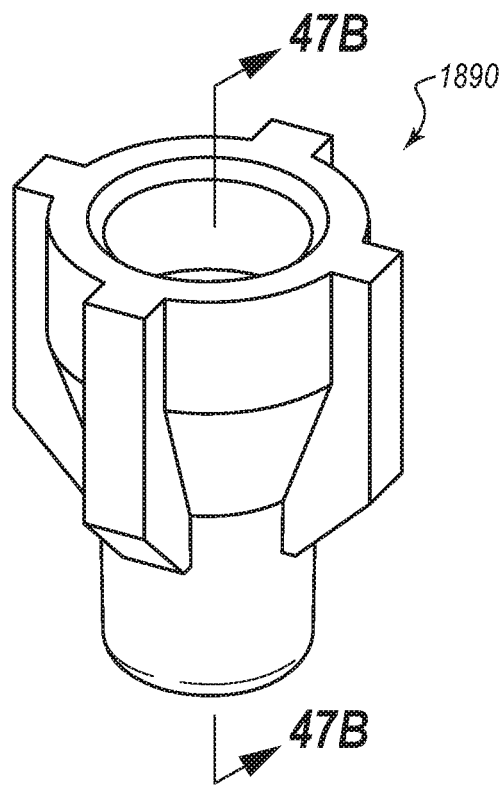
FIG. 47A is a perspective view of an embodiment of a depth gauge that is compatible with a cutting cannula of the system of FIG. 42.
Figure 47B:
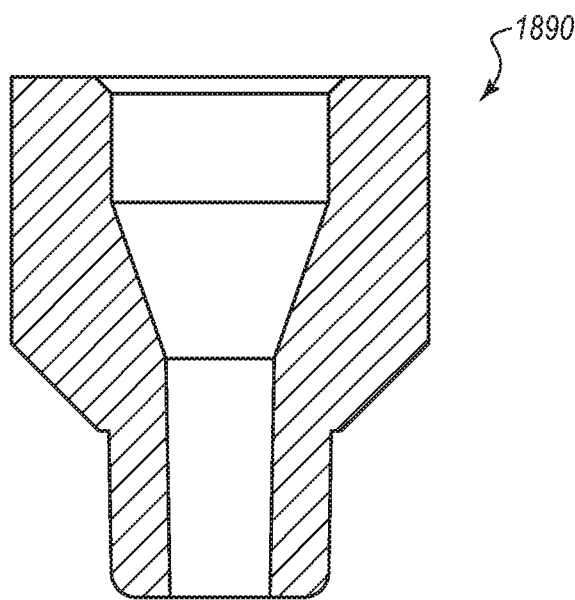
FIG. 47B is a cross-sectional view of the depth gauge of FIG. 47A taken along the view line 47B-47B in FIG. 47A.

FIGS. 47A and 47B depict an embodiment of a depth gauge 1890 that may be used with various systems disclosed herein. In some embodiments, a cutting cannula includes depth markers of any suitable variety at an exterior surface thereof. The depth gauge 1890 and/or depth markers may be used in any suitable manner, including those known in the art.

Figure 48A:
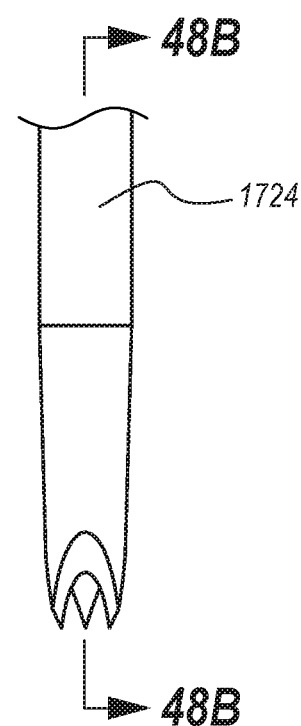
FIG. 48A is an elevation view of the cutting cannula of the system of FIG. 42.
Figure 48B:
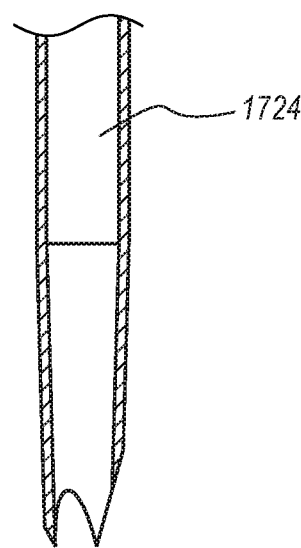
FIG. 48B is a cross-sectional view of the cutting cannula taken along the view line 48B-48B in FIG. 48A.

With reference to FIGS. 48A and 48B, the illustrated embodiment includes a cutting cannula 1724 having a tapered distal end, which may also be referred to as a restriction, constriction, deflection region, etc., consistent with similar features disclosed above. A sidewall of the cutting cannula 1724 has a substantially uniform thickness along a full length thereof. Accordingly, both the exterior and interior surfaces taper at substantially the same position and by substantially the same amount. The tapered inner surface can be configured to interact with resilient capturing arms of the extraction assembly 1740 in manners such as previously discussed with respect to other embodiments. In particular, the tapered inner surface can act as a deflection surface or constriction that deflects the gripping arms inward as an extraction cannula is advanced distally within the cutting cannula 1724. For example, compare FIG. 54C with FIG. 5E and FIG. 34D. In the illustrated embodiment, a distal tip of the cannula 1724 includes three facets, yielding a three-pointed tip. Other arrangements are also contemplated (see, e.g., FIG. 58).

Figure 49A:
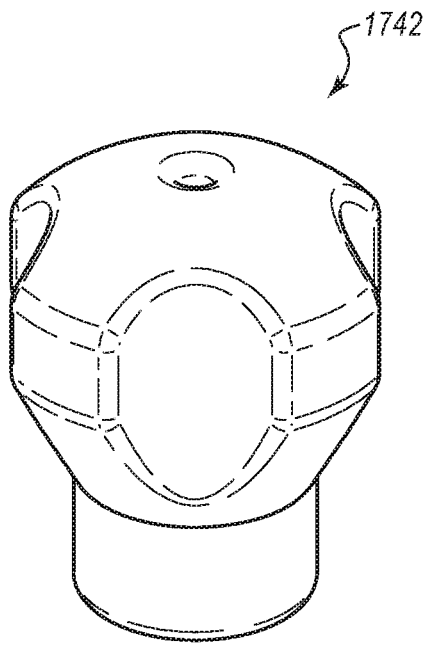
FIG. 49A is an upper perspective view of an embodiment of an extraction hub compatible with an extraction assembly of the system of FIG. 42.
Figure 49B:
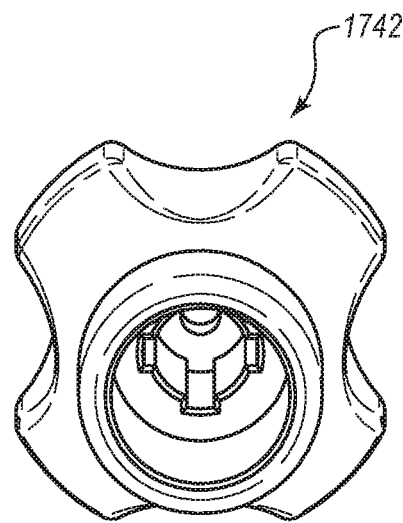
FIG. 49B is a lower perspective view of the extraction hub of FIG. 49A.
Figure 50:
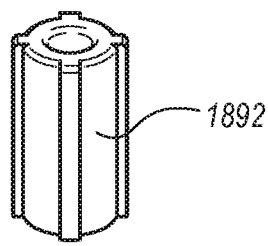
FIG. 50 is a perspective view of an embodiment of a spline element compatible with the extraction assembly.
Figure 51:
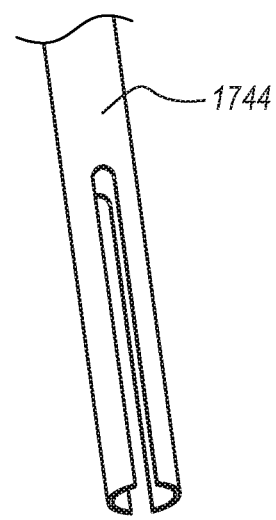
FIG. 51 is a perspective view of a distal end of an extraction cannula of the extraction assembly.

FIGS. 49A and 49B are perspective views of an embodiment of an extraction hub 1742, which can receive the spline element 1892 depicted in FIG. 50. FIG. 51 is a perspective view of a distal end of an extraction cannula 1744, which can be substantially identical to the extraction cannula 1044 discussed previously.

FIGS. 52A-54C depict various operational configurations of various components of the system 1700. In certain embodiments, these operational configurations, and methods associated with their use, can closely track the operational configurations and methods discussed above with respect to FIGS. 31A-35. In some instances, a primary difference between these two sets of operational configurations and associated method stages or steps results from the handle 1774 being fixedly secured to the cutting cannula hub 1722. As a result, some methods omit the step of coupling the handle to the cutting cannula hub 1722, as these components are provided pre-assembled, in fixed or permanent attachment, and/or integrally formed with each other. Likewise, some methods omit a step of decoupling the handle 1774 from the cutting cannula hub 1722.

Moreover, the handle 1774 is present on the cutting cannula hub 1722 during initial drilling of the cortical bone. That is, with reference to FIGS. 52A and 52B, the trocar assembly 1710 and the cutting assembly 1720 can either come preassembled or can be placed in a coupled configuration. As with other embodiments, such a configuration may be referred to as a power drilling configuration. In some instances, in this coupled state, the trocar assembly 1710 and the cutting assembly 1720 can be coupled with a driver, such as a powered driver. The coupled components can be drilled through the cortex of a bone, as previously discussed. The handle 1774 thus can be present during powered drilling. In some embodiments, the substantially rotationally symmetrical configuration, about a rotational axis, of the handle 1774 can be particularly suitable for such powered drilling, which can occur at relatively high speeds. Other features, such as a relatively low profile, can also be advantageous for this purpose, in some instances.

In some embodiments, the handle 1774 can extend laterally outward from a central longitudinal axis of the cutting assembly 1720 by a significant amount. A relatively large outer diameter of the handle 1774, as compared with a relatively small outer diameter of the cutting cannula 1724, can, in some instances, be advantageous for imparting torque to the cutting cannula 1724 via the handle 1774 and/or for gripping by a user. In various embodiments, the handle 1774 can define an outermost diameter (e.g., along a plane transverse to a rotational axis of the handle 1774) that is no less than 8, 9, 10, 11, or 12 times as large as an outer diameter of the cutting cannula 1724.

Figures 52A, 52B:
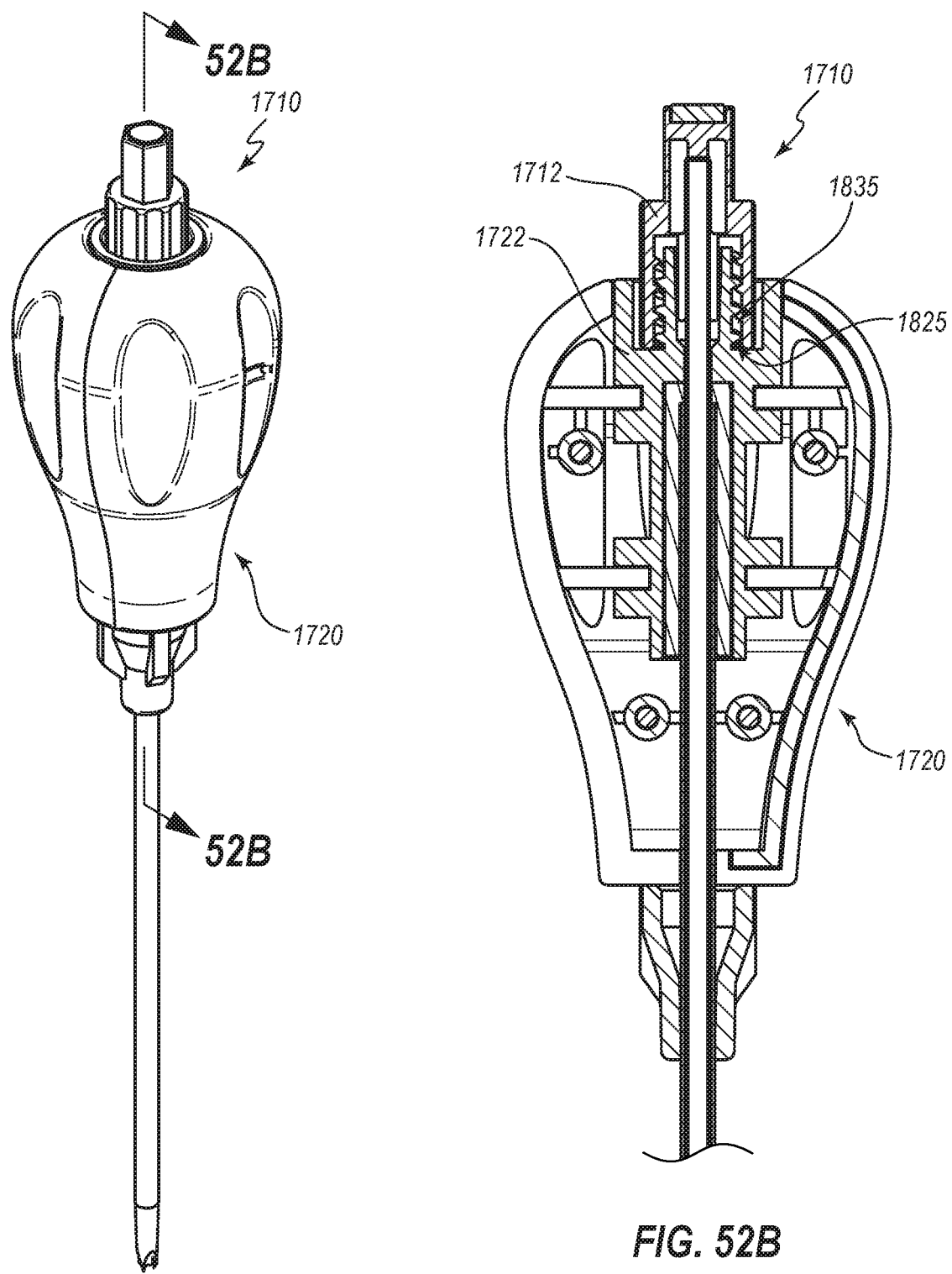
FIG. 52A is a perspective view of the trocar assembly and the cutting assembly of the system of FIG. 42 in a coupled configuration, such as may be used to drill through cortical bone.
FIG. 52B is a cross-sectional view of the trocar assembly coupled with the cutting assembly taken along the view line 52B-52B in FIG. 52A.

With reference to FIG. 52B, the trocar hub 1712 can be coupled to the cutting cannula hub 1722 by engaging the coupling interfaces 1825, 1835. In particular, with simultaneous reference to FIGS. 52B, 43B, and 44C, the complementary threads of the two Luer fittings 1821, 1831 can be engaged and rotated against one another to advance the distal face 1837 of the trocar hub 1712 into abutment with the proximally facing abutment surface 1827 of the cutting cannula hub 1722. Interference of these opposing abutment surfaces 1827, 1837 helps to ensure transfer of rotational motion to the cutting cannula hub 1722 from the trocar hub 1712. Moreover, coupling of the Luer fittings 1821, 1831 and engagement of the abutment surfaces 1827, 1837 can inhibit relative longitudinal movement between the trocar hub 1712 and the cutting cannula hub 1722.

In some instances, the fixed angular relationship and fixed longitudinal relationship between the hubs 1712, 1722 is achievable in only a single rotational direction (e.g., clockwise, as viewed from above) when rotation of the cutting cannula hub 1722 is opposed. For example, bone material provides reactive forces in resistance to being cut, which can tend to slow or stop rotation of the hub 1712 as the trocar hub 1712 spins. Thus, it can be desirable to rotate the system in a direction that tightens the threaded grip and increases the abutment force of the abutment surfaces 1827, 1837 to ensure that the hubs 1712, 1722 remain rotationally and longitudinally fixed relative to each other during drilling.

Figure 53:
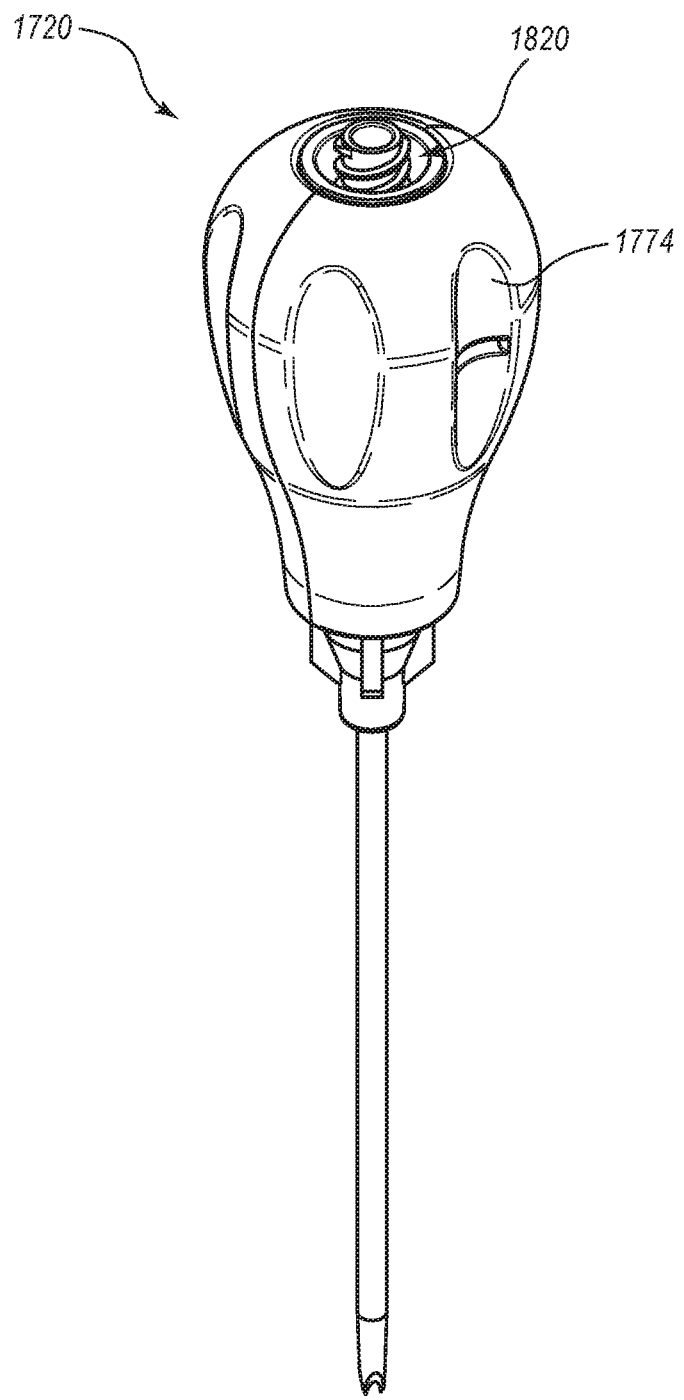
FIG. 53 is a perspective view of the cutting assembly after the trocar assembly has been removed therefrom.

Once drilling through the cortex is complete, the cutting assembly 1720 can remain in the bone, as previously described, and the trocar assembly 1710 can be removed, e.g., by rotating the trocar assembly 1710 in the opposite direction while maintaining the cutting assembly 1720 in a fixed rotational relationship relative to the bone. FIG. 53 is a perspective view of the cutting assembly 1720 after the trocar assembly 1710 has been removed therefrom. Aspiration is possible at this stage, as previously discussed. Indeed, in the illustrated embodiment, the medical connector 1820, which is in fluid communication with a lumen of the cutting cannula, is exposed an capable of being connected to any suitable medical device.

The configuration shown in FIG. 53 may be referred to as a manual coring configuration. In this configuration, the handle 1774 can be manually manipulated, e.g., rotated and advanced distally, to core out a sample of marrow. In some instances, the cutting assembly 1720 and handle 1774 are advanced so as to core out the sample prior to coupling the extraction assembly 1740 to the cutting assembly 1720. In other instances, the extraction assembly 1740 may be coupled with the cutting assembly 1720 (e.g., loosely, such that the deflection arms of the extraction cannula are not deflected inward by the constriction of the cutting cannula) prior to the manual coring event.

FIGS. 54A-54C are various views of a stage subsequent to that depicted in FIG. 53, in certain illustrative methods, in which the extraction assembly 1740 is coupled with the cutting assembly 1720. As shown in FIG. 54C, distal advancement of the extraction cannula 1744 can cause gripping arms 1747, 1748 thereof to compress inward under the influence of a construction 1727 (e.g., the distal taper) of the cutting cannula 1724. This can assist in removal of the cored sample in manners such as previously discussed. Further in the illustrated embodiment, after the extraction assembly 1740 has been removed from the cutting assembly 1720, the sample can be urged from the extraction cannula 1744 by advancing the push rod 1760 distally through the extraction cannula 1744.

Figure 55:
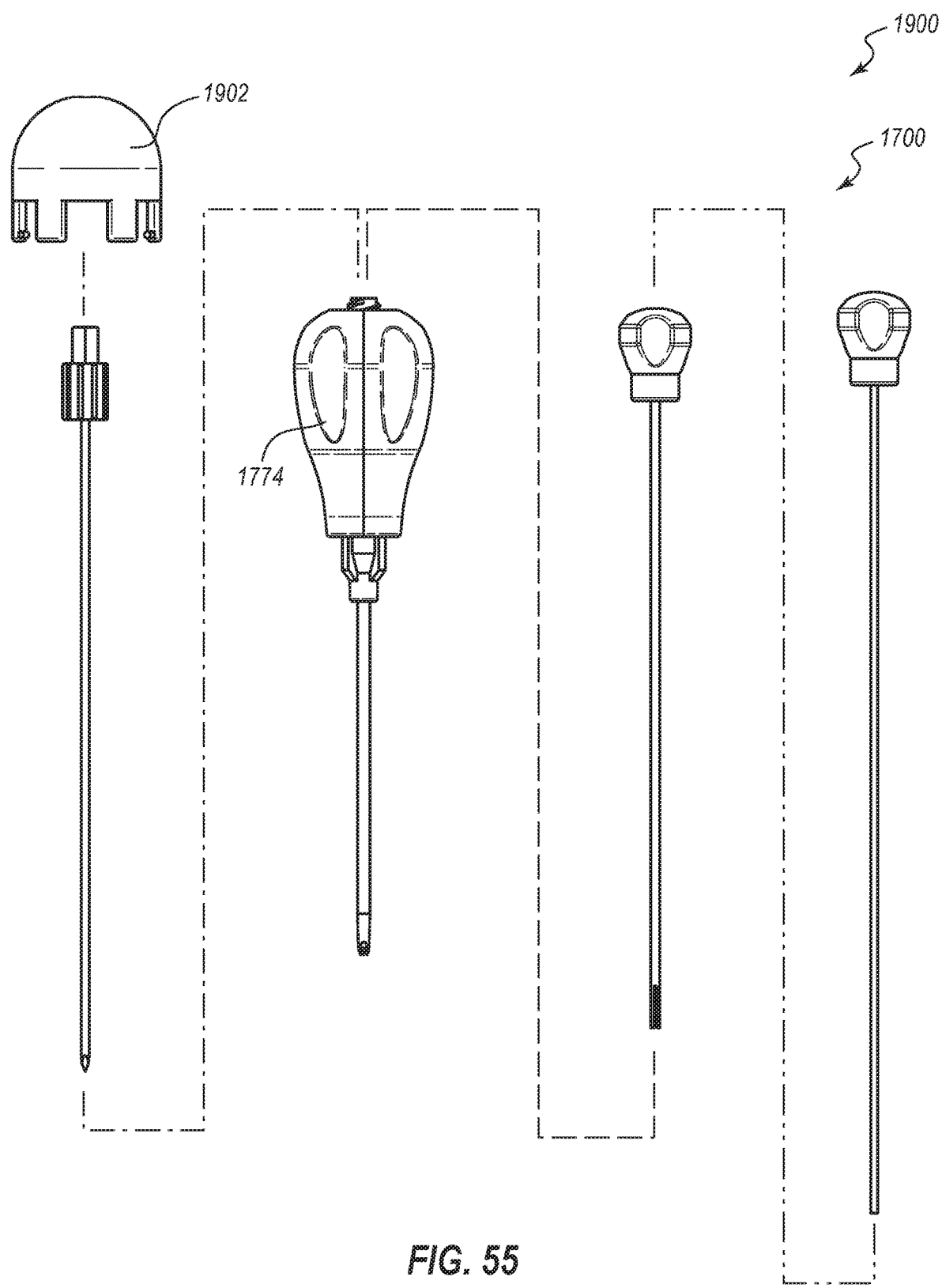
FIG. 55 is an elevation view of another embodiment of a bone biopsy system that substantially resembles the bone biopsy system of FIG. 42, but further includes an embodiment of a handle cover configured to permit the system to be selectively used in either a fully manual or a semi-manual operational mode.

FIG. 55 is an elevation view of an embodiment of a bone biopsy system 1900 that includes the bone biopsy system 1700, as previously described, but further includes a handle cover 1902 configured to permit the system 1900 to be selectively used in either a fully manual or a semi-manual (e.g., partially automated or powered/partially manual) operational mode. The handle cover 1902 may also or alternatively be referred to as a handle extension, an extender, a handle attachment, a handle component, etc. Further, the handle cover 1902 may more generally be referred to as a handle or as a driver (e.g., a manual driver). Hereafter, the term manual driver 1902 will be used.

Figure 56A:
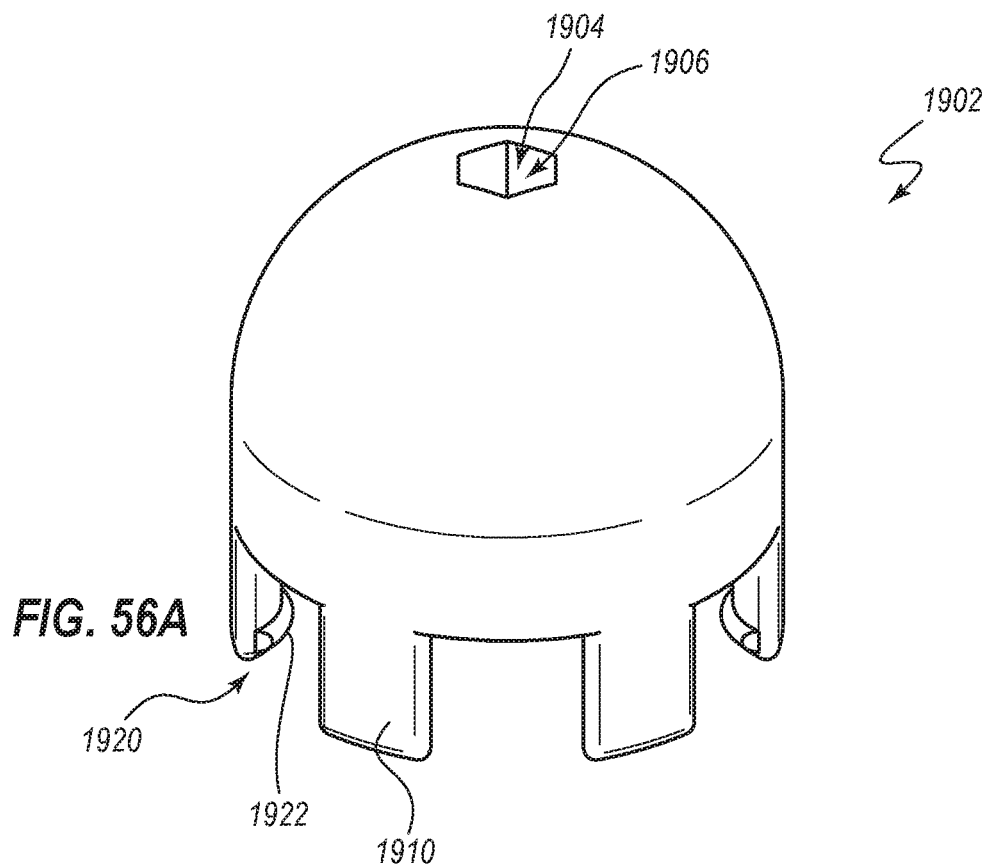
FIG. 56A is an upper perspective view of the handle cover of FIG. 55.
Figure 56B:
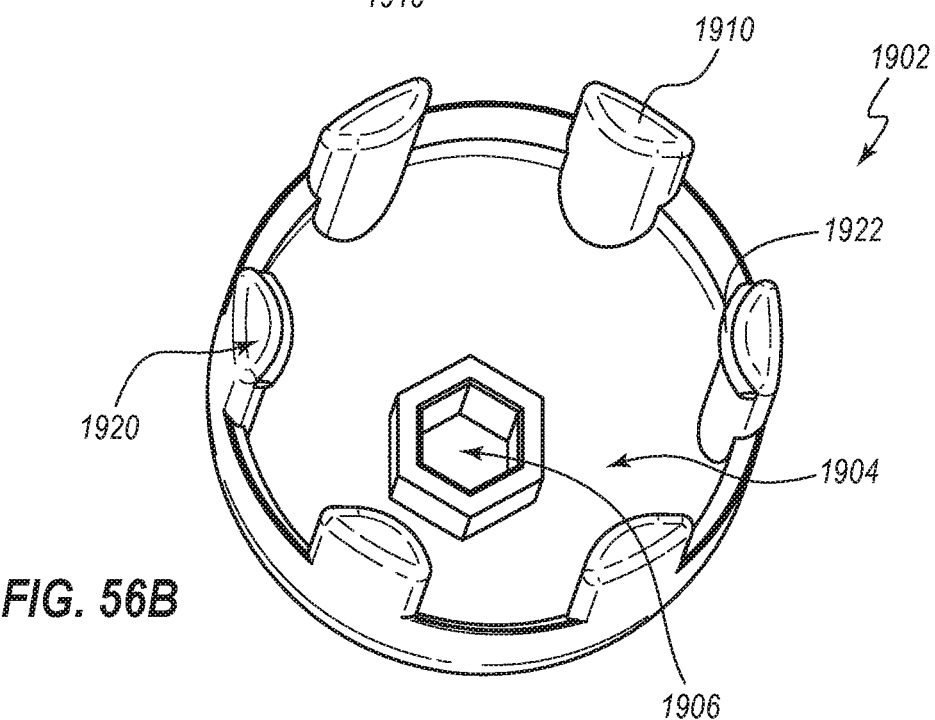
FIG. 56B is a lower perspective view of the handle cover.

With reference to FIGS. 56A and 56B, the manual driver 1902 includes a coupling feature or connection interface 1904 for imparting at least rotational movement to the trocar assembly 1710. The illustrated coupling feature 1904 includes a socket 1906 that is complementary to the coupling post (e.g., driver connector) of the trocar assembly 1710, and thus is configured to rotationally lock the manual driver 1902 and the trocar assembly 1710. As shown in FIG. 56B and FIG. 57B, the socket 1906 can extend distally by a sufficient amount to also contact a proximal surface (e.g., a proximal shoulder) of the trocar hub 1712, such that the manual driver 1902 may further directly impart translational (e.g., distal) motion to the trocar assembly 1710.

Figure 57A:
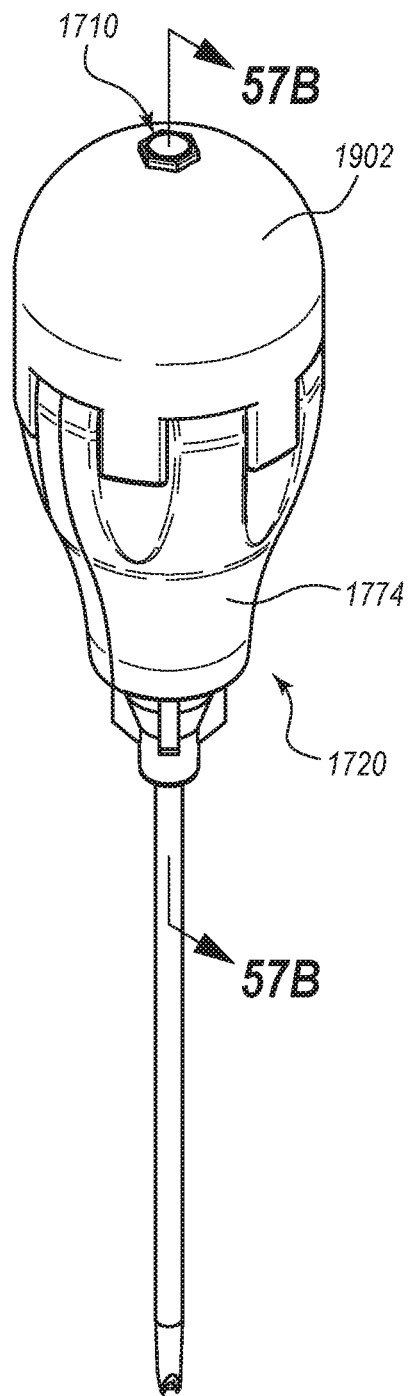
FIG. 57A is a perspective view of the handle cover coupled with a trocar assembly and with a cutting assembly.
Figure 57B:
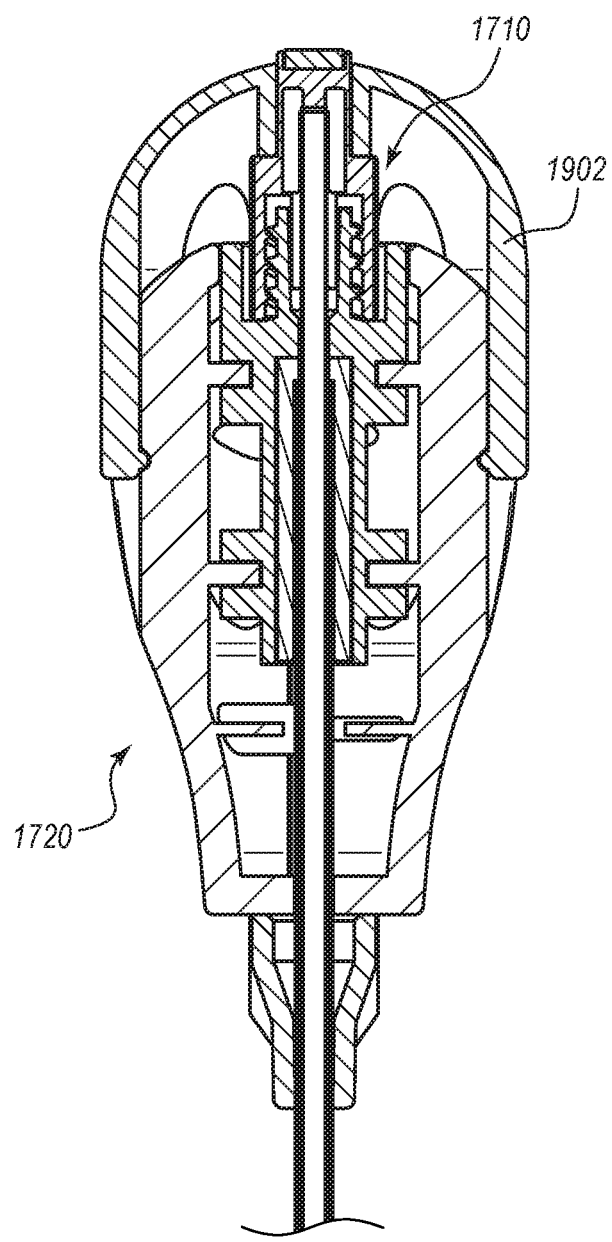
FIG. 57B is a cross-sectional view of the cover coupled with the trocar assembly and the cutting assembly taken along the view line 57B-57B in FIG. 57A.

With continued reference to FIGS. 56A and 56B, the manual driver 1902 can further include a plurality of longitudinally extending arms or fingers 1910 that can be convexly rounded at an inner surface thereof to seat within the longitudinal flutes 1880 of the handle 1774 (see FIGS. 46B, 57A, 57B). The fingers 1910 may also be referred to as inward projections 1910. Such an arrangement can rotationally lock the manual driver 1702 to the handle 1774.

In some embodiments, the manual driver 1902 can include a connection interface 1920 for selectively securing the manual driver 1902 to the handle 1774, such as, for example, in a manner that can prevent inadvertent proximal removal of the manual driver 1902 from the handle 1774. The connection thus may selectively longitudinally fix the manual driver 1902 to the handle 1774. In some embodiments, this connection may rotationally fix the manual driver 1902 to the handle 1774.

In the illustrated embodiment, the connection interface 1920 comprises two, diametrically opposed, inwardly projecting catches 1922 that seat within the securement notches 1882 of the handle 1774 (see FIG. 57B). The manual driver 1902 can be said to selectively clip onto the handle 1774. Any other suitable connection system (e.g., selectively attachable and detachable system) is contemplated.

FIGS. 57A and 57B depict the manual driver 1902 coupled with the trocar assembly 1710 and with the cutting assembly 1720 in manners previously disclosed. As previously discussed, when the trocar assembly 1710 and the cutting assembly 1720 are coupled in this manner, they may be referred to as being in a powered drilling configuration. However, due to the presence of the manual driver 1902, the system may instead be used for fully manual drilling. The configuration depicted in FIGS. 57A and 57B may be referred to as a manual drilling configuration.

In some instances, the system 1900 may be provided with the components coupled as shown in FIGS. 57A and 57B. To the extent powered drilling is desired to for passing through the cortex, the manual driver 1902 can first be removed, thereby exposing the coupling post of the trocar hub for coupling with the powered driver (e.g., power drill).

As previously mentioned, any of the systems may be included in a kit, similar to what was described above with respect to, e.g., the kit 1200 (FIG. 36). For example, in some embodiments, the system 1700 or the system 1900 is included in a kit that includes instructions for use, such as previously described. For example, the instructions for use can provide directions to carry out any of the method steps applicable to the respective system 1700, 1900. In some embodiments, the kit can include a powered driver. In other embodiments, the kit does not include a powered driver.

Figure 58A:
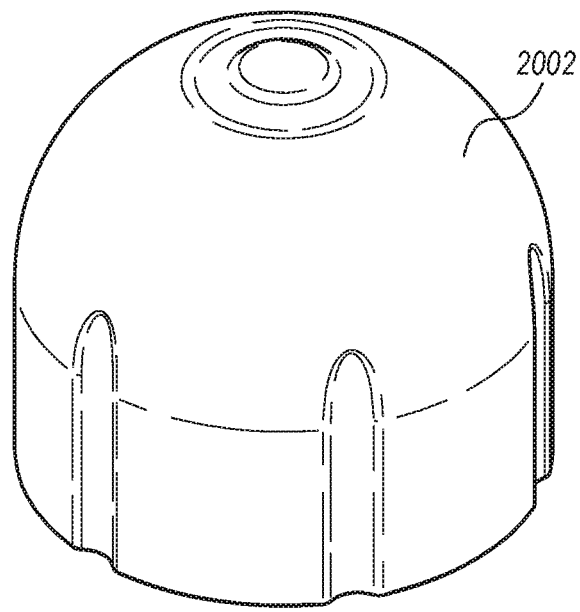
FIG. 58A is a top perspective view of another embodiment of a handle cover compatible with certain embodiments of bone biopsy systems, such as the bone biopsy system of FIG. 55.
Figure 58B:
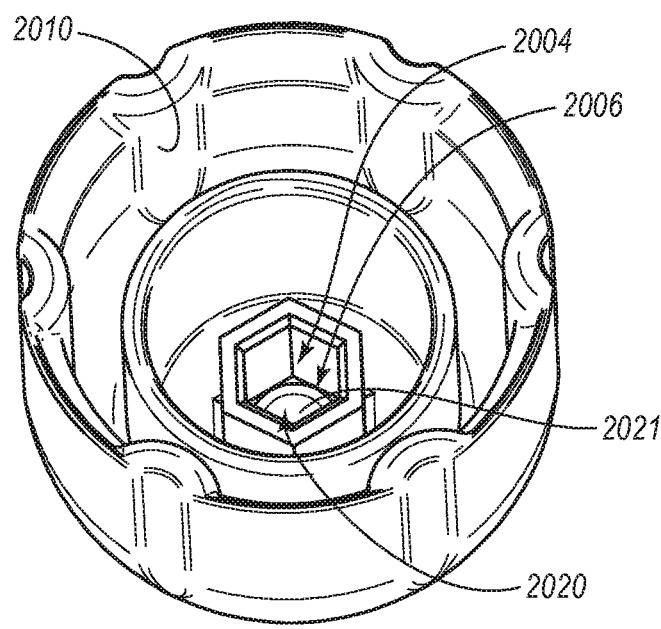
FIG. 58B is a bottom perspective view thereof.

FIGS. 58A and 58B depict another embodiment of a manual driver 2002 compatible with various embodiments of bone biopsy systems described herein, such as the bone biopsy system 1700. The manual driver 2002 includes a coupling interface 2004, such as a socket 2006. In the illustrated embodiment, the socket 2006 includes a different connection interface 2020 configured to assist in maintaining a fixed angular and/or longitudinal relationship between the manual driver 2002 and the trocar assembly 1710. In particular, in the illustrate embodiment, the connection interface 2020 includes a magnetic member 2021 that can function in manners such as previously described with respect to another magnetic member connected to the trocar hub 1722.

The manual driver 2002 can include a plurality of inward projections 2010, similar to the inward projections 1910 discussed previously. The manual driver 2002 can encompass a greater portion of the handle 1774.

Figure 59:
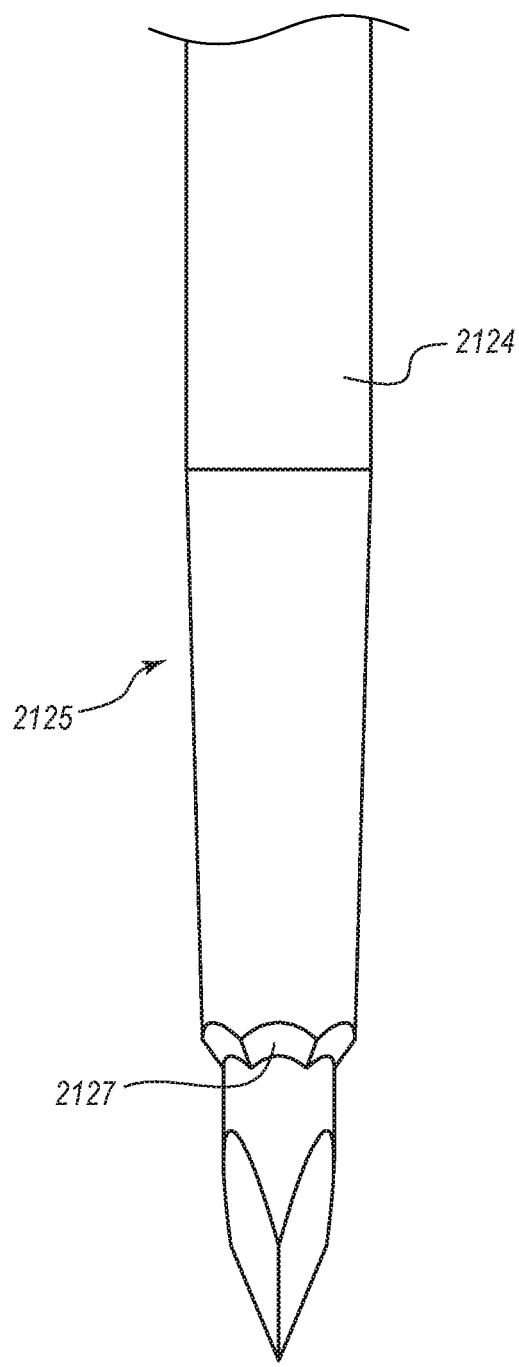
FIG. 59 is an elevation view of a distal end of a portion of another embodiment of a bone biopsy system.

FIG. 59 depicts a distal end of another embodiment of a trocar assembly coupled to a cutting assembly compatible with various embodiments disclosed herein, such as the system 1700. The illustrated cutting assembly includes a different configuration of a cutting cannula 2024. The cutting cannula 2024 includes a tapered region or constriction 2025, such as the like-numbered feature above. The distal tip, however, includes a plurality of shallow facets 2027. In the illustrated embodiment, there are six such facets. Other arrangements are contemplated.

As previously discussed, certain features may only be described with respect to one of the embodiments, herein, but it is understood that these features could be used with other embodiments. For example, the safety shield features disclosed with respect to FIGS. 9-12 can be incorporated into other embodiments described herein, including at least the systems 1000, 1300, 1700, and 1900.

Although the foregoing detailed description contains many specifics for the purpose of illustration, a person of ordinary skill in the art will appreciate that many variations and alterations to the following details can be made and are considered to be included herein. Accordingly, the foregoing embodiments are set forth without any loss of generality to, and without imposing limitations upon, any claims set forth. It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this disclosure belongs.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

As used in this specification and the appended claims, the singular forms "a," "an" and "the" include plural referents unless the context clearly dictates otherwise. Thus, for example, reference to "a layer" includes a plurality of such layers.

In this disclosure, "comprises," "comprising," "containing" and "having" and the like can have the meaning ascribed to them in U.S. patent law and can mean "includes," "including," and the like, and are generally interpreted to be open ended terms. The terms "consisting of" or "consists of" are closed terms, and include only the component structures, steps, or the like specifically listed in conjunction with such terms, as well as that which is in accordance with U.S. patent law. "Consisting essentially of" or "consists essentially of" have the meaning generally ascribed to them by U.S. patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term in the specification, like "comprising" or "including," it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein. The term "coupled," as used herein, is defined as directly or indirectly connected in any suitable manner. Objects described herein as being "adjacent to" each other may be in physical contact with each other, in close proximity to each other, or in the same general region or area as each other, as appropriate for the context in which the phrase is used. Occurrences of the phrase "in one embodiment," or "in one aspect," herein do not necessarily all refer to the same embodiment or aspect.

As used herein, the term "substantially" refers to the complete or nearly-complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Moreover, for references to approximations (which are made throughout this specification), such as by use of the terms "about" or "approximately," or other terms, it is to be understood that, in some embodiments, the value, feature, or characteristic may be specified without approximation. For example, where qualifiers such as "about," "substantially," and "generally" are used, these terms include within their scope the qualified words in the absence of their qualifiers. For example, where the term "substantially perpendicular" is recited with respect to a feature, it is understood that in further embodiments, the feature can have a precisely perpendicular orientation.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

References throughout this specification to "an example," if any, mean that a particular feature, structure, or characteristic described in connection with the example is included in at least one embodiment. Thus, appearances of the phrases "in an example" in various places throughout this specification are not necessarily all referring to the same embodiment.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the preceding claims up to and including claim [x]," where the bracketed term "[x]" is replaced with the number of the most recently recited independent claim. For example, for the first claim set that begins with independent claim 1, claim 3 can depend from either of claims 1 and 2, with these separate dependencies yielding two distinct embodiments; claim 4 can depend from any one of claim 1, 2, or 3, with these separate dependencies yielding three distinct embodiments; claim 5 can depend from any one of claim 1, 2, 3, or 4, with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed in accordance with 35 U.S.C. § 112(f). Elements not presented in requisite means-plus-function format are not intended to be construed in accordance with 35 U.S.C. § 112(f). Embodiments of the invention in which an exclusive property or privilege is claimed are defined as follows.

The invention claimed is:

1. A bone biopsy system comprising:
   a cutting assembly comprising:
      a cutting cannula that comprises a cutting tip positioned at a distalmost end thereof and that defines a lumen, the cutting tip being configured to cut bone; and
      a first hub attached to the cutting cannula, the first hub comprising a first connection interface;
   an insert assembly comprising:
      an elongated insert sized to be received within the lumen of the cutting cannula, the elongated insert comprising a distal tip; and
      a second hub attached to the elongated insert, the second hub comprising a driver connector and further comprising a second connection interface configured to cooperate with the first connection interface to rotationally lock the second hub relative to the first hub; and
   a manual handle either coupled to or couplable with the first hub so as to be rotationally locked relative to the first hub,
   the bone biopsy system being selectively convertible from a power drilling configuration to a manual coring configuration,
   wherein, when the bone biopsy system is in the power drilling configuration, the insert assembly is coupled with the cutting assembly such that:
      the elongated insert is received within the lumen of the cutting cannula such that the distal tip of the elongated insert:
         is positioned distal to the cutting tip of the cutting cannula;
         sits flush with a portion of the cutting tip; or
         sits slightly recessed relative to a portion of the cutting tip while the elongated insert prevents material from entering the cutting cannula;
      the first and second connection interfaces cooperate to rotationally lock the second hub relative to the first hub; and
      the driver connector is couplable to a powered driver to permit the powered driver to rotate the insert assembly and the cutting assembly in unison, and
   wherein, when the bone biopsy system is in the manual coring configuration, the insert assembly is decoupled from the cutting assembly and the handle is coupled with the first hub to permit manual rotation of the cutting assembly.

2. The bone biopsy system of claim 1, wherein the handle is configured to be selectively coupled to and selectively decoupled from the first hub.

3. The bone biopsy system of claim 2, wherein the handle comprises a third connection interface that is configured to cooperate with the first connection interface of the first hub to rotationally lock the handle relative to the first hub.

4. The bone biopsy system of claim 2, further comprising an extraction assembly configured to couple with the cutting assembly, wherein the extraction assembly comprises the handle.

5. The bone biopsy system of claim 4, wherein the extraction assembly comprises an extraction cannula attached to the handle, the extraction cannula being configured to be received within the lumen of the cutting cannula.

6. The bone biopsy system of claim 1, wherein the handle is permanently attached to the first hub.

7. The bone biopsy system of claim 6, wherein the first connection interface comprises a medical connector configured to couple with a medical device for aspiration through the cutting cannula.

8. The bone biopsy system of claim 1, wherein the elongated insert comprises a trocar that comprises a cutting tip configured to cut through cortical bone, and wherein the cutting tip of the trocar is positioned distal to the cutting tip of the cutting cannula when the elongated insert is received within the lumen of the cutting cannula.

9. The bone biopsy system of claim 8, wherein the cutting cannula comprises a tubular member having a plurality of cutting teeth at a distal tip thereof.

10. The bone biopsy system of claim 1, wherein the elongated insert comprises an obturator.

11. The bone biopsy system of claim 10, wherein the cutting cannula comprises a needle.

12. The bone biopsy system of claim 1, further comprising the powered driver.

13. The bone biopsy system of claim 1, wherein the first connection interface comprises a medical connector configured to couple with a medical device for aspiration through the cutting cannula.

14. The bone biopsy system of claim 1, wherein the first hub further comprises a medical connector that is independent from the connection interface, wherein the medical connector is configured to couple with a medical device for aspiration through the cutting cannula.

15. The bone biopsy system of claim 1, wherein the cutting cannula comprises a constriction at a distal end thereof that reduces an inner diameter of the cutting cannula relative to more proximal regions of the cutting cannula.

16. The bone biopsy system of claim 15, further comprising an extraction cannula that comprises a plurality of resilient gripping arms at a distal end thereof, wherein a proximal end of the constriction comprises a chamfered surface configured to deflect the gripping arms inward as the extraction cannula is advanced distally through the cutting cannula.

17. The bone biopsy system of claim 1, further comprising an extraction assembly that comprises an extraction cannula sized to be received within the lumen of the cutting cannula.

18. The bone biopsy system of claim 17, wherein the extraction cannula comprises a plurality of resilient gripping arms at a distal end thereof.

19. The bone biopsy system of claim 17, wherein the bone biopsy system is convertible from the manual coring configuration to an extraction configuration in which the extraction cannula is advanced into the cutting cannula.

20. The bone biopsy system of claim 1, further comprising a manual driver configured to selectively couple with the manual handle.

21. The bone biopsy system of claim 1, further comprising a safety shield configured to automatically attach to a distal end of the elongated insert when the elongated insert is withdrawn from the cutting assembly.

22. The bone biopsy system of claim 1, wherein the first hub comprises a plurality of wings that extend laterally away from a longitudinal axis of the cutting cannula, the plurality of wings being configured for gripping by a user to assist in removing the cutting cannula from a bone of a patient after the cutting cannula has been drilled into the bone.

23. A kit comprising:
   the system of claim 1; and
   instructions for using the system, wherein the instructions comprise directions to:
      couple the insert assembly with the cutting assembly;

couple a powered driver to the insert assembly;
actuate the powered driver to drill the cutting assembly through the cortical layer of a bone; and
decouple the insert assembly from the cutting assembly while the cutting assembly extends through the cortical layer of the bone.

24. A bone biopsy system comprising:
a cutting cannula that comprises a cutting tip positioned at a distalmost end thereof, the cutting tip being configured to cut bone;
a first hub attached to the cutting cannula, the first hub comprising a first connection interface;
an elongated insert;
a second hub attached to the elongated insert, the second hub comprising a driver connector and further comprising a second connection interface configured to cooperate with the first connection interface to rotationally lock the second hub relative to the first hub; and
a manual handle either coupled to or couplable with the first hub so as to be rotationally locked relative to the first hub,
the bone biopsy system being selectively convertible from a power drilling configuration to a manual coring configuration,
wherein, when the bone biopsy system is in the power drilling configuration, the first and second connection interfaces cooperate to rotationally lock the second hub relative to the first hub, the elongated insert extends through a full length of the cutting cannula, and the driver connector is couplable to a powered driver to permit the powered driver to rotate the first hub and the second hub in unison, and
wherein, when the bone biopsy system is in the manual coring configuration, the second hub is decoupled from the first hub and the manual handle is coupled with the first hub such that manual rotation of the manual handle effects simultaneous rotation of the first hub and the cutting cannula.

25. A bone biopsy system comprising:
a cutting assembly comprising:
a cutting cannula that comprises a cutting tip positioned at a distalmost end thereof and that defines a lumen, the cutting tip of being configured to cut bone; and
a first hub coupled to the cutting cannula, the first hub comprising a first connection interface; and
an insert assembly comprising:
an elongated member sized to be inserted into the lumen of the cutting cannula, the elongated member comprising a cutting tip; and
a second hub coupled to the elongated member, the second hub comprising:
a drilling interface configured to be coupled with a powered drill; and
a second connection interface configured to couple with the first connection interface of the first hub to rotationally lock the first and second hubs relative to each other such that rotation of the second hub via the powered drill effects rotation of the cutting assembly,
the bone biopsy system being selectively convertible from a power drilling configuration to a manual coring configuration,
wherein, when the bone biopsy system is in the power drilling configuration, the insert assembly is coupled with the cutting assembly such that the elongated member extends through a full length of the cutting cannula and the cutting tip of the elongated member is positioned distal to the cutting tip of the cutting cannula, and
wherein, when the bone biopsy system is in the manual coring configuration, the insert assembly is not coupled with the cutting assembly.

26. The bone biopsy system of claim 1, wherein the handle is configured to be present on the first hub when the driver connector of the second hub is coupled to the powered driver.

27. The bone biopsy system of claim 1, wherein the driver connector of the second hub is directly connectable to the powered driver.

28. The bone biopsy system of claim 12, wherein the driver connector of the second hub and the powered driver are configured to be directly connected to each other.

29. The bone biopsy system of claim 1, wherein the cutting tip of the cutting cannula comprises a plurality of teeth or serrations configured to cut through cortical bone.

30. The bone biopsy system of claim 1, wherein the cutting tip of the cutting cannula is configured to pass through a cortical layer of bone.

* * * * *